US005659023A

United States Patent [19]
Alexander et al.

[11] Patent Number: 5,659,023
[45] Date of Patent: Aug. 19, 1997

[54] NUCLEOTIDE ANALOGUES

[75] Inventors: Petr Alexander, San Mateo; Ernest J. Prisbe, Los Altos, both of Calif.

[73] Assignee: Gilead Sciences, Inc., Foster City, Calif.

[21] Appl. No.: 384,504

[22] Filed: Feb. 1, 1995

[51] Int. Cl.$^6$ .............. C12Q 1/68; C07H 21/02; C07H 21/04; C12P 19/34
[52] U.S. Cl. .............. 536/22.1; 435/6; 435/91.2; 536/25.3; 536/26.1
[58] Field of Search ............... 536/25.3, 26.1, 536/22.1; 435/6, 91.2

[56] References Cited

U.S. PATENT DOCUMENTS

| | | | |
|---|---|---|---|
| 5,059,690 | 10/1991 | Zahler et al. | 544/276 |
| 5,276,143 | 1/1994 | Sabesan et al. | |
| 5,314,893 | 5/1994 | Tino et al. | 514/274 |
| 5,414,000 | 5/1995 | Tino et al. | 514/261 |

FOREIGN PATENT DOCUMENTS

| | | | |
|---|---|---|---|
| 0 398 231 A2 | 11/1990 | European Pat. Off. | C07H 19/10 |
| WO 92/13869 | 8/1992 | WIPO . | |
| WO 95/07919 | 3/1995 | WIPO . | |
| WO 95/09720 | 3/1995 | WIPO . | |

OTHER PUBLICATIONS

Jasko et al., "5'-Phosphonates of Ribonucleosides and 2'-Deoxyribonucleosides: Synthesis and Antiviral Activity," Nucls & Nuclt 12(8):879–893 (1993).

Perez–Perez et al., "Synthesis and Antiviral Activity of Phosphonate Derivatives of Enantiomeric Dihydro–2H–Pyranyl Nucleosides," Bioorg Med Chem Lett 5(11):1115–1118 (1995).

Alexander et al., "Synthesis and Antiviral Activity of Pyranosylphosphonic Acid Nucleotide Analogues," J Med Chem 39:1321–1330 (1996).

Schmitz et al., "Nonradioactive Labeling of Oligonucleotide in Vitro with the Hapten Digoxigenin by Tailing with Terminal Transferase," Anal Biochem 192:222–231 (1991).

Xiong et al., "Kinetic Analysis of the Interaction of Cidofovir Diphosphate with Human Cytomegalovirus DNA Polymerase," Biochem Pharm 51:1563–1567 (1996).

Aerschot et al., "Synthesis and Anti–HIV Activity of Dideoxycytidine Analogues Containing a Pyranose Carbohydrate Moiety," Nucl & Nuclt 10(1–3):589–590 (1991).

Augustyns et al., "Sugar Modified Oligonucleotides," Nucls & Nuclt 10(1–3):587–588 (1991).

Bessodes et al., "Synthesis of Unsaturated 4'–Azido Pyranosyl Thymines as Potential Antiviral and anti–HIV Agents," J. Chem Soc Perkin Trans I 3035–3039 (1990).

Crane et al., "Isonucleosides from Glucosamine," J Carbohydrates Nucls Nuclt 7(5):281–296 (1980).

Hansen et al., "Synthesis of 3'–Azido–2,3'–dideoxy–beta-–D–arabino–hexopyranosyl Nucleosides," Lebigs Ann. Chem 1079–1082 (1990).

Kim et al., "Synthesis and HIV Activity of Phosphonate Isosteres of D4T Monophosphate," Bioorg Med Chem Lett 5(2):367–370 (1992).

Kira et al., "Anti–Herpes Activites of Isonucleoside Analogues with Variable Bases at the 2' Position," Nucls & Nuclt 14(3–5):571–574 (1995).

Perez–Perez et al., "Phosphonates Derivatives of 2',3'–Dideoxy–2',3'–Didehydro–Pentopyranosyl Nucleosides," Nucls & Nuclt 14(3–5):707–710 (1995).

Verheggen et al., "Synthesis and Antiherpes Virus Activity of 1,5–Anhydrohexitol Nucleosides," J Med Chem 36:2033–2040 (1993).

Weil, Edward D., "Phosphorous–Based Flame Retardants," Handbook of Organophosphorus Chemicals 683 and 709–711 (1992).

Yokota et al, "Inhibitory effects of acyclic nucleoside phosphonate analogues on hepatitis B virus DNA synthesis in HB611 cells," Antiviral Chem & Chemo 5(2):57–63 (1994).

Engel, R., "Phosphonates as Analogues of Natural Phosphates," Chem Rev 77(3):349–367 (1977).

Tino et al., "Synthesis and Antiviral Activity of Novel Isonucleoside Analogs," J Med Chem 36:1221–1229 (1993).

Bergstrom et al, "Organoiron mediated alkylation of phosphite esters: Synthesis of (Dicarbonyl)(n5–cyclopentadienyl)iron–derived nucleoside phosphonate esters", J. Org. Chem. 57:873–876 1992.

Mitchell et al, "Boron trifluoride–methanol complex as a nondepurinating detritylating agent in DNA synthesis", Nucleic Acids Res. 18(17) 5321 (Abstract Only) 1990.

Caruthers, "Synthesis of oligonucleotides and oligonucleotide analogues" in (Antisense inhibitors of Gene Expression, pp. 7–24, J.S. Cohen ed., CRC press, Boca Raton, FL) 1989.

Niedlein et al, "Synthesen und Untersuchungen von [Oxazolo[2,3–a]isoindol–9b(2H)–yl]phosphonaten und–phosphinaten: eine neue klasse von heterocyclen", Helv. Chim. Acta 76:2407–2417 1993.

Renault et al, "Synthesis and antiviral evaluation of furopyrimidine diones cyclic and acyclic, nucleoside analogues", Heterocycles 41(5):937–945 1995.

Jois et al, "Synthesis and antiviral evaluation of some novel [1,2,4]triazolo[4,3–b][1,2,4]triazole nucleoside analogs", J. Heterocyclic Chem. 30:1289–1292 1993.

(List continued on next page.)

*Primary Examiner*—George C. Elliott
*Assistant Examiner*—Jeffrey Fredman
*Attorney, Agent, or Firm*—Max D. Hensley

[57] ABSTRACT

In accordance with this invention novel compounds are provided that are selected from saturated and unsaturated pyrans and furans substituted with at least a phosphonate group and a heterocyclic base. These compounds are useful as antiinfectives, flame retardants, diagnostic oligonucleotides and immunogens.

24 Claims, No Drawings

OTHER PUBLICATIONS

Rosowsky et al, "Synthesis of 3'-o-propargylthymidine as a candidate antiretroviral agent", Nucleosides Nucleotides 8(4):491–497 1989.

Pattenden et al, "Maleic anhydrides in synthesis. Preparation of furan-2(5h)-one phosphonate derivatives and a new synthesis of pulvinic acids and pulvinone analogues", J. Chem. Soc. Perkin Trans. 1:2357–2361 1991.

Engstler et al, "N-(4-nitrophenyl)oxamic acid and related N-acylanilines are non competitive inhibitors of Vibrio cholerae sialidase but do not inhibit trypanozoma cruzi or trypanosoma brucei trans-sialidases", Helv. Chim. Act. 77:1166–1173 1994.

Otmar et al, "[5-(adenin-9-yl)-5-deoxypentofuranosyl] phosphonates—a novel type of nucleotide analogs related to HPMA", Collect. Czech. Chem. Commun. 58:2159–2179 1993.

Kamber et al, "gamma-phosphono-gamma lactones. The use of allyl esters as easily removable phosphonate protecting groups", Can. J. Chem. 63:823–827 1985.

NUCLEOTIDE ANALOGUES

This application relates to nucleotide analogues and to their use in diagnostic and therapeutic methods. It relates to immunogens and oligonucleotides containing such nucleotide analogues.

Nucleotide analogues containing phosphonate groups are disclosed for example in U.S. Pat. Nos. 4,659,825, 4,808,716, 4,724,233, 5,142,051, 5,302,585, 5,208,221, 5,352,786, 5,356,886 and in EP publication numbers 269,947, 481,214, 630,381, 369,409, 454,427 and 618,214. EP 398,231 discloses a structure

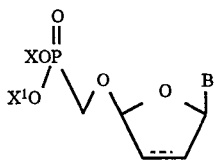

where B is a purine or pyrimidine base, X and $X^1$ are H or $C_1$–$C_6$ alkyl, the broken line designates an optional double bond, Y and X are unsubstituted or substituted $C_1$–$C_6$ alkyl or together they constitute an oxygen atom or methylene group in which event the broken line is a single bond.

Verheggen et al. "J. Med. Chem." 36:2033–2040 (1993) disclose various antiviral pyrans as shown below

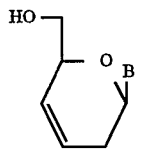 (a)

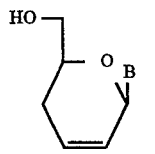 (b)

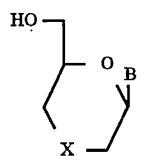 (c)

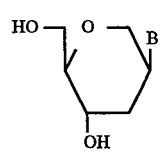 (d)

wherein B are defined pyrimidine and purine heterocycles and X is a defined heterogroup. Verheggen et al. disclose the 4-hydroxymethyl and 4-phosphonylmethoxy analogues of compound (b).

U.S. Pat. No. 5,276,143 discloses incorporating certain dideoxyfructonucleosides and deoxyfructonucleotides into oligonucleotides.

U.S. Pat. No. 5,314,893 discloses various antiviral tetrahydropyrans.

It is an object of this invention to provide antiviral compounds having an improved selectivity index, i.e., that are less toxic yet more efficacious than nucleotide analogues known heretofore.

It is another object to prepare compounds that are suitable for facilitating the labelling of oligonucleotide probes and polypeptides.

It is an additional object to provide compounds useful in the preparation of fire retardant resins.

It is a further object to obtain nucleotide analogues that are useful as anti-infective agents.

SUMMARY OF THE INVENTION

The objects of this invention are accomplished by novel compounds having structure (1)

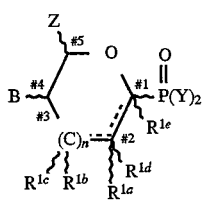 (1)

wherein the dashes indicate the positions of optional double bonds;

\# designates chiral centers, which are numbered;

n is 0 or 1;

Y independently is OH, —$OR^3$, —$OCH(R^3)OC(O)R^3$, an oligonucleotide, —OPRT, a monophosphate, a diphosphate, an amino acid amidate, a polypeptide amidate, —$NHR^3$, or —$N(R^3)$;

PRT is a protecting group;

Z is $CH_2OR^2$, halo substituted $C_1$–$C_2$ alkyl, CH=$CH_2$, C≡CH, —$CH_2N_3$, $CH_3$, a detectable label or H;

B is a heterocyclic base;

$R^{1a}$ and $R^{1b}$ independently are H, CN, $N_3$, halo, $OR^2$, $C_1$–$C_3$ alkyl or $C_1$–$C_3$ alkyl substituted by $N_3$, OH, halo, CN or $OR^2$, or $R^{1a}$ and $R^{1b}$ may be joined together to form a 1,2-diol protecting group, a bond, or —$CH_2$—;

$R^{1c}$ is H or, when $R^{1a}$ and $R^{1b}$ are joined together to form a bond, $R^{1c}$ is H or F;

$R^{1d}$ and $R^{1e}$ are H or may be joined together to form a bond;

$R^2$ independently is H, —$C(O)R^3$, PRT, an oligonucleotide, a monophosphate or a diphosphate;

$R^3$ independently is unsubstituted alkyl, aryl, alkenyl, alkynyl, alkaryl, alkynylaryl or alkenylaryl; said groups where H is substituted by halo, carboxy, hydroxyl, cyano, nitro, N-morpholino, or amino; and/or said groups where —$CH_2$— has been substituted by NH, S, or O;

Z and one Y group may be joined together to form a ring if Z is $CH_2OH$ and Y is OH;

one Y group and $R^{1a}$ or $R^{1b}$ may be joined together to form a ring if Y is OH and said $R^{1a}$ or $R^{1b}$ group comprises OH, provided that ring positions 1–2 of the furan or pyran ring are saturated and, when $R^{1a}$ is OH which is cyclized with Y, then $R^{1a}$ and the P atom are located on the same side of the ring;

when Y and Z or Y and $R^{1a}$ or $R^{1b}$ form a ring, the P atom becomes chiral center \#6;

when n=1 the pyran ring is saturated or is unsaturated at the 1–2 or 2–3 positions;

when n=0, $R^{1d}$ and $R^{1e}$ are H; and the salts thereof.

In another embodiment of the invention a method is provided for the detection of a target nucleic acid sequence comprising:

(a) providing a labelled oligonucleotide probe having structure (1)

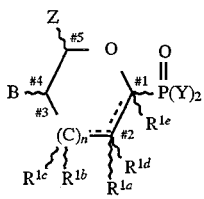

(1)

wherein the dashes indicate the positions of optional double bonds;

\# designates chiral centers, which are numbered;

n is 0 or 1;

Y independently is OH, —OR$^3$, —OCH(R$^3$)OC(O)R$^3$, an oligonucleotide, —OPRT, a monophosphate, a diphosphate, an amino acid amidate, a polypeptide amidate, —NHR$^3$, or —N(R$^3$);

PRT is a protecting group;

Z is CH$_2$OR$^2$, halo substituted C$_1$–C$_2$ alkyl, CH=CH$_2$, C≡CH, —CH$_2$N$_3$, CH$_3$, a detectable label or H;

B is a heterocyclic base;

R$^{1a}$ and R$^{1b}$ independently are H, CN, N$_3$, halo, OR$^2$, C$_1$–C$_3$ alkyl or C$_1$–C$_3$ alkyl substituted by N$_3$, OH, halo, CN or OR$^2$, or R$^{1a}$ and R$^{1b}$ may be joined together to form a 1,2-diol protecting group, a bond, or —CH$_2$—;

R$^{1c}$ is H or, when R$^{1a}$ and R$^{1b}$ are joined together to form a bond, R$^{1c}$ is H or F;

R$^{1d}$ and R$^{1e}$ are H or may be joined together to form a bond;

R$^2$ independently is H, —C(O)R$^3$, PRT, an oligonucleotide, a monophosphate or a diphosphate;

R$^3$ independently is unsubstituted alkyl, aryl, alkenyl, alkynyl, alkaryl, alkynylaryl or alkenylaryl; said groups where H is substituted by halo, carboxy, hydroxyl, cyano, nitro, N-morpholino, or amino; and/or said groups where —CH$_2$— has been substituted by NH, S, or O;

Z and one Y group may be joined together to form a ring if Z is CH$_2$OH and Y is OH;

one Y group and R$^{1a}$ or R$^{1b}$ may be joined together to form a ring if Y is OH and said R$^{1a}$ or R$^{1b}$ group comprises OH, provided that ring positions 1-2 of the furan or pyran ring are saturated and, when R$^{1a}$ is OH which is cyclized with Y, then R$^{1a}$ and the P atom are located on the same side of the ring;

when Y and Z or Y and R$^{1a}$ or R$^{1b}$ form a ring, the P atom becomes chiral center #6;

when n=1 the pyran ring is saturated or is unsaturated at the 1-2 or 2-3-positions;

when n=0, R$^{1d}$ and R$^{1e}$ are H;

provided that one Y is an oligonucleotide having a sequence that is complementary to that of the target sequence; and the salts thereof;

(b) hybridizing the labelled oligonucleotide probe to the target nucleic acid; and (c) detecting the bound labelled oligonucleotide probe.

A further embodiment provides a method for treatment of viral infections comprising administering to a subject a therapeutically effective amount of a compound having structure (1)

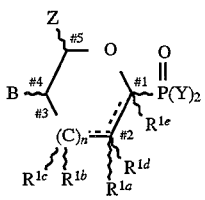

(1)

wherein \#, B, Y, Z, R$^{1a}$, R$^{1b}$, R$^{1c}$, R$^{1d}$, R$^{1e}$, n and the dashed lines are defined above.

The invention herein also includes novel synthetic methods. One such method comprises (a) providing a compound having structure (I)

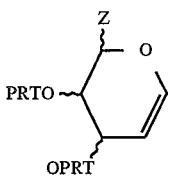

(I)

wherein PRT is defined above, and Z is CH$_2$OPRT, halo-substituted C$_1$–C$_2$ alkyl, CH=CH$_2$, C≡CH, —CH$_2$N$_3$, CH$_3$ or H;

(b) reacting the compound of structure (I) with P(OPRT)$_3$ in the presence of a Lewis Acid; and (c) recovering from the reaction mixture of step (b) a compound having structure (II)

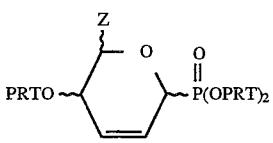

(II)

This method is unexpectedly superior to the same method using dialkyl phosphonic acid in that far less by-products are produced and yields accordingly increase from about 20% to greater than about 90%.

Another method of this invention also relates to double bond migration in pyranose derivatives. It comprises (a) providing a compound having structure (III)

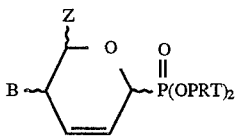

(III)

(b) treating the compound with a base; and (c) recovering from the reaction mixture of step (b) a compound having structure (IV)

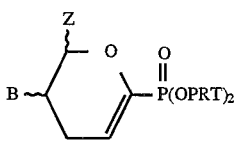

(IV)

wherein B is defined above, and Z and PRT are defined in the preceding method.

DETAILED DESCRIPTION OF THE INVENTION

As used herein, and unless modified by the immediate context: 1. Alkyl means C$_1$–C$_{15}$ branched, normal or cyclic saturated hydrocarbons and includes methyl, ethyl, propyl, cyclopropyl, isopropyl, n-, sec-, iso- and tert-butyl, cyclobutyl and the like. 2. Alkenyl means $C_2$–$C_{15}$ branched, normal or cyclic hydrocarbons containing at least 1 (generally 1–3) cis or trans oriented conjugated or unconjugated double bond, including ethenyl, propenyl, isopropenyl, 1-, 2- and 3-butenyl, 1- and 2-isobutenyl and the like. 3. Alkynyl means $C_2$–$C_{15}$ branched, normal, or cyclic hydrocarbons bearing at least 1 (generally 1–3) triple bond, e.g., 2-propynyl. 4. Aryl means an unsaturated resonant cyclic or fused polycyclic ring structure containing at least one 3–6 membered ring containing ring atoms solely of carbon or of carbon and at least one N—, S— or O— heteroatom, including phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl or 2-, 4- and 5-pyrimidinyl. 5. Alkenylaryl means alkenyl substituted with at least 1 (generally 1–3) aryl group and bonded through the alkenyl or aryl moiety to the remainder of the compound through saturated or unsaturated carbon. 6. Alkynylaryl means alkynyl substituted with at least 1 (generally 1–3) aryl group and bonded through the alkenyl or aryl moiety to the remainder of the compound through saturated or unsaturated carbon.

Stereochemistry is depicted according to carbohydrate convention with the furan or pyran oxygen at the rear of the molecule, and the stereoconfiguration of the substituents indicated by their position above and below the plane of the ring. The bonds that project from the side of the ring (substituents of unsaturated ring carbon atoms) are coplanar with the ring (unless indicated to the contrary by the bond designation ⁓⁓⁓, which designates the genus of diastereomers and racemates). Hydrogen atoms bound to ring carbons may not show but shall be understood to occupy any undesignated valence of the ring carbon atoms. Such hydrogen atoms generally are in the opposite configuration of any group or atom that also may be bound to the same saturated carbon atom.

Group Z typically is $CH_2OH$, $CH_2OR^2$, H, $CH_3$ or vinyl. Generally, it is in the D configuration, but may be in the L configuration or racemic. When Z contains a reactive functionality like OH the reactive group generally is protected (see infra) throughout the synthesis, and is deprotected as one of the last steps in the synthesis. Thus in $CH_2OR^2$, $R^2$ commonly is PRT. Z is a convenient site for the attachment of oligonucleotide or of detectable moieties such as biotin, fluorescent groups and the like using methods known per se. In other embodiments where Z is $CH_2OH$, Z is internally cyclized by dehydration with a hydroxyl group of the phosphonate, whereby compounds having the partial structure (2) are obtained (the omitted structural subunit is found in structure (1); in this and the following structures where $R^{1c}$, $R^{1d}$ and $R^{1e}$ are not depicted they are H or a bond as dictated by their context):

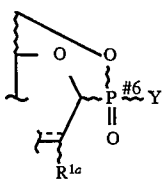

(2)

wherein Y and $R^{1a}$ are defined above.

Groups $R^{1a}$ and $R^{1b}$ are saturated C atom substituents or are taken together to form a bond. $R^{1a}$ or $R^{1b}$ groups typically will be selected from H, $OR^2$, OH, lower alkyl, azido or fluoro. An atomic $R^{1a}$ substituent is not bound to an unsaturated C atom. Either the (R) or (S) configuration of $R^{1a}$ or $R^{1b}$ are acceptable, and $R^{1a}$ and $R^{1b}$ may possess the same or different stereochemistry. $R^{1a}$ or $R^{1b}$, like Y or Z, is a convenient site for substitution of an oligonucleotide or a detectable label for use in diagnostics.

In one embodiment of the invention at least one $R^{1a}$ or $R^{1b}$ is OH and is internally cyclized by dehydration with a hydroxyl group of the phosphonate, whereby compounds having the partial structures (3) or (4) are obtained.

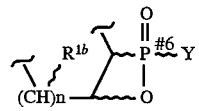

(3)

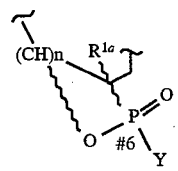

(4)

wherein Y, n, $R^{1a}$ and $R^{1b}$ are defined above. Cyclization introduces chirality into the P atom, designated #6. Y in structures (2)–(4) is (R) or (S), or may be racemic. The cyclic oxygen atom in structure (3) will be located on the same side of the plane of the furan or pyran ring as the phosphorous atom.

$R^{1c}$ typically is H, whether $R^{1a}$ and $R^{1b}$ are joined to form a bond or not, but may be fluoro when $R^{1a}$ and $R^{1b}$ form a bond.

$R^{1d}$ and $R^{1e}$ typically are H, but may be joined together to form a bond. When n=1, only one of $R^{1a}$ and $R^{1b}$ or $R^{1d}$ and $R^{1e}$ may be taken together to form a bond; when n=0, $R^{1d}$ and $R^{1e}$ are H.

n. In general the pyranose ring is preferred, i.e., n=1. Moreover, preferably the 2–3 carbon bond of this ring is a double bond.

Group $R^2$ typically is H or an ester-forming group —C(O)$R^3$ bound to any one or more of the pyran or furan hydroxyl substituents $R^{1a}$, $R^{1b}$ or Z. Synthetic reactions may require that $R^2$=PRT. $R^2$ is not critical and can vary widely. Principally, $R^2$ groups serve as protecting groups during synthetic reactions or groups that are capable of cleavage in vivo (generally, esters) to yield the free hydroxyl. Note that some —C(O)$R^3$ are capable of acting as PRT (see infra).

Group $R^3$ also is not a critical functionality and may vary widely. $R^3$ for example includes $C_3$–$C_6$ aryl (including phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl), $C_3$–$C_6$ aryl substituted with halo, alkyl $C_1$–$C_{12}$ alkoxy, CN, $NO_2$, OH, carboxy, carboxyester, thiol, thiolester, $C_1$–$C_{12}$ haloalkyl (1–6 halogen atoms), $C_2$–$C_{12}$ alkenyl or $C_2$–$C_{12}$ alkynyl [including 2-, 3- and 4-alkoxyphenyl ($C_1$–$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl], 2,3-, 2,4-, 2,5-, 2,6-, 3,4- and 3,5-dimethylphenyl, 2,3-, 2,4-, 2,5-, 2,6-, 3,4- and 3,5- biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-,3- and 4-acetylphenyl, 1,8-dihydroxynaphthyl (—O—$C_{10}H_6$—OH) and aryloxy ethyl [$C_6$-$C_9$ aryl (including phenoxy ethyl)], 2,2'-dihydroxybiphenyl, alkoxy ethyl [$C_1$-$C_6$ alkyl including —$CH_2$—$CH_2$—O—$CH_3$ (methoxy ethyl)], alkyl substituted by OH or by 1 to 3 halo atoms (including —$CH_3$, —CH ($CH_3$)$_2$, —C($CH_3$)$_3$, —$CH_2CH_3$, —($CH_2$)$_2CH_3$, —($CH_2$)$_3CH_3$, —($CH_2$)$_4CH_3$, —($CH_2$)$_5CH_3$, —$CH_2CH_2F$, —$CH_2CH_2Cl$, —$CH_2CF_3$, and —$CH_2CCl_3$), 2-, 3- and 4-N,N-dialkylaminophenol, —$C_6H_4CH_2$—N($CH_3$)$_2$,

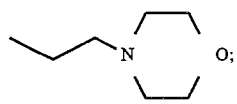

—N-2-propylmorpholino, 2,3-dihydro-6-hydroxyindene, sesamol, catechol monoester, —$CH_2$—C(O)—N($R^{15}$)$_2$ wherein each $R^{15}$ is the same or different H or $C_1$-$C_4$ alkyl, —$CH_2$—S(O)($R^{15}$), —$CH_2$—S(O)$_2$($R^{15}$), —$CH_2$—CH(OC (O)$CH_2R^{15}$—$CH_2$(OC(O)$CH_2R^{15}$), cholesteryl, a 5 or 6 carbon monosaccharide, disaccharide or oligosaccharide (3 to 9 monosaccharide residues), enolpyruvate (HOOC—C (=$CH_2$)O), glycerol, α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids), trimethoxybenzyl, triethoxybenzyl, 2-alkyl pyridinyl ($C_{1-4}$ alkyl),

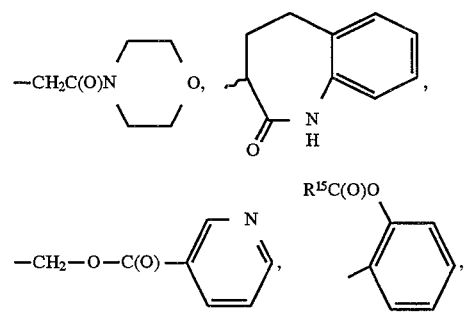

$C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2$—$CCl_3$), $C_1$-$C_{12}$ alkyl (including methyl and ethyl), $C_2$-$C_{12}$ alkenyl or $C_2$-$C_{12}$ alkynyl, and other compounds set forth in Table 7 below. The hydroxyl groups of Z, $R^{1a}$ and/or $R^{1b}$ optionally are substituted with one of groups III, IV or V disclosed in WO94/21604.

PRT is a protecting group used to prevent side reactions with the protected group during synthetic procedures. For the most part the decision as to which groups to protect, when to do so, and the nature of the PRT will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect hydroxyl or amino groups. The latter are found on some heterocyclic bases, while hydroxyl PRT (—OPRT) are used to protect Y, $R^1$ and Z hydroxyl groups. The order of deprotection to yield free hydroxyl also is dependent upon the intended direction of the synthesis and the reaction conditions to be encountered. Typically the Z, B, Y and $R^1$ groups all will be protected and thereafter will be deprotected in any order as required. For example, heterosubstitution at the $R^1$ groups generally will require that one $R^1$OH be unprotected or differently protected than the other $R^1$ (see scheme 1). In other embodiments, the Y hydroxyl groups and/or B amino groups are not protected but Z and $R^1$ are —$CH_2$OPRT or —OPRT, respectively.

A very large number of hydroxy protecting groups and corresponding chemical cleavage reactions are described in "Protective Groups in Organic Chemistry", Theodora W. Greene (John Wiley & Sons, Inc., New York, 1991, ISBN 0-471-62301-6) ("Greene"). As will be seen from the discussion below, some $R^3$ groups described above also are capable of acting as PRT.

Typical hydroxy protecting groups are described in Greene at pages 14–118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis (2-chloroethoxy)methyl, 2-(Trimethylsilyl)ethoxymethyl, Tetrahydropyranyl, 3-Bromotetrahydropyranyl, Tetrahydrothiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3, 3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobentzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl) phenylmethyl, Tri(p-methoxyphenyl)methyl, 4-(4'-Bromophenacyloxy)phenyldiphenylmethyl, 4,4',4"-Tris(4, 5-dichlorophthalimidophenyl)methyl, 4,4',4"-Tris (levulinoyloxyphenyl)methyl, 4,4',4"-Tris (benxoyloxyphenyl)methyl, 3-(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3-tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, hydroxy protecting groups include substituted methyl ethers, substituted benzyl ethers, silyl ethers, and esters including sulfonic acid esters, still more typically, trialkylsilyl ethers, tosylates and acetates.

Typical 1,2-diol protecting groups (thus, generally where two $R^1OH$ groups are taken together with a protecting functionality) are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table 1a, still more typically, epoxides, acetonides, cyclic ketals and aryl acetals.

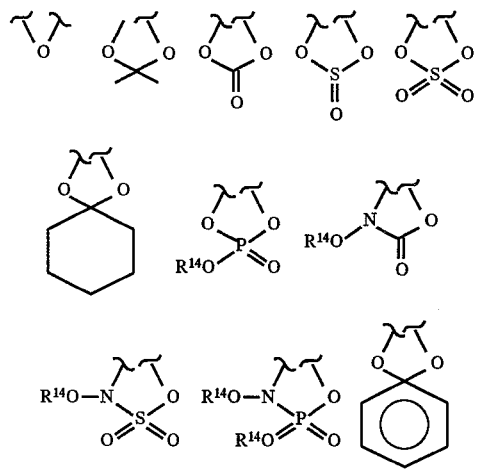

wherein $R^{14}$ is $C_1-C_6$ alkyl.

Group Y typically will be OH or convertible to OH by chemical or biological means. For in vivo hydrolysis Y usually is $OR^3$ in which $R^3$ is phenyl or substituted phenyl as described below or Y is —$OCH(R^3)OC(O)R^3$. Y is OPRT in intermediates for the most part. Certain end uses for intermediate compounds of the invention contemplate Y=an oligonucleotide or protein.

Particularly useful Y groups are alkylacyloxymethyl groups and their derivatives, including —CH($CH_2CH_2OCH_3$)OC(O)C($CH_3$)$_3$,

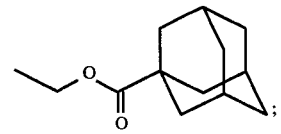

—$CH_2OC(O)C_{10}H_{15}$, —$CH_2OC(O)C(CH_3)_3$, —CH($CH_2OCH_3$)OC(O)C($CH_3$)$_3$, —CH(CH($CH_3$)$_2$)OC(O)C($CH_3$)$_3$, —$CH_2OC(O)CH_2CH(CH_3)_2$, —$CH_2OC(O)C_6H_{11}$, —$CH_2OC(O)C_6H_5$, —$CH_2OC(O)C_{10}H_{15}$, —$CH_2OC(O)CH_2CH_3$, —$CH_2OC(O)CH(CH_3)_2$, —$CH_2OC(O)C(CH_3)_3$ and —$CH_2OC(O)CH_2C_6H_5$.

Y also may be an amino acid residue. In general, the amino acid residue has the structure $R^4OC(O)CH(R^5)NH—$, where $R^4$ is $R^3$, one or more additional amino acid residues linked via peptide bonds, or H and $R^5$ is alkyl substituted with amino, carboxyl, amide, carboxyl ester, hydroxyl, $C_6-C_7$ aryl, guanidinyl, imidazolyl, indolyl, sulfhydryl, sulfoxide, and/or alkylphosphate. Ordinarily $R^4$ is $R^3$ and $R^5$ is a side chain of a naturally occurring amino acid. With respect to the carboxyl-containing side chains it will be understood that if the C atom of the subject carboxyl is linked by 5 or less atoms to the phosphoamide N then the carboxyl optionally will be blocked, e.g. by esterification with $R^3$ or amidation wherein the ester or amide bonds are hydrolyzable in vivo. $R^5$ also is taken together with the amino acid αN to form a proline residue ($R^5$=—$(CH_2)_3$—). However, $R^5$ is generally a side group such as H, —$CH_3$, —CH($CH_3$)$_2$, —$CH_2$—CH($CH_3$)$_2$, —$CHCH_3$—$CH_2$—$CH_3$, —$CH_2$—$C_6H_5$, —$CH_2CH_2$—S—$CH_3$, —$CH_2OH$, —CH(OH)—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—C($NH_2$)—$NH_2$. $R^5$ also includes 1-guanidinoprop-3-yl, benzyl, 4-hydroxybenzyl, imidazol-4-yl, indol-3-yl, methoxyphenyl and ethoxyphenyl.

When the amino acid residue contains one or more chiral centers, any of the D, L, meso, threo or erythro (as appropriate) racemates, scalemates or mixtures thereof may be used as group Y. In general, if the intermediates are to be hydrolyzed non-enzymatically (as would be the case where the compounds are used as chemical intermediates for the free acids), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acid residues include the following:

Glycyl;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues;

Amino acid amides such as glutaminyl and asparaginyl;

Polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine), diaminobutyric and histidine residues;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues;

Imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_n$COOR$^3$)$_2$, wherein n and R$^3$ are as defined above, and azetidine-2-carboxylic acid residues;

A mono- or di-alkyl (typically C$_1$–C$_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl;

Aliphatic α-amino-β-hydroxy acids such as serine, β-hydroxyleucine, β-hydroxynorleucine, β-hydroxynorvaline, and α-amino-β-hydroxystearic acid residues;

α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl;

2-hexosaminic acids such as D-glucosaminic acid or D-galactosaminic acid residues;

α-Amino-β-thiols such as penicillamine, β-thiolnorvaline or β-thiolbutyrine residues;

Other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine;

Phenylalanine, tryptophan and ring-substituted α amino acids such as the phenyl- or cyclohexylamino acids α-aminophenylacetic acid, α-aminocydohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4,6-trimethyl-, 2-ethoxy-5-nitro, 2-hydroxy-5-nitro and p-nitrophenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues;

α-Amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention particularly if they are capable of autocatalytically hydrolyzing the P-amidate bond. Thus, they should contain a free carboxyl group, or should do so upon hydrolysis in vivo.

Of particular interest are hydrophobic residues such as mono-or di-alkyl or aryl amino acids, cycloalkylamino acids and the like. These residues contribute to cell permeability by increasing the partition coefficient of the nucleotide analogue amidate. Typically, the residue does not contain a sulfhydryl or guanidino substituent.

Y optionally is a polypeptide radical. Polypeptides comprise dipeptides (2 residues), or polypeptides of 3, 5, 10 and up to 100 or more residues. They include enzymes (e.g., hydrogen peroxidase) as well as antibodies or proteins of any type against which one wishes to raise an immune response. The nature and identity of the polypeptide may vary widely. The polypeptide optionally contains a peptidolytic enzyme cleavage site at the peptide bond between the first and second residues adjacent to the phosphorus atom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus atom of the nucleotide analogue herein. It is expected that this peptide will be cleaved by the appropriate peptidolytic enzyme, leaving the carboxyl of the proximal amino acid residue to autocatalytically cleave the amidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, ED, EE EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptides are also useful as Y. The sequence -X4-pro-X5- (where X4 is any amino acid residue and X5 is an amino acid residue, a carboxyl ester of proline, or hydrogen) will be cleaved by luminal carboxypeptidase to yield X4 with a free carboxyl, which in turn autocatalytically cleaves the phosphono amidate bond. X5 usually will be a benzyl ester of the carboxy group of X5.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., "Pharm Res." 9:969–978 (1992). Transport competent peptides can thus be used to enhance bioavailability of Y amidate compounds. Di- or tripeptides having one or more amino acids in the D configuration are also compatible with peptide transport and can be utilized in Y amidate compounds. Amino acids in the D configuration can be used to reduce the susceptibility of a di- or tripeptide to hydrolysis by proteases common to the brush border such as aminopeptidase N (EC 3.4.11.2). In addition, di- or tripeptides with amino acid residues can be selected on the basis of their relative resistance to hydrolysis by proteases found in the lumen of the intestine. For example, tripeptides or oligopeptides lacking asp and/or glu are poor substrates for aminopeptidase A (EC 3.4.11.7), di- or tripeptides lacking amino acid residues on the N-terminal side of hydrophobic amino acids (leu, tyr, phe, val, trp) are poor substrates for endopeptidase 24.11 (EC 3.4.24.11), and peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Group B. B is a heterocyclic base. It typically is capable of participating in Watson-Crick base pairing, or is a protected analogue thereof. It includes any naturally-occurring heterocycle found in nucleic acids, nucleotides or nucleosides of living organisms. The heterocyclic bases generally are the purine, pyrimidine or related heterocycles shown in formulas (6)–(9).

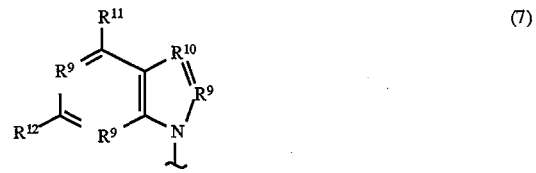

wherein $R^6$ is H, OH, F, Cl, Br, I, $OR^3$, SH, $SR^3$, $NH_2$, or $NHR^3$;

$R^7$ is N, CF, CCl, CBr, CI, $CR^8$, $CSR^8$, or $COR^8$;

$R^8$ is H, $C_1$–$C_9$ alkyl, $C_2$–$C_9$ alkenyl, $C_2$–$C_9$ alkynyl or $C_7$–$C_9$ aryl-alkyl unsubstituted, or H substituted by OH, F, Cl, Br or I, or $CH_2$ substituted by O, NH or $NR^3$; $R^8$ includes $CH_3$, $CH_2CH_3$, $CHCH_2$, CHCHBr, $CH_2CH_2Cl$, $CH_2$, $CH_2F$, $CH_2CCH$, $CH_2CHCH_2$, $C_3H_7$, $CH_2OH$, $CH_2OCH_3$, $CH_2OC_2H_5$, $CH_2OCCH$, $CH_2OCH_2CHCH_2$, $CH_2C_3H_7$, $CH_2CH_2OH$, $CH_2CH_2OCH_3$, $CH_2CH_2OC_2H_5$, $CH_2CH_2OCCH$, $CH_2CH_2OCH_2CHCH_2$, and $CH_2CH_2OC_3H_7$;

$R^9$ is N or CH;

$R^{10}$ is N, CH, CCN, $CCF_3$, CC≡CH or $CC(O)NH_2$;

$R^{11}$ is H, OH, $NH_2$, SH, $SR^3$ (such as $SCH_3$, $SCH_2CH_3$, $SCH_2CCH$, $SCH_2CHCH_2$ or $SC_3H_7$), $NH(R^3)$ (such as $NH(CH_3)$, $NH(CH_2CH_3)NH(CH_2CCH)$, $NH(CH_2CHCH_2)$ or $NH(C_3H_7)$); $N(R^3)_2$ such as $N(CH_2CH_3)_2$; or halogen (F, Cl, Br or I);

$R^{12}$ is H, OH, F, Cl, Br, I, $SR^3$ (such as $SCH_3$, $SCH_2CH_3$, $SCH_2CCH$, $SCH_2CHCH_2$ or $SC_3H_7$), $OR^3$, $NH_2$, $N(R^3)_2$ or $NHR^3$; and $R^{13}$ is O, S or Se.

Specific heterocyclic bases include the purines hypoxanthine, inosine, xanthine, 2-aminopurine, 2,6-diaminopurine, 2-amino-6-chloropurine, adenine, guanine, 6-thio-2-aminopurine and the 8-aza, 7-deaza-8-aza, 1-deaza, 7-deaza or 3-deaza derivatives of each of the foregoing purines; and the pyrimidines cytosine, thymine, uracil, 6-azacytosine; 5-fluorocytosine; 5-chlorocytosine; 5-iodocytosine; 5-bromocytosine; 5-methylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; and 5-propynyluracil. Cytosine or 5-halo- and 5-$C_1$-$C_5$-alkyl cytosine are preferred where Z=$CH_2OR^2$. For the other Z groups, B ordinarily is a purine or its monoaza or monodeaza analogue.

B includes both protected and unprotected forms of the heterocyclic bases. Protecting groups for exocyclic amines of heterocyclic bases such as adenine, cytosine, 2,6-diaminopurine and the like are known. The selection of a protecting group will be apparent to the ordinary artisan and will depend on the nature of the labile group and the chemistry which the protecting group is expected to encounter.

Typical amino protecting groups are described in Greene at pages 315–385 and include Carbamates (methyl and ethyl, 9-fluorenylmethyl, 9(2-sulfo)fluoroenylmethyl, 9-(2, 7-dibromo)fluorenylmethyl, 2,7-di-t-buthyl-[9-(10,10-dioxo-10,10,10,10-tetrahydrothioxanthyl)]methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N—N Derivatives (N-nitro, N-nitroso, N-oxide); N—P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N—Si Derivatives; N—S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)$R^3$ or —N=$CR^4N(R^3)_2$.

Exemplary Compounds of the Invention

By way of example and not limitation, embodiment compounds are named below in tabular format (Table 5). Generally, each compound is depicted as a substituted nucleus in which the nucleus is designated by capital letter (s) and each substituent is designated in order by lower case letter or number. Table 1 is a schedule of nuclei which differ principally by the position and presence or absence of ring unsaturation, the stereochemistry of the ring substituents, the size of the ring and substitution at the 2 and 3 positions. Each nucleus is given a numerical designation from Table 1, and this designation appears first in each compound name. Similarly, Tables 2, 3 and 4 list the selected Z, B, $R^{1a}$ and $R^{1b}$ substituents, again by letter or number designation. $R^{1c}$, $R^{1d}$ and $R^{1e}$, if not shown herein, are H or bonds as dictated by valence. Accordingly, each named compound will be depicted by a number followed by upper and lower case letters designating the Z and B substitutents and, as appropriate, one or two more numbers designating the $R^{1a}$ and $R^{1b}$ substituents. $R^{1a}$ is H in structures 19–26. Thus, structure (28), scheme 2, is represented by 20.A.c.12 or 26.A.c.12 and compound (30), scheme 2, is represented by 9.A.c.12, where B=cytosine.

TABLE 1

Nucleus Structures

TABLE 1-continued

Nucleus Structures

TABLE 1-continued

Nucleus Structures

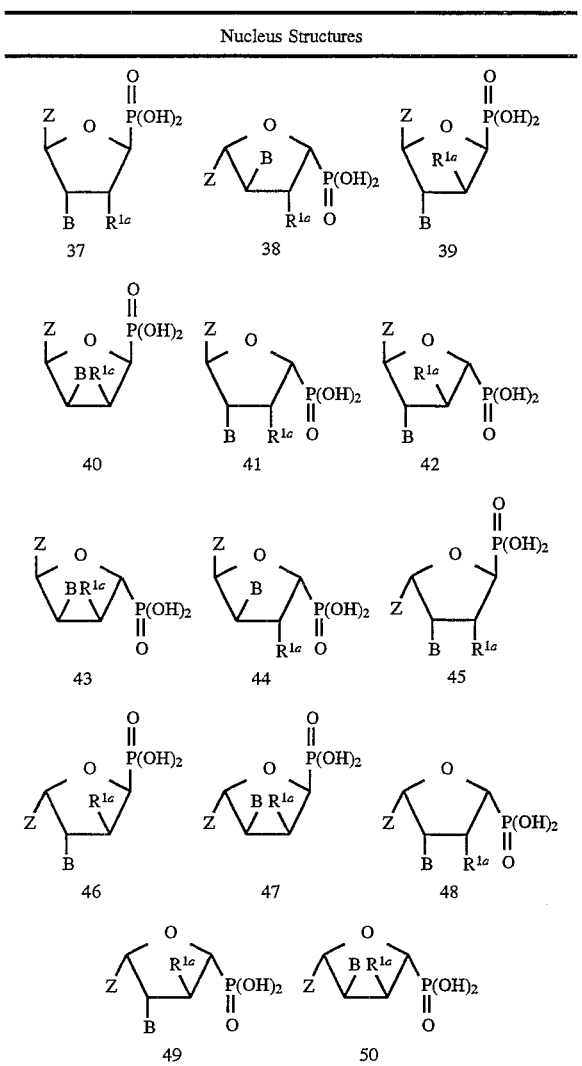

TABLE 2

| | Group Z |
|---|---|
| A. | $CH_2OH$ |
| B. | $CH_3$ |
| C. | $CH_2F$ |
| D. | H |
| E. | $CH_2OCH(CH_3)_2$ |
| F. | $CH_2OC(O)CH_2CH_3$ |
| G. | $CH_2N_3$ |
| H. | $CH=CH_2$ |
| I. | $C\equiv CH$ |

TABLE 3

| | Group B |
|---|---|
| a. | adenin-9-yl |
| b. | guanin-9-yl |
| c. | cytosin-1-yl |
| d. | thymin-1-yl |
| e. | 2,6-diaminopurin-9-yl |
| f. | 5-fluorocytosin-1-yl |
| g. | 2-aminopurin-9-yl |
| h. | 3-deazaadenin-9-yl |
| i. | 8-azaadenin-9-yl |
| j. | 5-iodocytosin-1-yl |
| k. | 7-deazaguanin-9-yl |
| l. | 5-chlorocytosin-1-yl |

TABLE 4

| | Groups $R^{1a}$ and $R^{1b}$ |
|---|---|
| 1. | OH |
| 2. | H |
| 3. | F |
| 4. | $OCH(CH_3)_2$ |
| 5. | $OC(O)CH_3$ |
| 6. | $CH_3$ |
| 7. | $CH_2N_3$ |
| 8. | $N_3$ |
| 9. | CN |
| 10. | $CH_2OH$ |

TABLE 5

Key: Nucleus. Group Z. Group B. Group $R^{1a}$. Group $R^{1b}$.
Saturated Pyrans 01.A.a.1.1; 01.A.a.1.2; 01.A.a.1.3; 01.A.a.2.1; 01.A.a.2.2; 01.A.a.2.3; 01.A.a.3.1;
01.A.a.3.2; 01.A.a.3.3; 01.A.b.1.1; 01.A.b.1.2; 01.A.b.1.3; 01.A.b.2.1; 01.A.b.2.2;
01.A.b.2.3; 01.A.b.3.1; 01.A.b.3.2; 01.A.b.3.3; 01.A.c.1.1; 01.A.c.1.2; 01.A.c.1.3;
01.A.c.2.1; 01.A.c.2.2; 01.A.c.2.3; 01.A.c.3.1; 01.A.c.3.2; 01.A.c.3.3; 01.A.d.1.1;
01.A.d.1.2; 01.A.d.1.3; 01.A.d.2.1; 01.A.d.2.2; 01.A.d.2.3; 01.A.d.3.1; 01.A.d.3.2;
01.A.d.3.3; 01.A.e.1.1; 01.A.e.1.2; 01.A.e.1.3; 01.A.e.2.1; 01.A.e.2.2; 01.A.e.2.3;
01.A.e.3.1; 01.A.e.3.2; 01.A.e.3.3; 01.A.f.1.1; 01.A.f.1.2; 01.A.f.1.3; 01.A.f.2.1;
01.A.f.2.2; 01.A.f.2.3; 01.A.f.3.1; 01.A.f.3.2; 01.A.f.3.3; 01.B.a.1.1; 01.B.a.1.2;
01.B.a.1.3; 01.B.a.2.1; 01.B.a.2.2; 01.B.a.2.3; 01.B.a.3.1; 01.B.a.3.2; 01.B.a.3.3;
01.B.b.1.1; 01.B.b.1.2; 01.B.b.1.3; 01.B.b.2.1; 01.B.b.2.2; 01.B.b.2.3; 01.B.b.3.1;
01.B.b.3.2; 01.B.b.3.3; 01.B.c.1.1; 01.B.c.1.2; 01.B.c.1.3; 01.B.c.2.1; 01.B.c.2.2;
01.B.c.2.3; 01.B.c.3.1; 01.B.c.3.2; 01.B.c.3.3; 01.B.d.1.1; 01.B.d.1.2; 01.B.d.1.3;
01.B.d.2.1; 01.B.d.2.2; 01.B.d.2.3; 01.B.d.3.1; 01.B.d.3.2; 01.B.d.3.3; 01.B.e.1.1;
01.B.e.1.2; 01.B.e.1.3; 01.B.e.2.1; 01.B.e.2.2; 01.B.e.2.3; 01.B.e.3.1; 01.B.e.3.2;
01.B.e.3.3; 01.B.f.1.1; 01.B.f.1.2; 01.B.f.1.3; 01.B.f.2.1; 01.B.f.2.2; 01.B.f.2.3; 01.B.f.3.1;
01.B.f.3.2; 01.B.f.3.3; 01.C.a.1.1; 01.C.a.1.2; 01.C.a.1.3; 01.C.a.2.1; 01.C.a.2.2;
01.C.a.2.3; 01.C.a.3.1; 01.C.a.3.2; 01.C.a.3.3; 01.C.b.1.1; 01.C.b.1.2; 01.C.b.1.3;
01.C.b.2.1; 01.C.b.2.2; 01.C.b.2.3; 01.C.b.3.1; 01.C.b.3.2; 01.C.b.3.3; 01.C.c.1.1;
01.C.c.1.2; 01.C.c.1.3; 01.C.c.2.1; 01.C.c.2.2; 01.C.c.2.3; 01.C.c.3.1; 01.C.c.3.2;
01.C.c.3.3; 01.C.d.1.1; 01.C.d.1.2; 01.C.d.1.3; 01.C.d.2.1; 01.C.d.2.2; 01.C.d.2.3;

TABLE 5-continued

Key: Nucleus. Group Z. Group B. Group $R^{1a}$. Group $R^{1b}$.
Saturated Pyrans 01.C.d.3.1; 01.C.d.3.2; 01.C.d.3.3; 01.C.e.1.1; 01.C.e.1.2; 01.C.e.1.3; 01.C.e.2.1;
01.C.e.2.2; 01.C.e.2.3; 01.C.e.3.1; 01.C.e.3.2; 01.C.e.3.3; 01.C.f.1.1; 01.C.f.1.2;
01.C.f.1.3; 01.C.f.2.1; 01.C.f.2.2; 01.C.f.2.3; 01.C.f.3.1; 01.C.f.3.2; 01.C.f.3.3; 01.D.a.1.1;
01.D.a.1.2; 01.D.a.1.3; 01.D.a.2.1; 01.D.a.2.2; 01.D.a.2.3; 01.D.a.3.1; 01.D.a.3.2;
01.D.a.3.3; 01.D.b.1.1; 01.D.b.1.2; 01.D.b.1.3; 01.D.b.2.1; 01.D.b.2.2; 01.D.b.2.3;
01.D.b.3.1; 01.D.b.3.2; 01.D.b.3.3; 01.D.c.1.1; 01.D.c.1.2; 01.D.c.1.3; 01.D.c.2.1;
01.D.c.2.2; 01.D.c.2.3; 01.D.c.3.1; 01.D.c.3.2; 01.D.c.3.3; 01.D.d.1.1; 01.D.d.1.2;
01.D.d.1.3; 01.D.d.2.1; 01.D.d.2.2; 01.D.d.2.3; 01.D.d.3.1; 01.D.d.3.2; 01.D.d.3.3;
01.D.e.1.1; 01.D.e.1.2; 01.D.e.1.3; 01.D.e.2.1; 01.D.e.2.2; 01.D.e.2.3; 01.D.e.3.1;
01.D.e.3.2; 01.D.e.3.3; 01.D.f.1.1; 01.D.f.1.2; 01.D.f.1.3; 01.D.f.2.1; 01.D.f.2.2;
01.D.f.2.3; 01.D.f.3.1; 01.D.f.3.2; 01.D.f.3.3; 02.A.a.1.1; 02.A.a.1.2; 02.A.a.1.3;
02.A.a.2.1; 02.A.a.2.2; 02.A.a.2.3; 02.A.a.3.1; 02.A.a.3.2; 02.A.a.3.3; 02.A.b.1.1;
02.A.b.1.2; 02.A.b.1.3; 02.A.b.2.1; 02.A.b.2.2; 02.A.b.2.3; 02.A.b.3.1; 02.A.b.3.2;
02.A.b.3.3; 02.A.c.1.1; 02.A.c.1.2; 02.A.c.1.3; 02.A.c.2.1; 02.A.c.2.2; 02.A.c.2.3;
02.A.c.3.1; 02.A.c.3.2; 02.A.c.3.3; 02.A.d.1.1; 02.A.d.1.2; 02.A.d.1.3; 02.A.d.2.1;
02.A.d.2.2; 02.A.d.2.3; 02.A.d.3.1; 02.A.d.3.2; 02.A.d.3.3; 02.A.e.1.1; 02.A.e.1.2;
02.A.e.1.3; 02.A.e.2.1; 02.A.e.2.2; 02.A.e.2.3; 02.A.e.3.1; 02.A.e.3.2; 02.A.e.3.3;
02.A.f.1.1; 02.A.f.1.2; 02.A.f.1.3; 02.A.f.2.1; 02.A.f.2.2; 02.A.f.2.3; 02.A.f.3.1;
02.A.f.3.2; 02.A.f.3.3; 02.B.a.1.1; 02.B.a.1.2; 02.B.a.1.3; 02.B.a.2.1; 02.B.a.2.2;
02.B.a.2.3; 02.B.a.3.1; 02.B.a.3.2; 02.B.a.3.3; 02.B.b.1.1; 02.B.b.1.2; 02.B.b.1.3;
02.B.b.2.1; 02.B.b.2.2; 02.B.b.2.3; 02.B.b.3.1; 02.B.b.3.2; 02.B.b.3.3; 02.B.c.1.1;
02.B.c.1.2; 02.B.c.1.3; 02.B.c.2.1; 02.B.c.2.2; 02.B.c.2.3; 02.B.c.3.1; 02.B.c.3.2;
02.B.c.3.3; 02.B.d.1.1; 02.B.d.1.2; 02.B.d.1.3; 02.B.d.2.1; 02.B.d.2.2; 02.B.d.2.3;
02.B.d.3.1; 02.B.d.3.2; 02.B.d.3.3; 02.B.e.1.1; 02.B.e.1.2; 02.B.e.1.3; 02.B.e.2.1;
02.B.e.2.2; 02.B.e.2.3; 02.B.e.3.1; 02.B.e.3.2; 02.B.e.3.3; 02.B.f.1.1; 02.B.f.1.2;
02.B.f.1.3; 02.B.f.2.1; 02.B.f.2.2; 02.B.f.2.3; 02.B.f.3.1; 02.B.f.3.2; 02.B.f.3.3; 02.C.a.1.1;
02.C.a.1.2; 02.C.a.1.3; 02.C.a.2.1; 02.C.a.2.2; 02.C.a.2.3; 02.C.a.3.1; 02.C.a.3.2;
02.C.a.3.3; 02.C.b.1.1; 02.C.b.1.2; 02.C.b.1.3; 02.C.b.2.1; 02.C.b.2.2; 02.C.b.2.3;
02.C.b.3.1; 02.C.b.3.2; 02.C.b.3.3; 02.C.c.1.1; 02.C.c.1.2; 02.C.c.1.3; 02.C.c.2.1;
02.C.c.2.2; 02.C.c.2.3; 02.C.c.3.1; 02.C.c.3.2; 02.C.c.3.3; 02.C.d.1.1; 02.C.d.1.2;
02.C.d.1.3; 02.C.d.2.1; 02.C.d.2.2; 02.C.d.2.3; 02.C.d.3.1; 02.C.d.3.2; 02.C.d.3.3;
02.C.e.1.1; 02.C.e.1.2; 02.C.e.1.3; 02.C.e.2.1; 02.C.e.2.2; 02.C.e.2.3; 02.C.e.3.1;
02.C.e.3.2; 02.C.e.3.3; 02.C.f.1.1; 02.C.f.1.2; 02.C.f.1.3; 02.C.f.2.1; 02.C.f.2.2;
02.C.f.2.3; 02.C.f.3.1; 02.C.f.3.2; 02.C.f.3.3; 02.D.a.1.1; 02.D.a.1.2; 02.D.a.1.3;
02.D.a.2.1; 02.D.a.2.2; 02.D.a.2.3; 02.D.a.3.1; 02.D.a.3.2; 02.D.a.3.3; 02.D.b.1.1;
02.D.b.1.2; 02.D.b.1.3; 02.D.b.2.1; 02.D.b.2.2; 02.D.b.2.3; 02.D.b.3.1; 02.D.b.3.2;
02.D.b.3.3; 02.D.c.1.1; 02.D.c.1.2; 02.D.c.1.3; 02.D.c.2.1; 02.D.c.2.2; 02.D.c.2.3;
02.D.c.3.1; 02.D.c.3.2; 02.D.c.3.3; 02.D.d.1.1; 02.D.d.1.2; 02.D.d.1.3; 02.D.d.2.1;
02.D.d.2.2; 02.D.d.2.3; 02.D.d.3.1; 02.D.d.3.2; 02.D.d.3.3; 02.D.e.1.1; 02.D.e.1.2;
02.D.e.1.3; 02.D.e.2.1; 02.D.e.2.2; 02.D.e.2.3; 02.D.e.3.1; 02.D.e.3.2; 02.D.e.3.3;
02.D.f.1.1; 02.D.f.1.2; 02.D.f.1.3; 02.D.f.2.1; 02.D.f.2.2; 02.D.f.2.3; 02.D.f.3.1;
02.D.f.3.2; 02.D.f.3.3; 03.A.a.1.1; 03.A.a.1.2; 03.A.a.1.3; 03.A.a.2.1; 03.A.a.2.2;
03.A.a.2.3; 03.A.a.3.1; 03.A.a.3.2; 03.A.a.3.3; 03.A.b.1.1; 03.A.b.1.2; 03.A.b.1.3;
03.A.b.2.1; 03.A.b.2.2; 03.A.b.2.3; 03.A.b.3.1; 03.A.b.3.2; 03.A.b.3.3; 03.A.c.1.1;
03.A.c.1.2; 03.A.c.1.3; 03.A.c.2.1; 03.A.c.2.2; 03.A.c.2.3; 03.A.c.3.1; 03.A.c.3.2;
03.A.c.3.3; 03.A.d.1.1; 03.A.d.1.2; 03.A.d.1.3; 03.A.d.2.1; 03.A.d.2.2; 03.A.d.2.3;
03.A.d.3.1; 03.A.d.3.2; 03.A.d.3.3; 03.A.e.1.1; 03.A.e.1.2; 03.A.e.1.3; 03.A.e.2.1;
03.A.e.2.2; 03.A.e.2.3; 03.A.e.3.1; 03.A.e.3.2; 03.A.e.3.3; 03.A.f.1.1; 03.A.f.1.2;
03.A.f.1.3; 03.A.f.2.1; 03.A.f.2.2; 03.A.f.2.3; 03.A.f.3.1; 03.A.f.3.2; 03.A.f.3.3;
03.B.a.1.1; 03.B.a.1.2; 03.B.a.1.3; 03.B.a.2.1; 03.B.a.2.2; 03.B.a.2.3; 03.B.a.3.1;
03.B.a.3.2; 03.B.a.3.3; 03.B.b.1.1; 03.B.b.1.2; 03.B.b.1.3; 03.B.b.2.1; 03.B.b.2.2;
03.B.b.2.3; 03.B.b.3.1; 03.B.b.3.2; 03.B.b.3.3; 03.B.c.1.1; 03.B.c.1.2; 03.B.c.1.3;
03.B.c.2.1; 03.B.c.2.2; 03.B.c.2.3; 03.B.c.3.1; 03.B.c.3.2; 03.B.c.3.3; 03.B.d.1.1;
03.B.d.1.2; 03.B.d.1.3; 03.B.d.2.1; 03.B.d.2.2; 03.B.d.2.3; 03.B.d.3.1; 03.B.d.3.2;
03.B.d.3.3; 03.B.e.1.1; 03.B.e.1.2; 03.B.e.1.3; 03.B.e.2.1; 03.B.e.2.2; 03.B.e.2.3;
03.B.e.3.1; 03.B.e.3.2; 03.B.e.3.3; 03.B.f.1.1; 03.B.f.1.2; 03.B.f.1.3; 03.B.f.2.1;
03.B.f.2.2; 03.B.f.2.3; 03.B.f.3.1; 03.B.f.3.2; 03.B.f.3.3; 03.C.a.1.1; 03.C.a.1.2;
03.C.a.1.3; 03.C.a.2.1; 03.C.a.2.2; 03.C.a.2.3; 03.C.a.3.1; 03.C.a.3.2; 03.C.a.3.3;
03.C.b.1.1; 03.C.b.1.2; 03.C.b.1.3; 03.C.b.2.1; 03.C.b.2.2; 03.C.b.2.3; 03.C.b.3.1;
03.C.b.3.2; 03.C.b.3.3; 03.C.c.1.1; 03.C.c.1.2; 03.C.c.1.3; 03.C.c.2.1; 03.C.c.2.2;
03.C.c.2.3; 03.C.c.3.1; 03.C.c.3.2; 03.C.c.3.3; 03.C.d.1.1; 03.C.d.1.3;
03.C.d.2.1; 03.C.d.2.2; 03.C.d.2.3; 03.C.d.3.1; 03.C.d.3.2; 03.C.d.3.3; 03.C.e.1.1;
03.C.e.1.2; 03.C.e.1.3; 03.C.e.2.1; 03.C.e.2.2; 03.C.e.2.3; 03.C.e.3.1; 03.C.e.3.2;
03.C.e.3.3; 03.C.f.1.1; 03.C.f.1.2; 03.C.f.1.3; 03.C.f.2.1; 03.C.f.2.2; 03.C.f.2.3; 03.C.f.3.1;
03.C.f.3.2; 03.C.f.3.3; 03.D.a.1.1; 03.D.a.1.2; 03.D.a.1.3; 03.D.a.2.1; 03.D.a.2.2;
03.D.a.2.3; 03.D.a.3.1; 03.D.a.3.2; 03.D.a.3.3; 03.D.b.1.1; 03.D.b.1.2; 03.D.b.1.3;
03.D.b.2.1; 03.D.b.2.2; 03.D.b.2.3; 03.D.b.3.1; 03.D.b.3.2; 03.D.b.3.3; 03.D.c.1.1;
03.D.c.1.2; 03.D.c.1.3; 03.D.c.2.1; 03.D.c.2.2; 03.D.c.2.3; 03.D.c.3.1; 03.D.c.3.2;
03.D.c.3.3; 03.D.d.1.1; 03.D.d.1.2; 03.D.d.1.3; 03.D.d.2.1; 03.D.d.2.2; 03.D.d.2.3;
03.D.d.3.1; 03.D.d.3.2; 03.D.d.3.3; 03.D.e.1.1; 03.D.e.1.2; 03.D.e.1.3; 03.D.e.2.1;
03.D.e.2.2; 03.D.e.2.3; 03.D.e.3.1; 03.D.e.3.2; 03.D.e.3.3; 03.D.f.1.1; 03.D.f.1.2;
03.D.f.1.3; 03.D.f.2.1; 03.D.f.2.2; 03.D.f.2.3; 03.D.f.3.1; 03.D.f.3.2; 03.D.f.3.3;
04.A.a.1.1; 04.A.a.1.2; 04.A.a.1.3; 04.A.a.2.1; 04.A.a.2.2; 04.A.a.2.3; 04.A.a.3.1;
04.A.a.3.2; 04.A.a.3.3; 04.A.b.1.1; 04.A.b.1.2; 04.A.b.1.3; 04.A.b.2.1; 04.A.b.2.2;
04.A.b.2.3; 04.A.b.3.1; 04.A.b.3.2; 04.A.b.3.3; 04.A.c.1.1; 04.A.c.1.2; 04.A.c.1.3;
04.A.c.2.1; 04.A.c.2.2; 04.A.c.2.3; 04.A.c.3.1; 04.A.c.3.2; 04.A.c.3.3; 04.A.d.1.1;

TABLE 5-continued

Key: Nucleus. Group Z. Group B. Group R$^{1a}$. Group R$^{1b.}$
Saturated Pyrans 04.A.d.1.2; 04.A.d.1.3; 04.A.d.2.1; 04.A.d.2.2; 04.A.d.2.3; 04.A.d.3.1; 04.A.d.3.2;
04.A.d.3.3; 04.A.e.1.1; 04.A.e.1.2; 04.A.e.1.3; 04.A.e.2.1; 04.A.e.2.2; 04.A.e.2.3;
04.A.e.3.1; 04.A.e.3.2; 04.A.e.3.3; 04.A.f.1.1; 04.A.f.1.2; 04.A.f.1.3; 04.A.f.2.1;
04.A.f.2.2; 04.A.f.2.3; 04.A.f.3.1; 04.A.f.3.2; 04.A.f.3.3; 04.B.a.1.1; 04.B.a.1.2;
04.B.a.1.3; 04.B.a.2.1; 04.B.a.2.2; 04.B.a.2.3; 04.B.a.3.1; 04.B.a.3.2; 04.B.a.3.3;
04.B.b.1.1; 04.B.b.1.2; 04.B.b.1.3; 04.B.b.2.1; 04.B.b.2.2; 04.B.b.2.3; 04.B.b.3.1;
04.B.b.3.2; 04.B.b.3.3; 04.B.c.1.1; 04.B.c.1.2; 04.B.c.1.3; 04.B.c.2.1; 04.B.c.2.2;
04.B.c.2.3; 04.B.c.3.1; 04.B.c.3.2; 04.B.c.3.3; 04.B.d.1.1; 04.B.d.1.2; 04.B.d.1.3;
04.B.d.2.1; 04.B.d.2.2; 04.B.d.2.3; 04.B.d.3.1; 04.B.d.3.2; 04.B.d.3.3; 04.B.e.1.1;
04.B.e.1.2; 04.B.e.1.3; 04.B.e.2.1; 04.B.e.2.2; 04.B.e.2.3; 04.B.e.3.1; 04.B.e.3.2;
04.B.e.3.3; 04.B.f.1.1; 04.B.f.1.2; 04.B.f.1.3; 04.B.f.2.1; 04.B.f.2.2; 04.B.f.2.3; 04.B.f.3.1;
04.B.f.3.2; 04.B.f.3.3; 04.C.a.1.1; 04.C.a.1.2; 04.C.a.1.3; 04.C.a.2.1; 04.C.a.2.2;
04.C.a.2.3; 04.C.a.3.1; 04.C.a.3.2; 04.C.a.3.3; 04.C.b.1.1; 04.C.b.1.2; 04.C.b.1.3;
04.C.b.2.1; 04.C.b.2.2; 04.C.b.2.3; 04.C.b.3.1; 04.C.b.3.2; 04.C.b.3.3; 04.C.c.1.1;
04.C.c.1.2; 04.C.c.1.3; 04.C.c.2.1; 04.C.c.2.2; 04.C.c.2.3; 04.C.c.3.1; 04.C.c.3.2;
04.C.c.3.3; 04.C.d.1.1; 04.C.d.1.2; 04.C.d.1.3; 04.C.d.2.1; 04.C.d.2.2; 04.C.d.2.3;
04.C.d.3.1; 04.C.d.3.2; 04.C.d.3.3; 04.C.e.1.1; 04.C.e.1.2; 04.C.e.1.3; 04.C.e.2.1;
04.C.e.2.2; 04.C.e.2.3; 04.C.e.3.1; 04.C.e.3.2; 04.C.e.3.3; 04.C.f.1.1; 04.C.f.1.2;
04.C.f.1.3; 04.C.f.2.1; 04.C.f.2.2; 04.C.f.2.3; 04.C.f.3.1; 04.C.f.3.2; 04.C.f.3.3; 04.D.a.1.1;
04.D.a.1.2; 04.D.a.1.3; 04.D.a.2.1; 04.D.a.2.2; 04.D.a.2.3; 04.D.a.3.1; 04.D.a.3.2;
04.D.a.3.3; 04.D.b.1.1; 04.D.b.1.2; 04.D.b.1.3; 04.D.b.2.1; 04.D.b.2.2; 04.D.b.2.3;
04.D.b.3.1; 04.D.b.3.2; 04.D.b.3.3; 04.D.c.1.1; 04.D.c.1.2; 04.D.c.1.3; 04.D.c.2.1;
04.D.c.2.2; 04.D.c.2.3; 04.D.c.3.1; 04.D.c.3.2; 04.D.c.3.3; 04.D.d.1.1; 04.D.d.1.2;
04.D.d.1.3; 04.D.d.2.1; 04.D.d.2.2; 04.D.d.2.3; 04.D.d.3.1; 04.D.d.3.2; 04.D.d.3.3;
04.D.e.1.1; 04.D.e.1.2; 04.D.e.1.3; 04.D.e.2.1; 04.D.e.2.2; 04.D.e.2.3; 04.D.e.3.1;
04.D.e.3.2; 04.D.e.3.3; 04.D.f.1.1; 04.D.f.1.2; 04.D.f.1.3; 04.D.f.2.1; 04.D.f.2.2;
04.D.f.2.3; 04.D.f.3.1; 04.D.f.3.2; 04.D.f.3.3; 18.A.a.1.1; 18.A.a.1.2; 18.A.a.1.3;
18.A.a.2.1; 18.A.a.2.2; 18.A.a.2.3; 18.A.a.3.1; 18.A.a.3.2; 18.A.a.3.3; 18.A.b.1.1;
18.A.b.1.2; 18.A.b.1.3; 18.A.b.2.1; 18.A.b.2.2; 18.A.b.2.3; 18.A.b.3.1; 18.A.b.3.2;
18.A.b.3.3; 18.A.c.1.1; 18.A.c.1.2; 18.A.c.1.3; 18.A.c.2.1; 18.A.c.2.2; 18.A.c.2.3;
18.A.c.3.1; 18.A.c.3.2; 18.A.c.3.3; 18.A.d.1.1; 18.A.d.1.2; 18.A.d.1.3; 18.A.d.2.1;
18.A.d.2.2; 18.A.d.2.3; 18.A.d.3.1; 18.A.d.3.2; 18.A.d.3.3; 18.A.e.1.1; 18.A.e.1.2;
18.A.e.1.3; 18.A.e.2.1; 18.A.e.2.2; 18.A.e.2.3; 18.A.e.3.1; 18.A.e.3.2; 18.A.e.3.3;
18.A.f.1.1; 18.A.f.1.2; 18.A.f.1.3; 18.A.f.2.1; 18.A.f.2.2; 18.A.f.2.3; 18.A.f.3.1;
18.A.f.3.2; 18.A.f.3.3; 18.B.a.1.1; 18.B.a.1.2; 18.B.a.1.3; 18.B.a.2.1; 18.B.a.2.2;
18.B.a.2.3; 18.B.a.3.1; 18.B.a.3.2; 18.B.a.3.3; 18.B.b.1.1; 18.B.b.1.2; 18.B.b.1.3;
18.B.b.2.1; 18.B.b.2.2; 18.B.b.2.3; 18.B.b.3.1; 18.B.b.3.2; 18.B.b.3.3; 18.B.c.1.1;
18.B.c.1.2; 18.B.c.1.3; 18.B.c.2.1; 18.B.c.2.2; 18.B.c.2.3; 18.B.c.3.1; 18.B.c.3.2;
18.B.c.3.3; 18.B.d.1.1; 18.B.d.1.2; 18.B.d.1.3; 18.B.d.2.1; 18.B.d.2.2; 18.B.d.2.3;
18.B.d.3.1; 18.B.d.3.2; 18.B.d.3.3; 18.B.e.1.1; 18.B.e.1.2; 18.B.e.1.3; 18.B.e.2.1;
18.B.e.2.2; 18.B.e.2.3; 18.B.e.3.1; 18.B.e.3.2; 18.B.e.3.3; 18.B.f.1.1; 18.B.f.1.2;
18.B.f.1.3; 18.B.f 2.1; 18.B.f.2.2; 18.B.f.2.3; 18.B.f.3.1; 18.B.f.3.2; 18.B.f.3.3; 18.C.a.1.1;
18.C.a.1.2; 18.C.a.1.3; 18.C.a.2.1; 18.C.a.2.2; 18.C.a.2.3; 18.C.a.3.1; 18.C.a.3.2;
18.C.a.3.3; 18.C.b.1.1; 18.C.b.1.2; 18.C.b.1.3; 18.C.b.2.1; 18.C.b.2.2; 18.C.b.2.3;
18.C.b.3.1; 18.C.b.3.2; 18.C.b.3.3; 18.C.c.1.1; 18.C.c.1.2; 18.C.c.1.3; 18.C.c.2.1;
18.C.c.2.2; 18.C.c.2.3; 18.C.c.3.1; 18.C.c.3.2; 18.C.c.3.3; 18.C.d.1.1; 18.C.d.1.2;
18.C.d.1.3; 18.C.d.2.1; 18.C.d.2.2; 18.C.d.2.3; 18.C.d.3.1; 18.C.d.3.2; 18.C.d.3.3;
18.C.e.1.1; 18.C.e.1.2; 18.C.e.1.3; 18.C.e.2.1; 18.C.e.2.2; 18.C.e.2.3; 18.C.e.3.1;
18.C.e.3.2; 18.C.e.3.3; 18.C.f.1.1; 18.C.f.1.2; 18.C.f.1.3; 18.C.f.2.1; 18.C.f.2.2;
18.C.f.2.3; 18.C.f.3.1; 18.C.f.3.2; 18.C.f.3.3; 18.D.a.1.1; 18.D.a.1.2; 18.D.a.1.3;
18.D.a.2.1; 18.D.a.2.2; 18.D.a.2.3; 18.D.a.3.1; 18.D.a.3.2; 18.D.a.3.3; 18.D.b.1.1;
18.D.b.1.2; 18.D.b.1.3; 18.D.b.2.1; 18.D.b.2.2; 18.D.b.2.3; 18.D.b.3.1; 18.D.b.3.2;
18.D.b.3.3; 18.D.c.1.1; 18.D.c.1.2; 18.D.c.1.3; 18.D.c.2.1; 18.D.c.2.2; 18.D.c.2.3;
18.D.c.3.1; 18.D.c.3.2; 18.D.c.3.3; 18.D.d.1.1; 18.D.d.1.2; 18.D.d.1.3; 18.D.d.2.1;
18.D.d.2.2; 18.D.d.2.3; 18.D.d.3.1; 18.D.d.3.2; 18.D.d.3.3; 18.D.e.1.1; 18.D.e.1.2;
18.D.e.1.3; 18.D.e.2.1; 18.D.e.2.2; 18.D.e.2.3; 18.D.e.3.1; 18.D.e.3.2; 18.D.e.3.3;
18.D.f.1.1; 18.D.f.1.2; 18.D.f.1.3; 18.D.f.2.1; 18.D.f.2.2; 18.D.f.2.3; 18.D.f.3.1;
18.D.f.3.2; 18.D.f.3.3; 27.A.a.1.1; 27.A.a.1.2; 27.A.a.1.3; 27.A.a.2.1; 27.A.a.2.2;
27.A.a.2.3; 27.A.a.3.1; 27.A.a.3.2; 27.A.a.3.3; 27.A.b.1.1; 27.A.b.1.2; 27.A.b.1.3;
27.A.b.2.1; 27.A.b.2.2; 27.A.b.2.3; 27.A.b.3.1; 27.A.b.3.2; 27.A.b.3.3; 27.A.c.1.1;
27.A.c.1.2; 27.A.c.1.3; 27.A.c.2.1; 27.A.c.2.2; 27.A.c.2.3; 27.A.c.3.1; 27.A.c.3.2;
27.A.c.3.3; 27.A.d.1.1; 27.A.d.1.2; 27.A.d.1.3; 27.A.d.2.1; 27.A.d.2.2; 27.A.d.2.3;
27.A.d.3.1; 27.A.d.3.2; 27.A.d.3.3; 27.A.e.1.1; 27.A.e.1.2; 27.A.e.1.3; 27.A.e.2.1;
27.A.e.2.2; 27.A.e.2.3; 27.A.e.3.1; 27.A.e.3.2; 27.A.e.3.3; 27.A.f.1.1; 27.A.f.1.2;
27.A.f.1.3; 27.A.f.2.1; 27.A.f.2.2; 27.A.f.2.3; 27.A.f.3.1; 27.A.f.3.2; 27.A.f.3.3;
27.B.a.1.1; 27.B.a.1.2; 27.B.a.1.3; 27.B.a.2.1; 27.B.a.2.2; 27.B.a.2.3; 27.B.a.3.1;
27.B.a.3.2; 27.B.a.3.3; 27.B.b.1.1; 27.B.b.1.2; 27.B.b.1.3; 27.B.b.2.1; 27.B.b.2.2;
27.B.b.2.3; 27.B.b.3.1; 27.B.b.3.2; 27.B.b.3.3; 27.B.c.1.1; 27.B.c.1.2; 27.B.c.1.3;
27.B.c.2.1; 27.B.c.2.2; 27.B.c.2.3; 27.B.c.3.1; 27.B.c.3.2; 27.B.c.3.3; 27.B.d.1.1;
27.B.d.1.2; 27.B.d.1.3; 27.B.d.2.1; 27.B.d.2.2; 27.B.d.2.3; 27.B.d.3.1; 27.B.d.3.2;
27.B.d.3.3; 27.B.e.1.1; 27.B.e.1.2; 27.B.e.1.3; 27.B.e.2.1; 27.B.e.2.2; 27.B.e.2.3;
27.B.e.3.1; 27.B.e.3.2; 27.B.e.3.3; 27.B.f.1.1; 27.B.f.1.2; 27.B.f.1.3; 27.B.f.2.1;
27.B.f.2.2; 27.B.f.2.3; 27.B.f.3.1; 27.B.f.3.2; 27.B.f.3.3; 27.C.a.1.1; 27.C.a.1.2;
27.C.a.1.3; 27.C.a.2.1; 27.C.a.2.2; 27.C.a.2.3; 27.C.a.3.1; 27.C.a.3.2; 27.C.a.3.3;
27.C.b.1.1; 27.C.b.1.2; 27.C.b.1.3; 27.C.b.2.1; 27.C.b.2.2; 27.C.b.2.3; 27.C.b.3.1;
27.C.b.3.2; 27.C.b.3.3; 27.C.c.1.1; 27.C.c.1.2; 27.C.c.1.3; 27.C.c.2.1; 27.C.c.2.2;

TABLE 5-continued

Key: Nucleus. Group Z. Group B. Group $R^{1a}$. Group $R^{1b}$.
Saturated Pyrans 27.C.c.2.3; 27.C.c.3.1; 27.C.c.3.2; 27.C.c.3.3; 27.C.d.1.1; 27.C.d.1.2; 27.C.d.1.3;
27.C.d.2.1; 27.C.d.2.2; 27.C.d.2.3; 27.C.d.3.1; 27.C.d.3.2; 27.C.d.3.3; 27.C.e.1.1;
27.C.e.1.2; 27.C.e.1.3; 27.C.e.2.1; 27.C.e.2.2; 27.C.e.2.3; 27.C.e.3.1; 27.C.e.3.2;
27.C.e.3.3; 27.C.f.1.1; 27.C.f.1.2; 27.C.f.1.3; 27.C.f.2.1; 27.C.f.2.2; 27.C.f.2.3; 27.C.f.3.1;
27.C.f.3.2; 27.C.f.3.3; 27.D.a.1.1; 27.D.a.1.2; 27.D.a.1.3; 27.D.a.2.1; 27.D.a.2.2;
27.D.a.2.3; 27.D.a.3.1; 27.D.a.3.2; 27.D.a.3.3; 27.D.b.1.1; 27.D.b.1.2; 27.D.b.1.3;
27.D.b.2.1; 27.D.b.2.2; 27.D.b.2.3; 27.D.b.3.1; 27.D.b.3.2; 27.D.b.3.3; 27.D.c.1.1;
27.D.c.1.2; 27.D.c.1.3; 27.D.c.2.1; 27.D.c.2.2; 27.D.c.2.3; 27.D.c.3.1; 27.D.c.3.2;
27.D.c.3.3; 27.D.d.1.1; 27.D.d.1.2; 27.D.d.1.3; 27.D.d.2.1; 27.D.d.2.2; 27.D.d.2.3;
27.D.d.3.1; 27.D.d.3.2; 27.D.d.3.3; 27.D.e.1.1; 27.D.e.1.2; 27.D.e.1.3; 27.D.e.2.1;
27.D.e.2.2; 27.D.e.2.3; 27.D.e.3.1; 27.D.e.3.2; 27.D.e.3.3; 27.D.f.1.1; 27.D.f.1.2;
27.D.f.1.3; 27.D.f.2.1; 27.D.f.2.2; 27.D.f.2.3; 27.D.f.3.1; 27.D.f.3.2; 27.D.f.3.3;
28.A.a.1.1; 28.A.a.1.2; 28.A.a.1.3; 28.A.a.2.1; 28.A.a.2.2; 28.A.a.2.3; 28.A.a.3.1;
28.A.a.3.2; 28.A.a.3.3; 28.A.b.1.1; 28.A.b.1.2; 28.A.b.1.3; 28.A.b.2.1; 28.A.b.2.2;
28.A.b.2.3; 28.A.b.3.1; 28.A.b.3.2; 28.A.b.3.3; 28.A.c.1.1; 28.A.c.1.2; 28.A.c.1.3;
28.A.c.2.1; 28.A.c.2.2; 28.A.c.2.3; 28.A.c.3.1; 28.A.c.3.2; 28.A.c.3.3; 28.A.d.1.1;
28.A.d.1.2; 28.A.d.1.3; 28.A.d.2.1; 28.A.d.2.2; 28.A.d.2.3; 28.A.d.3.1; 28.A.d.3.2;
28.A.d.3.3; 28.A.e.1.1; 28.A.e.1.2; 28.A.e.1.3; 28.A.e.2.1; 28.A.e.2.2; 28.A.e.2.3;
28.A.e.3.1; 28.A.e.3.2; 28.A.e.3.3; 28.A.f.1.1; 28.A.f.1.2; 28.A.f.1.3; 28.A.f.2.1;
28.A.f.2.2; 28.A.f.2.3; 28.A.f.3.1; 28.A.f.3.2; 28.A.f.3.3; 28.B.a.1.1; 28.B.a.1.2;
28.B.a.1.3; 28.B.a.2.1; 28.B.a.2.2; 28.B.a.2.3; 28.B.a.3.1; 28.B.a.3.2; 28.B.a.3.3;
28.B.b.1.1; 28.B.b.1.2; 28.B.b.1.3; 28.B.b.2.1; 28.B.b.2.2; 28.B.b.2.3; 28.B.b.3.1;
28.B.b.3.2; 28.B.b.3.3; 28.B.c.1.1; 28.B.c.1.2; 28.B.c.1.3; 28.B.c.2.1; 28.B.c.2.2;
28.B.c.2.3; 28.B.c.3.1; 28.B.c.3.2; 28.B.c.3.3; 28.B.d.1.1; 28.B.d.1.2; 28.B.d.1.3;
28.B.d.2.1; 28.B.d.2.2; 28.B.d.2.3; 28.B.d.3.1; 28.B.d.3.2; 28.B.d.3.3; 28.B.e.1.1;
28.B.e.1.2; 28.B.e.1.3; 28.B.e.2.1; 28.B.e.2.2; 28.B.e.2.3; 28.B.e.3.1; 28.B.e.3.2;
28.B.e.3.3; 28.B.f.1.1; 28.B.f.1.2; 28.B.f.1.3; 28.B.f.2.1; 28.B.f.2.2; 28.B.f.2.3; 28.B.f.3.1;
28.B.f.3.2; 28.B.f.3.3; 28.C.a.1.1; 28.C.a.1.2; 28.C.a.1.3; 28.C.a.2.1; 28.C.a.2.2;
28.C.a.2.3; 28.C.a.3.1; 28.C.a.3.2; 28.C.a.3.3; 28.C.b.1.1; 28.C.b.1.2; 28.C.b.1.3;
28.C.b.2.1; 28.C.b.2.2; 28.C.b.2.3; 28.C.b.3.1; 28.C.b.3.2; 28.C.b.3.3; 28.C.c.1.1;
28.C.c.1.2; 28.C.c.1.3; 28.C.c.2.1; 28.C.c.2.2; 28.C.c.2.3; 28.C.c.3.1; 28.C.c.3.2;
28.C.c.3.3; 28.C.d.1.1; 28.C.d.1.2; 28.C.d.1.3; 28.C.d.2.1; 28.C.d.2.2; 28.C.d.2.3;
28.C.d.3.1; 28.C.d.3.2; 28.C.d.3.3; 28.C.e.1.1; 28.C.e.1.2; 28.C.e.1.3; 28.C.e.2.1;
28.C.e.2.2; 28.C.e.2.3; 28.C.e.3.1; 28.C.e.3.2; 28.C.e.3.3; 28.C.f.1.1; 28.C.f.1.2;
28.C.f.1.3; 28.C.f.2.1; 28.C.f.2.2; 28.C.f.2.3; 28.C.f.3.1; 28.C.f.3.2; 28.C.f.3.3; 28.D.a.1.1;
28.D.a.1.2; 28.D.a.1.3; 28.D.a.2.1; 28.D.a.2.2; 28.D.a.2.3; 28.D.a.3.1; 28.D.a.3.2;
28.D.a.3.3; 28.D.b.1.1; 28.D.b.1.2; 28.D.b.1.3; 28.D.b.2.1; 28.D.b.2.2; 28.D.b.2.3;
28.D.b.3.1; 28.D.b.3.2; 28.D.b.3.3; 28.D.c.1.1; 28.D.c.1.2; 28.D.c.1.3; 28.D.c.2.1;
28.D.c.2.2; 28.D.c.2.3; 28.D.c.3.1; 28.D.c.3.2; 28.D.c.3.3; 28.D.d.1.1; 28.D.d.1.2;
28.D.d.1.3; 28.D.d.2.1; 28.D.d.2.2; 28.D.d.2.3; 28.D.d.3.1; 28.D.d.3.2; 28.D.d.3.3;
28.D.e.1.1; 28.D.e.1.2; 28.D.e.1.3; 28.D.e.2.1; 28.D.e.2.2; 28.D.e.2.3; 28.D.e.3.1;
28.D.e.3.2; 28.D.e.3.3; 28.D.f.1.1; 28.D.f.1.2; 28.D.f.1.3; 28.D.f.2.1; 28.D.f.2.2;
28.D.f.2.3; 28.D.f.3.1; 28.D.f.3.2; 28.D.f.3.3; 29.A.a.1.1; 29.A.a.1.2; 29.A.a.1.3;
29.A.a.2.1; 29.A.a.2.2; 29.A.a.2.3; 29.A.a.3.1; 29.A.a.3.2; 29.A.a.3.3; 29.A.b.1.1;
29.A.b.1.2; 29.A.b.1.3; 29.A.b.2.1; 29.A.b.2.2; 29.A.b.2.3; 29.A.b.3.1; 29.A.b.3.2;
29.A.b.3.3; 29.A.c.1.1; 29.A.c.1.2; 29.A.c.1.3; 29.A.c.2.1; 29.A.c.2.2; 29.A.c.2.3;
29.A.c.3.1; 29.A.c.3.2; 29.A.c.3.3; 29.A.d.1.1; 29.A.d.1.2; 29.A.d.1.3; 29.A.d.2.1;
29.A.d.2.2; 29.A.d.2.3; 29.A.d.3.1; 29.A.d.3.2; 29.A.d.3.3; 29.A.e.1.1; 29.A.e.1.2;
29.A.e.1.3; 29.A.e.2.1; 29.A.e.2.2; 29.A.e.2.3; 29.A.e.3.1; 29.A.e.3.2; 29.A.e.3.3;
29.A.f.1.1; 29.A.f.1.2; 29.A.f.1.3; 29.A.f.2.1; 29.A.f.2.2; 29.A.f.2.3; 29.A.f.3.1;
29.A.f.3.2; 29.A.f.3.3; 29.B.a.1.1; 29.B.a.1.2; 29.B.a.1.3; 29.B.a.2.1; 29.B.a.2.2;
29.B.a.2.3; 29.B.a.3.1; 29.B.a.3.2; 29.B.a.3.3; 29.B.b.1.1; 29.B.b.1.2; 29.B.b.1.3;
29.B.b.2.1; 29.B.b.2.2; 29.B.b.2.3; 29.B.b.3.1; 29.B.b.3.2; 29.B.b.3.3; 29.B.c.1.1;
29.B.c.1.2; 29.B.c.1.3; 29.B.c.2.1; 29.B.c.2.2; 29.B.c.2.3; 29.B.c.3.1; 29.B.c.3.2;
29.B.c.3.3; 29.B.d.1.1; 29.B.d.1.2; 29.B.d.1.3; 29.B.d.2.1; 29.B.d.2.2; 29.B.d.2.3;
29.B.d.3.1; 29.B.d.3.2; 29.B.d.3.3; 29.B.e.1.1; 29.B.e.1.2; 29.B.e.1.3; 29.B.e.2.1;
29.B.e.2.2; 29.B.e.2.3; 29.B.e.3.1; 29.B.e.3.2; 29.B.e.3.3; 29.B.f.1.1; 29.B.f.1.2;
29.B.f.1.3; 29.B.f.2.1; 29.B.f.2.2; 29.B.f.2.3; 29.B.f.3.1; 29.B.f.3.2; 29.B.f.3.3; 29.C.a.1.1;
29.C.a.1.2; 29.C.a.1.3; 29.C.a.2.1; 29.C.a.2.2; 29.C.a.2.3; 29.C.a.3.1; 29.C.a.3.2;
29.C.a.3.3; 29.C.b.1.1; 29.C.b.1.2; 29.C.b.1.3; 29.C.b.2.1; 29.C.b.2.2; 29.C.b.2.3;
29.C.b.3.1; 29.C.b.3.2; 29.C.b.3.3; 29.C.c.1.1; 29.C.c.1.2; 29.C.c.1.3; 29.C.c.2.1;
29.C.c.2.2; 29.C.c.2.3; 29.C.c.3.1; 29.C.c.3.2; 29.C.c.3.3; 29.C.d.1.1; 29.C.d.1.2;
29.C.d.1.3; 29.C.d.2.1; 29.C.d.2.2; 29.C.d.2.3; 29.C.d.3.1; 29.C.d.3.2; 29.C.d.3.3;
29.C.e.1.1; 29.C.e.1.2; 29.C.e.1.3; 29.C.e.2.1; 29.C.e.2.2; 29.C.e.2.3; 29.C.e.3.1;
29.C.e.3.2; 29.C.e.3.3; 29.C.f.1.1; 29.C.f.1.2; 29.C.f.1.3; 29.C.f.2.1; 29.C.f.2.2;
29.C.f.2.3; 29.C.f.3.1; 29.C.f.3.2; 29.C.f.3.3; 29.D.a.1.1; 29.D.a.1.2; 29.D.a.1.3;
29.D.a.2.1; 29.D.a.2.2; 29.D.a.2.3; 29.D.a.3.1; 29.D.a.3.2; 29.D.a.3.3; 29.D.b.1.1;
29.D.b.1.2; 29.D.b.1.3; 29.D.b.2.1; 29.D.b.2.2; 29.D.b.2.3; 29.D.b.3.1; 29.D.b.3.2;
29.D.b.3.3; 29.D.c.1.1; 29.D.c.1.2; 29.D.c.1.3; 29.D.c.2.1; 29.D.c.2.2; 29.D.c.2.3;
29.D.c.3.1; 29.D.c.3.2; 29.D.c.3.3; 29.D.d.1.1; 29.D.d.1.2; 29.D.d.1.3; 29.D.d.2.1;
29.D.d.2.2; 29.D.d.2.3; 29.D.d.3.1; 29.D.d.3.2; 29.D.d.3.3; 29.D.e.1.1; 29.D.e.1.2;
29.D.e.1.3; 29.D.e.2.1; 29.D.e.2.2; 29.D.e.2.3; 29.D.e.3.1; 29.D.e.3.2; 29.D.e.3.3;
29.D.f.1.1; 29.D.f.1.2; 29.D.f.1.3; 29.D.f.2.1; 29.D.f.2.2; 29.D.f.2.3; 29.D.f.3.1;
29.D.f.3.2; 29.D.f.3.3; 30.A.a.1.1; 30.A.a.1.2; 30.A.a.1.3; 30.A.a.2.1; 30.A.a.2.2;
30.A.a.2.3; 30.A.a.3.1; 30.A.a.3.2; 30.A.a.3.3; 30.A.b.1.1; 30.A.b.1.2; 30.A.b.1.3;
30.A.b.2.1; 30.A.b.2.2; 30.A.b.2.3; 30.A.b.3.1; 30.A.b.3.2; 30.A.b.3.3; 30.A.c.1.1;

TABLE 5-continued

Key: Nucleus. Group Z. Group B. Group $R^{1a}$. Group $R^{1b}$.
Saturated Pyrans 30.A.c.1.2; 30.A.c.1.3; 30.A.c.2.1; 30.A.c.2.2; 30.A.c.2.3; 30.A.c.3.1; 30.A.c.3.2;
30.A.c.3.3; 30.A.d.1.1; 30.A.d.1.2; 30.A.d.1.3; 30.A.d.2.1; 30.A.d.2.2; 30.A.d.2.3;
30.A.d.3.1; 30.A.d.3.2; 30.A.d.3.3; 30.A.e.1.1; 30.A.e.1.2; 30.A.e.1.3; 30.A.e.2.1;
30.A.e.2.2; 30.A.e.2.3; 30.A.e.3.1; 30.A.e.3.2; 30.A.e.3.3; 30.A.f.1.1; 30.A.f.1.2;
30.A.f.1.3; 30.A.f.2.1; 30.A.f.2.2; 30.A.f.2.3; 30.A.f.3.1; 30.A.f.3.2; 30.A.f.3.3;
30.B.a.1.1; 30.B.a.1.2; 30.B.a.1.3; 30.B.a.2.1; 30.B.a.2.2; 30.B.a.2.3; 30.B.a.3.1;
30.B.a.3.2; 30.B.a.3.3; 30.B.b.1.1; 30.B.b.1.2; 30.B.b.1.3; 30.B.b.2.1; 30.B.b.2.2;
30.B.b.2.3; 30.B.b.3.1; 30.B.b.3.2; 30.B.b.3.3; 30.B.c.1.1; 30.B.c.1.2; 30.B.c.1.3;
30.B.c.2.1; 30.B.c.2.2; 30.B.c.2.3; 30.B.c.3.1; 30.B.c.3.2; 30.B.c.3.3; 30.B.d.1.1;
30.B.d.1.2; 30.B.d.1.3; 30.B.d.2.1; 30.B.d.2.2; 30.B.d.2.3; 30.B.d.3.1; 30.B.d.3.2;
30.B.d.3.3; 30.B.e.1.1; 30.B.e.1.2; 30.B.e.1.3; 30.B.e.2.1; 30.B.e.2.2; 30.B.e.2.3;
30.B.e.3.1; 30.B.e.3.2; 30.B.e.3.3; 30.B.f.1.1; 30.B.f.1.2; 30.B.f.1.3; 30.B.f.2.1;
30.B.f.2.2; 30.B.f.2.3; 30.B.f.3.1; 30.B.f.3.2; 30.B.f.3.3; 30.C.a.1.1; 30.C.a.1.2;
30.C.a.1.3; 30.C.a.2.1; 30.C.a.2.2; 30.C.a.2.3; 30.C.a.3.1; 30.C.a.3.2; 30.C.a.3.3;
30.C.b.1.1; 30.C.b.1.2; 30.C.b.1.3; 30.C.b.2.1; 30.C.b.2.2; 30.C.b.2.3; 30.C.b.3.1;
30.C.b.3.2; 30.C.b.3.3; 30.C.c.1.1; 30.C.c.1.2; 30.C.c.1.3; 30.C.c.2.1; 30.C.c.2.2;
30.C.c.2.3; 30.C.c.3.1; 30.C.c.3.2; 30.C.c.3.3; 30.C.d.1.1; 30.C.d.1.2; 30.C.d.1.3;
30.C.d.2.1; 30.C.d.2.2; 30.C.d.2.3; 30.C.d.3.1; 30.C.d.3.2; 30.C.d.3.3; 30.C.e.1.1;
30.C.e.1.2; 30.C.e.1.3; 30.C.e.2.1; 30.C.e.2.2; 30.C.e.2.3; 30.C.e.3.1; 30.C.e.3.2;
30.C.e.3.3; 30.C.f.1.1; 30.C.f.1.2; 30.C.f.1.3; 30.C.f.2.1; 30.C.f.2.2; 30.C.f.2.3; 30.C.f.3.1;
30.C.f.3.2; 30.C.f.3.3; 30.D.a.1.1; 30.D.a.1.2; 30.D.a.1.3; 30.D.a.2.1; 30.D.a.2.2;
30.D.a.2.3; 30.D.a.3.1; 30.D.a.3.2; 30.D.a.3.3; 30.D.b.1.1; 30.D.b.1.2; 30.D.b.1.3;
30.D.b.2.1; 30.D.b.2.2; 30.D.b.2.3; 30.D.b.3.1; 30.D.b.3.2; 30.D.b.3.3; 30.D.c.1.1;
30.D.c.1.2; 30.D.c.1.3; 30.D.c.2.1; 30.D.c.2.2; 30.D.c.2.3; 30.D.c.3.1; 30.D.c.3.2;
30.D.c.3.3; 30.D.d.1.1; 30.D.d.1.2; 30.D.d.1.3; 30.D.d.2.1; 30.D.d.2.2; 30.D.d.2.3;
30.D.d.3.1; 30.D.d.3.2; 30.D.d.3.3; 30.D.e.1.1; 30.D.e.1.2; 30.D.e.1.3; 30.D.e.2.1;
30.D.e.2.2; 30.D.e.2.3; 30.D.e.3.1; 30.D.e.3.2; 30.D.e.3.3; 30.D.f.1.1; 30.D.f.1.2.
30.D.f.1.3; 30.D.f.2.1; 30.D.f.2.2; 30.D.f.2.3; 30.D.f.3.1; 30.D.f.3.2; 30.D.f.3.3;
31.A.a.1.1; 31.A.a.1.2; 31.A.a.1.3; 31.A.a.2.1; 31.A.a.2.2; 31.A.a.2.3; 31.A.a.3.1;
31.A.a.3.2; 31.A.a.3.3; 31.A.b.1.1; 31.A.b.1.2; 31.A.b.1.3; 31.A.b.2.1; 31.A.b.2.2;
31.A.b.2.3; 31.A.b.3.1; 31.A.b.3.2; 31.A.b.3.3; 31.A.c.1.1; 31.A.c.1.2; 31.A.c.1.3;
31.A.c.2.1; 31.A.c.2.2; 31.A.c.2.3; 31.A.c.3.1; 31.A.c.3.2; 31.A.c.3.3; 31.A.d.1.1;
31.A.d.1.2; 31.A.d.1.3; 31.A.d.2.1; 31.A.d.2.2; 31.A.d.2.3; 31.A.d.3.1; 31.A.d.3.2;
31.A.d.3.3; 31.A.e.1.1; 31.A.e.1.2; 31.A.e.1.3; 31.A.e.2.1; 31.A.e.2.2; 31.A.e.2.3;
31.A.e.3.1; 31.A.e.3.2; 31.A.e.3.3; 31.A.f.1.1; 31.A.f.1.2; 31.A.f.1.3; 31.A.f.2.1;
31.A.f.2.2; 31.A.f.2.3; 31.A.f.3.1; 31.A.f.3.2; 31.A.f.3.3; 31.B.a.1.1; 31.B.a.1.2;
31.B.a.1.3; 31.B.a.2.1; 31.B.a.2.2; 31.B.a.2.3; 31.B.a.3.1; 31.B.a.3.2; 31.B.a.3.3;
31.B.b.1.1; 31.B.b.1.2; 31.B.b.1.3; 31.B.b.2.1; 31.B.b.2.2; 31.B.b.2.3; 31.B.b.3.1;
31.B.b.3.2; 31.B.b.3.3; 31.B.c.1.1; 31.B.c.1.2; 31.B.c.1.3; 31.B.c.2.1; 31.B.c.2.2;
31.B.c.2.3; 31.B.c.3.1; 31.B.c.3.2; 31.B.c.3.3; 31.B.d.1.1; 31.B.d.1.2; 31.B.d.1.3;
31.B.d.2.1; 31.B.d.2.2; 31.B.d.2.3; 31.B.d.3.1; 31.B.d.3.2; 31.B.d.3.3; 31.B.e.1.1;
31.B.e.1.2; 31.B.e.1.3; 31.B.e.2.1; 31.B.e.2.2; 31.B.e.2.3; 31.B.e.3.1; 31.B.e.3.2;
31.B.e.3.3; 31.B.f.1.1; 31.B.f.1.2; 31.B.f.1.3; 31.B.f.2.1; 31.B.f.2.2; 31.B.f.2.3; 31.B.f.3.1;
31.B.f.3.2; 31.B.f.3.3; 31.C.a.1.1; 31.C.a.1.2; 31.C.a.1.3; 31.C.a.2.1; 31.C.a.2.2;
31.C.a.2.3; 31.C.a.3.1; 31.C.a.3.2; 31.C.a.3.3; 31.C.b.1.1; 31.C.b.1.2; 31.C.b.1.3;
31.C.b.2.1; 31.C.b.2.2; 31.C.b.2.3; 31.C.b.3.1; 31.C.b.3.2; 31.C.b.3.3; 31.C.c.1.1;
31.C.c.1.2; 31.C.c.1.3; 31.C.c.2.1; 31.C.c.2.2; 31.C.c.2.3; 31.C.c.3.1; 31.C.c.3.2;
31.C.c.3.3; 31.C.d.1.1; 31.C.d.1.2; 31.C.d.1.3; 31.C.d.2.1; 31.C.d.2.2; 31.C.d.2.3;
31.C.d.3.1; 31.C.d.3.2; 31.C.d.3.3; 31.C.e.1.1; 31.C.e.1.2; 31.C.e.1.3; 31.C.e.2.1;
31.C.e.2.2; 31.C.e.2.3; 31.C.e.3.1; 31.C.e.3.2; 31.C.e.3.3; 31.C.f.1.1; 31.C.f.1.2;
31.C.f.1.3; 31.C.f.2.1; 31.C.f.2.2; 31.C.f.2.3; 31.C.f.3.1; 31.C.f.3.2; 31.C.f.3.3; 31.D.a.1.1;
31.D.a.1.2; 31.D.a.1.3; 31.D.a.2.1; 31.D.a.2.2; 31.D.a.2.3; 31.D.a.3.1; 31.D.a.3.2;
31.D.a.3.3; 31.D.b.1.1; 31.D.b.1.2; 31.D.b.1.3; 31.D.b.2.1; 31.D.b.2.2; 31.D.b.2.3;
31.D.b.3.1; 31.D.b.3.2; 31.D.b.3.3; 31.D.c.1.1; 31.D.c.1.2; 31.D.c.1.3; 31.D.c.2.1;
31.D.c.2.2; 31.D.c.2.3; 31.D.c.3.1; 31.D.c.3.2; 31.D.c.3.3; 31.D.d.1.1; 31.D.d.1.2;
31.D.d.1.3; 31.D.d.2.1; 31.D.d.2.2; 31.D.d.2.3; 31.D.d.3.1; 31.D.d.3.2; 31.D.d.3.3;
31.D.e.1.1; 31.D.e.1.2; 31.D.e.1.3; 31.D.e.2.1; 31.D.e.2.2; 31.D.e.2.3; 31.D.e.3.1;
31.D.e.3.2; 31.D.e.3.3; 31.D.f.1.1; 31.D.f.1.2; 31.D.f.1.3; 31.D.f.2.1; 31.D.f.2.2;
31.D.f.2.3; 31.D.f.3.1; 31.D.f.3.2; 31.D.f.3.3; 32.A.a.1.1; 32.A.a.1.2; 32.A.a.1.3;
32.A.a.2.1; 32.A.a.2.2; 32.A.a.2.3; 32.A.a.3.1; 32.A.a.3.2; 32.A.a.3.3; 32.A.b.1.1;
32.A.b.1.2; 32.A.b.1.3; 32.A.b.2.1; 32.A.b.2.2; 32.A.b.2.3; 32.A.b.3.1; 32.A.b.3.2;
32.A.b.3.3; 32.A.c.1.1; 32.A.c.1.2; 32.A.c.1.3; 32.A.c.2.1; 32.A.c.2.2; 32.A.c.2.3;
32.A.c.3.1; 32.A.c.3.2; 32.A.c.3.3; 32.A.d.1.1; 32.A.d.1.2; 32.A.d.1.3; 32.A.d.2.1;
32.A.d.2.2; 32.A.d.2.3; 32.A.d.3.1; 32.A.d.3.2; 32.A.d.3.3; 32.A.e.1.1; 32.A.e.1.2;
32.A.e.1.3; 32.A.e.2.1; 32.A.e.2.2; 32.A.e.2.3; 32.A.e.3.1; 32.A.e.3.2; 32.A.e.3.3;
32.A.f.1.1; 32.A.f.1.2; 32.A.f.1.3; 32.A.f.2.1; 32.A.f.2.2; 32.A.f.2.3; 32.A.f.3.1;
32.A.f.3.2; 32.A.f.3.3; 32.B.a.1.1; 32.B.a.1.2; 32.B.a.1.3; 32.B.a.2.1; 32.B.a.2.2;
32.B.a.2.3; 32.B.a.3.1; 32.B.a.3.2; 32.B.a.3.3; 32.B.b.1.1; 32.B.b.1.2; 32.B.b.1.3;
32.B.b.2.1; 32.B.b.2.2; 32.B.b.2.3; 32.B.b.3.1; 32.B.b.3.2; 32.B.b.3.3; 32.B.c.1.1;
32.B.c.1.2; 32.B.c.1.3; 32.B.c.2.1; 32.B.c.2.2; 32.B.c.2.3; 32.B.c.3.1; 32.B.c.3.2;
32.B.c.3.3; 32.B.d.1.1; 32.B.d.1.2; 32.B.d.1.3; 32.B.d.2.1; 32.B.d.2.2; 32.B.d.2.3;
32.B.d.3.1; 32.B.d.3.2; 32.B.d.3.3; 32.B.e.1.1; 32.B.e.1.2; 32.B.e.1.3; 32.B.e.2.1;
32.B.e.2.2; 32.B.e.2.3; 32.B.e.3.1; 32.B.e.3.2; 32.B.e.3.3; 32.B.f.1.1; 32.B.f.1.2;
32.B.f.1.3; 32.B.f.2.1; 32.B.f.2.2; 32.B.f.2.3; 32.B.f.3.1; 32.B.f.3.2; 32.B.f.3.3; 32.C.a.1.1;
32.C.a.1.2; 32.C.a.1.3; 32.C.a.2.1; 32.C.a.2.2; 32.C.a.2.3; 32.C.a.3.1; 32.C.a.3.2;
32.C.a.3.3; 32.C.b.1.1; 32.C.b.1.2; 32.C.b.1.3; 32.C.b.2.1; 32.C.b.2.2; 32.C.b.2.3;

TABLE 5-continued

Key: Nucleus. Group Z. Group B. Group $R^{1a}$. Group $R^{1b}$.
Saturated Pyrans 32.C.b.3.1; 32.C.b.3.2; 32.C.b.3.3; 32.C.c.1.1; 32.C.c.1.2; 32.C.c.1.3; 32.C.c.2.1;
32.C.c.2.2; 32.C.c.2.3; 32.C.c.3.1; 32.C.c.3.2; 32.C.c.3.3; 32.C.d.1.1; 32.C.d.1.2;
32.C.d.1.3; 32.C.d.2.1; 32.C.d.2.2; 32.C.d.2.3; 32.C.d.3.1; 32.C.d.3.2; 32.C.d.3.3;
32.C.e.1.1; 32.C.e.1.2; 32.C.e.1.3; 32.C.e.2.1; 32.C.e.2.2; 32.C.e.2.3; 32.C.e.3.1;
32.C.e.3.2; 32.C.e.3.3; 32.C.f.1.1; 32.C.f.1.2; 32.C.f.1.3; 32.C.f.2.1; 32.C.f.2.2;
32.C.f.2.3; 32.C.f.3.1; 32.C.f.3.2; 32.C.f.3.3; 32.D.a.1.1; 32.D.a.1.2; 32.D.a.1.3;
32.D.a.2.1; 32.D.a.2.2; 32.D.a.2.3; 32.D.a.3.1; 32.D.a.3.2; 32.D.a.3.3; 32.D.b.1.1;
32.D.b.1.2; 32.D.b.1.3; 32.D.b.2.1; 32.D.b.2.2; 32.D.b.2.3; 32.D.b.3.1; 32.D.b.3.2;
32.D.b.3.3; 32.D.c.1.1; 32.D.c.1.2; 32.D.c.1.3; 32.D.c.2.1; 32.D.c.2.2; 32.D.c.2.3;
32.D.c.3.1; 32.D.c.3.2; 32.D.c.3.3; 32.D.d.1.1; 32.D.d.1.2; 32.D.d.1.3; 32.D.d.2.1;
32.D.d.2.2; 32.D.d.2.3; 32.D.d.3.1; 32.D.d.3.2; 32.D.d.3.3; 32.D.e.1.1; 32.D.e.1.2;
32.D.e.1.3; 32.D.e.2.1; 32.D.e.2.2; 32.D.e.2.3; 32.D.e.3.1; 32.D.e.3.2; 32.D.e.3.3;
32.D.f.1.1; 32.D.f.1.2; 32.D.f.1.3; 32.D.f.2.1; 32.D.f.2.2; 32.D.f.2.3; 32.D.f.3.1;
32.D.f.3.2; 32.D.f.3.3; 33.A.a.1.1; 33.A.a.1.2; 33.A.a.1.3; 33.A.a.2.1; 33.A.a.2.2;
33.A.a.2.3; 33.A.a.3.1; 33.A.a.3.2; 33.A.a.3.3; 33.A.b.1.1; 33.A.b.1.2; 33.A.b.1.3;
33.A.b.2.1; 33.A.b.2.2; 33.A.b.2.3; 33.A.b.3.1; 33.A.b.3.2; 33.A.b.3.3; 33.A.c.1.1;
33.A.c.1.2; 33.A.c.1.3; 33.A.c.2.1; 33.A.c.2.2; 33.A.c.2.3; 33.A.c.3.1; 33.A.c.3.2;
33.A.c.3.3; 33.A.d.1.1; 33.A.d.1.2; 33.A.d.1.3; 33.A.d.2.1; 33.A.d.2.2; 33.A.d.2.3;
33.A.d.3.1; 33.A.d.3.2; 33.A.d.3.3; 33.A.e.1.1; 33.A.e.1.2; 33.A.e.1.3; 33.A.e.2.1;
33.A.e.2.2; 33.A.e.2.3; 33.A.e.3.1; 33.A.e.3.2; 33.A.e.3.3; 33.A.f.1.1; 33.A.f.1.2;
33.A.f.1.3; 33.A.f.2.1; 33.A.f.2.2; 33.A.f.2.3; 33.A.f.3.1; 33.A.f.3.2; 33.A.f.3.3; .
33.B.a.1.1; 33.B.a.1.2; 33.B.a.1.3; 33.B.a.2.1; 33.B.a.2.2; 33.B.a.2.3; 33.B.a.3.1;
33.B.a.3.2; 33.B.a.3.3; 33.B.b.1.1; 33.B.b.1.2; 33.B.b.1.3; 33.B.b.2.1; 33.B.b.2.2;
33.B.b.2.3; 33.B.b.3.1; 33.B.b.3.2; 33.B.b.3.3; 33.B.c.1.1; 33.B.c.1.2; 33.B.c.1.3;
33.B.c.2.1; 33.B.c.2.2; 33.B.c.2.3; 33.B.c.3.1; 33.B.c.3.2; 33.B.c.3.3; 33.B.d.1.1;
33.B.d.1.2; 33.B.d.1.3; 33.B.d.2.1; 33.B.d.2.2; 33.B.d.2.3; 33.B.d.3.1; 33.B.d.3.2;
33.B.d.3.3; 33.B.e.1.1; 33.B.e.1.2; 33.B.e.1.3; 33.B.e.2.1; 33.B.e.2.2; 33.B.e.2.3;
33.B.e.3.1; 33.B.e.3.2; 33.B.e.3.3; 33.B.f.1.1; 33.B.f.1.2; 33.B.f.1.3; 33.B.f.2.1;
33.B.f.2.2; 33.B.f.2.3; 33.B.f.3.1; 33.B.f.3.2; 33.B.f.3.3; 33.C.a.1.1; 33.C.a.1.2;
33.C.a.1.3; 33.C.a.2.1; 33.C.a.2.2; 33.C.a.2.3; 33.C.a.3.1; 33.C.a.3.2; 33.C.a.3.3;
33.C.b.1.1; 33.C.b.1.2; 33.C.b.1.3; 33.C.b.2.1; 33.C.b.2.2; 33.C.b.2.3; 33.C.b.3.1;
33.C.b.3.2; 33.C.b.3.3; 33.C.c.1.1; 33.C.c.1.2; 33.C.c.1.3; 33.C.c.2.1; 33.C.c.2.2;
33.C.c.2.3; 33.C.c.3.1; 33.C.c.3.2; 33.C.c.3.3; 33.C.d.1.1; 33.C.d.1.2; 33.C.d.1.3;
33.C.d.2.1; 33.C.d.2.2; 33.C.d.2.3; 33.C.d.3.1; 33.C.d.3.2; 33.C.d.3.3; 33.C.e.1.1;
33.C.e.1.2; 33.C.e.1.3; 33.C.e.2.1; 33.C.e.2.2; 33.C.e.2.3; 33.C.e.3.1; 33.C.e.3.2;
33.C.e.3.3; 33.C.f.1.1; 33.C.f.1.2; 33.C.f.1.3; 33.C.f.2.1; 33.C.f.2.2; 33.C.f.2.3; 33.C.f.3.1;
33.C.f.3.2; 33.C.f.3.3; 33.D.a.1.1; 33.D.a.1.2; 33.D.a.1.3; 33.D.a.2.1; 33.D.a.2.2;
33.D.a.2.3; 33.D.a.3.1; 33.D.a.3.2; 33.D.a.3.3; 33.D.b.1.1; 33.D.b.1.2; 33.D.b.1.3;
33.D.b.2.1; 33.D.b.2.2; 33.D.b.2.3; 33.D.b.3.1; 33.D.b.3.2; 33.D.b.3.3; 33.D.c.1.1;
33.D.c.1.2; 33.D.c.1.3; 33.D.c.2.1; 33.D.c.2.2; 33.D.c.2.3; 33.D.c.3.1; 33.D.c.3.2;
33.D.c.3.3; 33.D.d.1.1; 33.D.d.1.2; 33.D.d.1.3; 33.D.d.2.1; 33.D.d.2.2; 33.D.d.2.3;
33.D.d.3.1; 33.D.d.3.2; 33.D.d.3.3; 33.D.e.1.1; 33.D.e.1.2; 33.D.e.1.3; 33.D.e.2.1;
33.D.e.2.2; 33.D.e.2.3; 33.D.e.3.1; 33.D.e.3.2; 33.D.e.3.3; 33.D.f.1.1; 33.D.f.1.2;
33.D.f.1.3; 33.D.f.2.1; 33.D.f.2.2; 33.D.f.2.3; 33.D.f.3.1; 33.D.f.3.2; 33.D.f.3.3;
34.A.a.1.1; 34.A.a.1.2; 34.A.a.1.3; 34.A.a.2.1; 34.A.a.2.2; 34.A.a.2.3; 34.A.a.3.1;
34.A.a.3.2; 34.A.a.3.3; 34.A.b.1.1; 34.A.b.1.2; 34.A.b.1.3; 34.A.b.2.1; 34.A.b.2.2;
34.A.b.2.3; 34.A.b.3.1; 34.A.b.3.2; 34.A.b.3.3; 34.A.c.1.1; 34.A.c.1.2; 34.A.c.1.3;
34.A.c.2.1; 34.A.c.2.2; 34.A.c.2.3; 34.A.c.3.1; 34.A.c.3.2; 34.A.c.3.3; 34.A.d.1.1;
34.A.d.1.2; 34.A.d.1.3; 34.A.d.2.1; 34.A.d.2.2; 34.A.d.2.3; 34.A.d.3.1; 34.A.d.3.2;
34.A.d.3.3; 34.A.e.1.1; 34.A.e.1.2; 34.A.e.1.3; 34.A.e.2.1; 34.A.e.2.2; 34.A.e.2.3;
34.A.e.3.1; 34.A.e.3.2; 34.A.e.3.3; 34.A.f.1.1; 34.A.f.1.2; 34.A.f.1.3; 34.A.f.2.1;
34.A.f.2.2; 34.A.f.2.3; 34.A.f.3.1; 34.A.f.3.2; 34.A.f.3.3; 34.B.a.1.1; 34.B.a.1.2;
34.B.a.1.3; 34.B.a.2.1; 34.B.a.2.2; 34.B.a.2.3; 34.B.a.3.1; 34.B.a.3.2; 34.B.a.3.3;
34.B.b.1.1; 34.B.b.1.2; 34.B.b.1.3; 34.B.b.2.1; 34.B.b.2.2; 34.B.b.2.3; 34.B.b.3.1;
34.B.b.3.2; 34.B.b.3.3; 34.B.c.1.1; 34.B.c.1.2; 34.B.c.1.3; 34.B.c.2.1; 34.B.c.2.2;
34.B.c.2.3; 34.B.c.3.1; 34.B.c.3.2; 34.B.c.3.3; 34.B.d.1.1; 34.B.d.1.2; 34.B.d.1.3;
34.B.d.2.1; 34.B.d.2.2; 34.B.d.2.3; 34.B.d.3.1; 34.B.d.3.2; 34.B.d.3.3; 34.B.e.1.1;
34.B.e.1.2; 34.B.e.1.3; 34.B.e.2.1; 34.B.e.2.2; 34.B.e.2.3; 34.B.e.3.1; 34.B.e.3.2;
34.B.e.3.3; 34.B.f.1.1; 34.B.f.1.2; 34.B.f.1.3; 34.B.f.2.1; 34.B.f.2.2; 34.B.f.2.3; 34.B.f.3.1;
34.B.f.3.2; 34.B.f.3.3; 34.C.a.1.1; 34.C.a.1.2; 34.C.a.1.3; 34.C.a.2.1; 34.C.a.2.2;
34.C.a.2.3; 34.C.a.3.1; 34.C.a.3.2; 34.C.a.3.3; 34.C.b.1.1; 34.C.b.1.2; 34.C.b.1.3;
34.C.b.2.1; 34.C.b.2.2; 34.C.b.2.3; 34.C.b.3.1; 34.C.b.3.2; 34.C.b.3.3; 34.C.c.1.1;
34.C.c.1.2; 34.C.c.1.3; 34.C.c.2.1; 34.C.c.2.2; 34.C.c.2.3; 34.C.c.3.1; 34.C.c.3.2;
34.C.c.3.3; 34.C.d.1.1; 34.C.d.1.2; 34.C.d.1.3; 34.C.d.2.1; 34.C.d.2.2; 34.C.d.2.3;
34.C.d.3.1; 34.C.d.3.2; 34.C.d.3.3; 34.C.e.1.1; 34.C.e.1.2; 34.C.e.1.3; 34.C.e.2.1;
34.C.e.2.2; 34.C.e.2.3; 34.C.e.3.1; 34.C.e.3.2; 34.C.e.3.3; 34.C.f.1.1; 34.C.f.1.2;
34.C.f.1.3; 34.C.f.2.1; 34.C.f.2.2; 34.C.f.2.3; 34.C.f.3.1; 34.C.f.3.2; 34.C.f.3.3; 34.D.a.1.1;
34.D.a.1.2; 34.D.a.1.3; 34.D.a.2.1; 34.D.a.2.2; 34.D.a.2.3; 34.D.a.3.1; 34.D.a.3.2;
34.D.a.3.3; 34.D.b.1.1; 34.D.b.1.2; 34.D.b.1.3; 34.D.b.2.1; 34.D.b.2.2; 34.D.b.2.3;
34.D.b.3.1; 34.D.b.3.2; 34.D.b.3.3; 34.D.c.1.1; 34.D.c.1.2; 34.D.c.1.3; 34.D.c.2.1;
34.D.c.2.2; 34.D.c.2.3; 34.D.c.3.1; 34.D.c.3.2; 34.D.c.3.3; 34.D.d.1.1; 34.D.d.1.2;
34.D.d.1.3; 34.D.d.2.1; 34.D.d.2.2; 34.D.d.2.3; 34.D.d.3.1; 34.D.d.3.2; 34.D.d.3.3;
34.D.e.1.1; 34.D.e.1.2; 34.D.e.1.3; 34.D.e.2.1; 34.D.e.2.2; 34.D.e.2.3; 34.D.e.3.1;
34.D.e.3.2; 34.D.e.3.3; 34.D.f.1.1; 34.D.f.1.2; 34.D.f.1.3; 34.D.f.2.1; 34.D.f.2.2;
34 D.f.2.3; 34.D.f.3.1; 34.D.f.3.2; 34.D.f.3.3.

TABLE 5

Key: Nucleus. Group Z. Group B. Group $R^{1a}$.
Furans

35.A.a.1; 35.A.a.2; 35.A.a.3; 35.A.b.1; 35.A.b.2; 35.A.b.3; 35.A.c.1; 35.A.c.2;
35.A.c.3; 35.A.d.1; 35.A.d.2; 35.A.d.3; 35.A.e.1; 35.A.e.2; 35.A.e.3; 35.A.f.1;
35.A.f.2; 35.A.f.3; 35.B.a.1; 35.B.a.2; 35.B.a.3; 35.B.b.1; 35.B.b.2; 35.B.b.3; 35.B.c.1;
35.B.c.2; 35.B.c.3; 35.B.d.1; 35.B.d.2; 35.B.d.3; 35.B.e.1; 35.B.e.2; 35.B.e.3; 35.B.f.1;
35.B.f.2; 35.B.f.3; 35.C.a.1; 35.C.a.2; 35.C.a.3; 35.C.b.1; 35.C.b.2; 35.C.b.3; 35.C.c.1;
35.C.c.2; 35.C.c.3; 35.C.d.1; 35.C.d.2; 35.C.d.3; 35.C.e.1; 35.C.e.2; 35.C.e.3; 35.C.f.1;
35.C.f.2; 35.C.f.3; 35.D.a.1; 35.D.a.2; 35.D.a.3; 35.D.b.1; 35.D.b.2; 35.D.b.3; 35.D.c.1;
35.D.c.2; 35.D.c.3; 35.D.d.1; 35.D.d.2; 35.D.d.3; 35.D.e.1; 35.D.e.2; 35.D.e.3; 35.D.f.1;
35.D.f.2; 35.D.f.3; 36.A.a.1; 36.A.a.2; 36.A.a.3; 36.A.b.1; 36.A.b.2; 36.A.b.3; 36.A.c.1;
36.A.c.2; 36.A.c.3; 36.A.d.1; 36.A.d.2; 36.A.d.3; 36.A.e.1; 36.A.e.2; 36.A.e.3;
36.A.f.1; 36.A.f.2; 36.A.f.3; 36.B.a.1; 36.B.a.2; 36.B.a.3; 36.B.b.1; 36.B.b.2; 36.B.b.3;
36.B.c.1; 36.B.c.2; 36.B.c.3; 36.B.d.1; 36.B.d.2; 36.B.d.3; 36.B.e.1; 36.B.e.2; 36.B.e.3;
36.B.f.1; 36.B.f.2; 36.B.f.3; 36.C.a.1; 36.C.a.2; 36.C.a.3; 36.C.b.1; 36.C.b.2; 36.C.b.3;
36.C.c.1; 36.C.c.2; 36.C.c.3; 36.C.d.1; 36.C.d.2; 36.C.d.3; 36.C.e.1; 36.C.e.2; 36.C.e.3;
36.C.f.1; 36.C.f.2; 36.C.f.3; 36.D.a.1; 36.D.a.2; 36.D.a.3; 36.D.b.1; 36.D.b.2; 36.D.b.3;
36.D.c.1; 36.D.c.2; 36.D.c.3; 36.D.d.1; 36.D.d.2; 36.D.d.3; 36.D.e.1; 36.D.e.2; 36.D.e.3;
36.D.f.1; 36.D.f.2; 36.D.f.3; 37.A.a.1; 37.A.a.2; 37.A.a.3; 37.A.b.1; 37.A.b.2; 37.A.b.3;
37.A.c.1; 37.A.c.2; 37.A.c.3; 37.A.d.1; 37.A.d.2; 37.A.d.3; 37.A.e.1; 37.A.e.2;
37.A.e.3; 37.A.f.1; 37.A.f.2; 37.A.f.3; 37.B.a.1; 37.B.a.2; 37.B.a.3; 37.B.b.1; 37.B.b.2;
37.B.b.3; 37.B.c.1; 37.B.c.2; 37.B.c.3; 37.B.d.1; 37.B.d.2; 37.B.d.3; 37.B.e.1; 37.B.e.2;
37.B.e.3; 37.B.f.1; 37.B.f.2; 37.B.f.3; 37.C.a.1; 37.C.a.2; 37.C.a.3; 37.C.b.1; 37.C.b.2;
37.C.b.3; 37.C.c.1; 37.C.c.2; 37.C.c.3; 37.C.d.1; 37.C.d.2; 37.C.d.3; 37.C.e.1; 37.C.e.2;
37.C.e.3; 37.C.f.1; 37.C.f.2; 37.C.f.3; 37.D.a.1; 37.D.a.2; 37.D.a.3; 37.D.b.1; 37.D.b.2;
37.D.b.3; 37.D.c.1; 37.D.c.2; 37.D.c.3; 37.D.d.1; 37.D.d.2; 37.D.d.3; 37.D.e.1; 37.D.e.2;
37.D.e.3; 37.D.f.1; 37.D.f.2; 37.D.f.3; 38.A.a.1; 38.A.a.2; 38.A.a.3; 38.A.b.1; 38.A.b.2;
38.A.b.3; 38.A.c.1; 38.A.c.2; 38.A.c.3; 38.A.d.1; 38.A.d.2; 38.A.d.3; 38.A.e.1;
38.A.e.2; 38.A.e.3; 38.A.f.1; 38.A.f.2; 38.A.f.3; 38.B.a.1; 38.B.a.2; 38.B.a.3; 38.B.b.1;
38.B.b.2; 38.B.b.3; 38.B.c.1; 38.B.c.2; 38.B.c.3; 38.B.d.1; 38.B.d.2; 38.B.d.3; 38.B.e.1;
38.B.e.2; 38.B.e.3; 38.B.f.1; 38.B.f.2; 38.B.f.3; 38.C.a.1; 38.C.a.2; 38.C.a.3; 38.C.b.1;
38.C.b.2; 38.C.b.3; 38.C.c.1; 38.C.c.2; 38.C.c.3; 38.C.d.1; 38.C.d.2; 38.C.d.3; 38.C.e.1;
38.C.e.2; 38.C.e.3; 38.C.f.1; 38.C.f.2; 38.C.f.3; 38.D.a.1; 38.D.a.2; 38.D.a.3; 38.D.b.1;
38.D.b.2; 38.D.b.3; 38.D.c.1; 38.D.c.2; 38.D.c.3; 38.D.d.1; 38.D.d.2; 38.D.d.3; 38.D.e.1;
38.D.e.2; 38.D.e.3; 38.D.f.1; 38.D.f.2; 38.D.f.3; 39.A.a.1; 39.A.a.2; 39.A.a.3; 39.A.b.1;
39.A.b.2; 39.A.b.3; 39.A.c.1; 39.A.c.2; 39.A.c.3; 39.A.d.1; 39.A.d.2; 39.A.d.3;
39.A.e.1; 39.A.e.2; 39.A.e.3; 39.A.f.1; 39.A.f.2; 39.A.f.3; 39.B.a.1; 39.B.a.2; 39.B.a.3;
39.B.b.1; 39.B.b.2; 39.B.b.3; 39.B.c.1; 39.B.c.2; 39.B.c.3; 39.B.d.1; 39.B.d.2; 39.B.d.3;
39.B.e.1; 39.B.e.2; 39.B.e.3; 39.B.f.1; 39.B.f.2; 39.B.f.3; 39.C.a.1; 39.C.a.2; 39.C.a.3;
39.C.b.1; 39.C.b.2; 39.C.b.3; 39.C.c.1; 39.C.c.2; 39.C.c.3; 39.C.d.1; 39.C.d.2; 39.C.d.3;
39.C.e.1; 39.C.e.2; 39.C.e.3; 39.C.f.1; 39.C.f.2; 39.C.f.3; 39.D.a.1; 39.D.a.2; 39.D.a.3;
39.D.b.1; 39.D.b.2; 39.D.b.3; 39.D.c.1; 39.D.c.2; 39.D.c.3; 39.D.d.1; 39.D.d.2; 39.D.d.3;
39.D.e.1; 39.D.e.2; 39.D.e.3; 39.D.f.1; 39.D.f.2; 39.D.f.3; 40.A.a.1; 40.A.a.2; 40.A.a.3;
40.A.b.1; 40.A.b.2; 40.A.b.3; 40.A.c.1; 40.A.c.2; 40.A.c.3; 40.A.d.1; 40.A.d.2;
40.A.d.3; 40.A.e.1; 40.A.e.2; 40.A.e.3; 40.A.f.1; 40.A.f.2; 40.A.f.3; 40.B.a.1; 40.B.a.2;
40.B.a.3; 40.B.b.1; 40.B.b.2; 40.B.b.3; 40.B.c.1; 40.B.c.2; 40.B.c.3; 40.B.d.1; 40.B.d.2;
40.B.d.3; 40.B.e.1; 40.B.e.2; 40.B.e.3; 40.B.f.1; 40.B.f.2; 40.B.f.3; 40.C.a.1; 40.C.a.2;
40.C.a.3; 40.C.b.1; 40.C.b.2; 40.C.b.3; 40.C.c.1; 40.C.c.2; 40.C.c.3; 40.C.d.1; 40.C.d.2;
40.C.d.3; 40.C.e.1; 40.C.e.2; 40.C.e.3; 40.C.f.1; 40.C.f.2; 40.C.f.3; 40.D.a.1; 40.D.a.2;
40.D.a.3; 40.D.b.1; 40.D.b.2; 40.D.b.3; 40.D.c.1; 40.D.c.2; 40.D.c.3; 40.D.d.1; 40.D.d.2;
40.D.d.3; 40.D.e.1; 40.D.e.2; 40.D.e.3; 40.D.f.1; 40.D.f.2; 40.D.f.3; 41.A.a.1; 41.A.a.2;
41.A.a.3; 41.A.b.1; 41.A.b.2; 41.A.b.3; 41.A.c.1; 41.A.c.2; 41.A.c.3; 41.A.d.1;
41.A.d.2; 41.A.d.3; 41.A.e.1; 41.A.e.2; 41.A.e.3; 41.A.f.1; 41.A.f.2; 41.A.f.3; 41.B.a.1;
41.B.a.2; 41.B.a.3; 41.B.b.1; 41.B.b.2; 41.B.b.3; 41.B.c.1; 41.B.c.2; 41.B.c.3; 41.B.d.1;
41.B.d.2; 41.B.d.3; 41.B.e.1; 41.B.e.2; 41.B.e.3; 41.B.f.1; 41.B.f.2; 41.B.f.3; 41.C.a.1;
41.C.a.2; 41.C.a.3; 41.C.b.1; 41.C.b.2; 41.C.b.3; 41.C.c.1; 41.C.c.2; 41.C.c.3; 41.C.d.1;
41.C.d.2; 41.C.d.3; 41.C.e.1; 41.C.e.2; 41.C.e.3; 41.C.f.1; 41.C.f.2; 41.C.f.3; 41.D.a.1;
41.D.a.2; 41.D.a.3; 41.D.b.1; 41.D.b.2; 41.D.b.3; 41.D.c.1; 41.D.c.2; 41.D.c.3; 41.D.d.1;
41.D.d.2; 41.D.d.3; 41.D.e.1; 41.D.e.2; 41.D.e.3; 41.D.f.1; 41.D.f.2; 41.D.f.3; 42.A.a.1;
42.A.a.2; 42.A.a.3; 42.A.b.1; 42.A.b.2; 42.A.b.3; 42.A.c.1; 42.A.c.2; 42.A.c.3;
42.A.d.1; 42.A.d.2; 42.A.d.3; 42.A.e.1; 42.A.e.2; 42.A.e.3; 42.A.f.1; 42.A.f.2;
42.A.f.3; 42.B.a.1; 42.B.a.2; 42.B.a.3; 42.B.b.1; 42.B.b.2; 42.B.b.3; 42.B.c.1; 42.B.c.2;
42.B.c.3; 42.B.d.1; 42.B.d.2; 42.B.d.3; 42.B.e.1; 42.B.e.2; 42.B.e.3; 42.B.f.1; 42.B.f.2;
42.B.f.3; 42.C.a.1; 42.C.a.2; 42.C.a.3; 42.C.b.1; 42.C.b.2; 42.C.b.3; 42.C.c.1; 42.C.c.2;
42.C.c.3; 42.C.d.1; 42.C.d.2; 42.C.d.3; 42.C.e.1; 42.C.e.2; 42.C.e.3; 42.C.f.1; 42.C.f.2;
42.C.f.3; 42.D.a.1; 42.D.a.2; 42.D.a.3; 42.D.b.1; 42.D.b.2; 42.D.b.3; 42.D.c.1; 42.D.c.2;
42.D.c.3; 42.D.d.1; 42.D.d.2; 42.D.d.3; 42.D.e.1; 42.D.e.2; 42.D.e.3; 42.D.f.1; 42.D.f.2;
42.D.f.3; 43.A.a.1; 43.A.a.2; 43.A.a.3; 43.A.b.1; 43.A.b.2; 43.A.b.3; 43.A.c.1;
43.A.c.2; 43.A.c.3; 43.A.d.1; 43.A.d.2; 43.A.d.3; 43.A.e.1; 43.A.e.2; 43.A.e.3;
43.A.f.1; 43.A.f.2; 43.A.f.3; 43.B.a.1; 43.B.a.2; 43.B.a.3; 43.B.b.1; 43.B.b.2; 43.B.b.3;
43.B.c.1; 43.B.c.2; 43.B.c.3; 43.B.d.1; 43.B.d.2; 43.B.d.3; 43.B.e.1; 43.B.e.2; 43.B.e.3;
43.B.f.1; 43.B.f.2; 43.B.f.3; 43.C.a.1; 43.C.a.2; 43.C.a.3; 43.C.b.1; 43.C.b.2; 43.C.b.3;
43.C.c.1; 43.C.c.2; 43.C.c.3; 43.C.d.1; 43.C.d.2; 43.C.d.3; 43.C.e.1; 43.C.e.2; 43.C.e.3;
43.C.f.1; 43.C.f.2; 43.C.f.3; 43.D.a.1; 43.D.a.2; 43.D.a.3; 43.D.b.1; 43.D.b.2; 43.D.b.3;
43.D.c.1; 43.D.c.2; 43.D.c.3; 43.D.d.1; 43.D.d.2; 43.D.d.3; 43.D.e.1; 43.D.e.2; 43.D.e.3;
43.D.f.1; 43.D.f.2; 43.D.f.3;

TABLE 5

Key: Nucleus. Group Z. Group B. Group $R^{1b.}$
1–2 Unsaturated Pyrans

19.A.a.1; 19.A.a.2; 19.A.a.3; 19.A.b.1; 19.A.b.2; 19.A.b.3; 19.A.c.1; 19.A.c.2;
19.A.c.3; 19.A.d.1; 19.A.d.2; 19.A.d.3; 19.A.e.1; 19.A.e.2; 19.A.e.3; 19.A.f.1;
19.A.f.2; 19.A.f.3; 19.B.a.1; 19.B.a.2; 19.B.a.3; 19.B.b.1; 19.B.b.2; 19.B.b.3; 19.B.c.1;
19.B.c.2; 19.B.c.3; 19.B.d.1; 19.B.d.2; 19.B.d.3; 19.B.e.1; 19.B.e.2; 19.B.e.3; 19.B.f.1;
19.B.f.2; 19.B.f.3; 19.C.a.1; 19.C.a.2; 19.C.a.3; 19.C.b.1; 19.C.b.2; 19.C.b.3; 19.C.c.1;
19.C.c.2; 19.C.c.3; 19.C.d.1; 19.C.d.2; 19.C.d.3; 19.C.e.1; 19.C.e.2; 19.C.e.3; 19.C.f.1;
19.C.f.2; 19.C.f.3; 19.D.a.1; 19.D.a.2; 19.D.a.3; 19.D.b.1; 19.D.b.2; 19.D.b.3; 19.D.c.1;
19.D.c.2; 19.D.c.3; 19.D.d.1; 19.D.d.2; 19.D.d.3; 19.D.e.1; 19.D.e.2; 19.D.e.3; 19.D.f.1;
19.D.f.2; 19.D.f.3; 20.A.a.1; 20.A.a.2; 20.A.a.3; 20.A.b.1; 20.A.b.2; 20.A.b.3; 20.A.c.1;
20.A.c.2; 20.A.c.3; 20.A.d.1; 20.A.d.2; 20.A.d.3; 20.A.e.1; 20.A.e.2; 20.A.e.3;
20.A.f.1; 20.A.f.2; 20.A.f.3; 20.B.a.1; 20.B.a.2; 20.B.a.3; 20.B.b.1; 20.B.b.2; 20.B.b.3;
20.B.c.1; 20.B.c.2; 20.B.c.3; 20.B.d.1; 20.B.d.2; 20.B.d.3; 20.B.e.1; 20.B.e.2; 20.B.e.3;
20.B.f.1; 20.B.f.2; 20.B.f.3; 20.C.a.1; 20.C.a.2; 20.C.a.3; 20.C.b.1; 20.C.b.2; 20.C.b.3;
20.C.c.1; 20.C.c.2; 20.C.c.3; 20.C.d.1; 20.C.d.2; 20.C.d.3; 20.C.e.1; 20.C.e.2; 20.C.e.3;
20.C.f.1; 20.C.f.2; 20.C.f.3; 20.D.a.1; 20.D.a.2; 20.D.a.3; 20.D.b.1; 20.D.b.2; 20.D.b.3;
20.D.c.1; 20.D.c.2; 20.D.c.3; 20.D.d.1; 20.D.d.2; 20.D.d.3; 20.D.e.1; 20.D.e.2; 20.D.e.3;
20.D.f.1; 20.D.f.2; 20.D.f.3; 21.A.a.1; 21.A.a.2; 21.A.a.3; 21.A.b.1; 21.A.b.2; 21.A.b.3;
21.A.c.1; 21.A.c.2; 21.A.c.3; 21.A.d.1; 21.A.d.2; 21.A.d.3; 21.A.e.1; 21.A.e.2;
21.A.e.3; 21.A.f.1; 21.A.f.2; 21.A.f.3; 21.B.a.1; 21.B.a.2; 21.B.a.3; 21.B.b.1; 21.B.b.2;
21.B.b.3; 21.B.c.1; 21.B.c.2; 21.B.c.3; 21.B.d.1; 21.B.d.2; 21.B.d.3; 21.B.e.1; 21.B.e.2;
21.B.e.3; 21.B.f.1; 21.B.f.2; 21.B.f.3; 21.C.a.1; 21.C.a.2; 21.C.a.3; 21.C.b.1; 21.C.b.2;
21.C.b.3; 21.C.c.1; 21.C.c.2; 21.C.c.3; 21.C.d.1; 21.C.d.2; 21.C.d.3; 21.C.e.1; 21.C.e.2;
21.C.e.3; 21.C.f.1; 21.C.f.2; 21.C.f.3; 21.D.a.1; 21.D.a.2; 21.D.a.3; 21.D.b.1; 21.D.b.2;
21.D.b.3; 21.D.c.1; 21.D.c.2; 21.D.c.3; 21.D.d.1; 21.D.d.2; 21.D.d.3; 21.D.e.1; 21.D.e.2;
21.D.e.3; 21.D.f.1; 21.D.f.2; 21.D.f.3; 22.A.a.1; 22.A.a.2; 22.A.a.3; 22.A.b.1; 22.A.b.2;
22.A.b.3; 22.A.c.1; 22.A.c.2; 22.A.c.3; 22.A.d.1; 22.A.d.2; 22.A.d.3; 22.A.e.1;
22.A.e.2; 22.A.e.3; 22.A.f.1; 22.A.f.2; 22.A.f.3; 22.B.a.1; 22.B.a.2; 22.B.a.3; 22.B.b.1;
22.B.b.2; 22.B.b.3; 22.B.c.1; 22.B.c.2; 22.B.c.3; 22.B.d.1; 22.B.d.2; 22.B.d.3; 22.B.e.1;
22.B.e.2; 22.B.e.3; 22.B.f.1; 22.B.f.2; 22.B.f.3; 22.C.a.1; 22.C.a.2; 22.C.a.3; 22.C.b.1;
22.C.b.2; 22.C.b.3; 22.C.c.1; 22.C.c.2; 22.C.c.3; 22.C.d.1; 22.C.d.2; 22.C.d.3; 22.C.e.1;
22.C.e.2; 22.C.e.3; 22.C.f.1; 22.C.f.2; 22.C.f.3; 22.D.a.1; 22.D.a.2; 22.D.a.3; 22.D.b.1;
22.D.b.2; 22.D.b.3; 22.D.c.1; 22.D.c.2; 22.D.c.3; 22.D.d.1; 22.D.d.2; 22.D.d.3; 22.D.e.1;
22.D.e.2; 22.D.e.3; 22.D.f.1; 22.D.f.2; 22.D.f.3; 23.A.a.1; 23.A.a.2; 23.A.a.3; 23.A.b.1;
23.A.b.2; 23.A.b.3; 23.A.c.1; 23.A.c.2; 23.A.c.3; 23.A.d.1; 23.A.d.2; 23.A.d.3;
23.A.e.1; 23.A.e.2; 23.A.e.3; 23.A.f.1; 23.A.f.2; 23.A.f.3; 23.B.a.1; 23.B.a.2; 23.B.a.3;
23.B.b.1; 23.B.b.2; 23.B.b.3; 23.B.c.1; 23.B.c.2; 23.B.c.3; 23.B.d.1; 23.B.d.2; 23.B.d.3;
23.B.e.1; 23.B.e.2; 23.B.e.3; 23.B.f.1; 23.B.f.2; 23.B.f.3; 23.C.a.1; 23.C.a.2; 23.C.a.3;
23.C.b.1; 23.C.b.2; 23.C.b.3; 23.C.c.1; 23.C.c.2; 23.C.c.3; 23.C.d.1; 23.C.d.2; 23.C.d.3;
23.C.e.1; 23.C.e.2; 23.C.e.3; 23.C.f.1; 23.C.f.2; 23.C.f.3; 23.D.a.1; 23.D.a.2; 23.D.a.3;
23.D.b.1; 23.D.b.2; 23.D.b.3; 23.D.c.1; 23.D.c.2; 23.D.c.3; 23.D.d.1; 23.D.d.2; 23.D.d.3;
23.D.e.1; 23.D.e.2; 23.D.e.3; 23.D.f.1; 23.D.f.2; 23.D.f.3; 24.A.a.1; 24.A.a.2; 24.A.a.3;
24.A.b.1; 24.A.b.2; 24.A.b.3; 24.A.c.1; 24.A.c.2; 24.A.c.3; 24.A.d.1; 24.A.d.2;
24.A.d.3; 24.A.e.1; 24.A.e.2; 24.A.e.3; 24.A.f.1; 24.A.f.2; 24.A.f.3; 24.B.a.1; 24.B.a.2;
24.B.a.3; 24.B.b.1; 24.B.b.2; 24.B.b.3; 24.B.c.1; 24.B.c.2; 24.B.c.3; 24.B.d.1; 24.B.d.2;
24.B.d.3; 24.B.e.1; 24.B.e.2; 24.B.e.3; 24.B.f.1; 24.B.f.2; 24.B.f.3; 24.C.a.1; 24.C.a.2;
24.C.a.3; 24.C.b.1; 24.C.b.2; 24.C.b.3; 24.C.c.1; 24.C.c.2; 24.C.c.3; 24.C.d.1; 24.C.d.2;
24.C.d.3; 24.C.e.1; 24.C.e.2; 24.C.e.3; 24.C.f.1; 24.C.f.2; 24.C.f.3; 24.D.a.1; 24.D.a.2;
24.D.a.3; 24.D.b.1; 24.D.b.2; 24.D.b.3; 24.D.c.1; 24.D.c.2; 24.D.c.3; 24.D.d.1; 24.D.d.2;
24.D.d.3; 24.D.e.1; 24.D.e.2; 24.D.e.3; 24.D.f.1; 24.D.f.2; 24.D.f.3; 25.A.a.1; 25.A.a.2;
25.A.a.3; 25.A.b.1; 25.A.b.2; 25.A.b.3; 25.A.c.1; 25.A.c.2; 25.A.c.3; 25.A.d.1;
25.A.d.2; 25.A.d.3; 25.A.e.1; 25.A.e.2; 25.A.e.3; 25.A.f.1; 25.A.f.2; 25.A.f.3; 25.B.a.1;
25.B.a.2; 25.B.a.3; 25.B.b.1; 25.B.b.2; 25.B.b.3; 25.B.c.1; 25.B.c.2; 25.B.c.3; 25.B.d.1;
25.B.d.2; 25.B.d.3; 25.B.e.1; 25.B.e.2; 25.B.e.3; 25.B.f.1; 25.B.f.2; 25.B.f.3; 25.C.a.1;
25.C.a.2; 25.C.a.3; 25.C.b.1; 25.C.b.2; 25.C.b.3; 25.C.c.1; 25.C.c.2; 25.C.c.3; 25.C.d.1;
25.C.d.2; 25.C.d.3; 25.C.e.1; 25.C.e.2; 25.C.e.3; 25.C.f.1; 25.C.f.2; 25.C.f.3; 25.D.a.1;
25.D.a.2; 25.D.a.3; 25.D.b.1; 25.D.b.2; 25.D.b.3; 25.D.c.1; 25.D.c.2; 25.D.c.3; 25.D.d.1;
25.D.d.2; 25.D.d.3; 25.D.e.1; 25.D.e.2; 25.D.e.3; 25.D.f.1; 25.D.f.2; 25.D.f.3; 26.A.a.1;
26.A.a.2; 26.A.a.3; 26.A.b.1; 26.A.b.2; 26.A.b.3; 26.A.c.1; 26.A.c.2; 26.A.c.3;
26.A.d.1; 26.A.d.2; 26.A.d.3; 26.A.e.1; 26.A.e.2; 26.A.e.3; 26.A.f.1; 26.A.f.2;
26.A.f.3; 26.B.a.1; 26.B.a.2; 26.B.a.3; 26.B.b.1; 26.B.b.2; 26.B.b.3; 26.B.c.1; 26.B.c.2;
26.B.c.3; 26.B.d.1; 26.B.d.2; 26.B.d.3; 26.B.e.1; 26.B.e.2; 26.B.e.3; 26.B.f.1; 26.B.f.2;
26.B.f.3; 26.C.a.1; 26.C.a.2; 26.C.a.3; 26.C.b.1; 26.C.b.2; 26.C.b.3; 26.C.c.1; 26.C.c.2;
26.C.c.3; 26.C.d.1; 26.C.d.2; 26.C.d.3; 26.C.e.1; 26.C.e.2; 26.C.e.3; 26.C.f.1; 26.C.f.2;
26.C.f.3; 26.D.a.1; 26.D.a.2; 26.D.a.3; 26.D.b.1; 26.D.b.2; 26.D.b.3; 26.D.c.1; 26.D.c.2;
26.D.c.3; 26.D.d.1; 26.D.d.2; 26.D.d.3; 26.D.e.1; 26.D.e.2; 26.D.e.3; 26.D.f.1; 26.D.f.2;
26.D.f.3;

TABLE 5

Key: Nucleus. Group Z. Group B.
Fused Cyclopropyl and 2-3 Unsaturated Pyrans

05.A.a; 05.A.b; 05.A.c; 05.A.d; 05.A.e; 05.A.f; 05.B.a; 05.B.b; 05.B.c; 05.B.d; 05.B.e; 05.B.f; 05.C.a; 05.C.b; 05.C.c; 05.C.d; 05.C.e; 05.C.f; 05.D.a; 05;D.b; 05.D.c; 05.D.d; 05.D.e; 05.D.f; 06.A.a; 06.A.b; 06.A.c; 06.A.d; 06.A.e; 06.A.f; 06.B.a; 06.B.b; 06.B.c; 06.B.d; 06.B.e; 06.B.f; 06.C.a; 06.C.b; 06.C.c; 06.C.d; 06.C.e; 06.C.f; 06.D.a; 06.D.b; 06.D.c; 06.D.d; 06.D.e; 06.D.f; 07.A.a; 07.A.b; 07.A.c; 07.A.d; 07.A.e; 07.A.f; 07.B.a; 07.B.b; 07.B.c; 07.B.d; 07.B.e; 07.B.f; 07.C.a; 07.C.b; 07.C.c; 07.C.d; 07.C.e; 07.C.f; 07.D.a; 07.D.b; 07.D.c; 07.D.d; 07.D.e; 07.D.f; 08.A.a; 08.A.b; 08.A.c; 08.A.d; 08.A.e; 08.A.f; 08.B.a; 08.B.b; 08.B.c; 08.B.d; 08.B.e; 08.B.f; 08.C.a; 08.C.b; 08.C.c; 08.C.d; 08.C.e; 08.C.f; 08.D.a; 08.D.b; 08.D.c; 08.D.d; 08.D.e; 08.D.f; 09.A.a; 09.A.b; 09.A.c; 09.A.d; 09.A.e; 09.A.f; 09.A.g; 09.A.h; 09.A.i; 09.A.j; 09.A.k; 09.A.l; 09.B.a; 09.B.b; 09.B.c; 09.B.d; 09.B.e; 09.B.f; 09.B.g; 09.B.h; 09.B.i; 09.B.j; 09.B.k; 09.B.l; 09.C.a; 09.C.b; 09.C.c; 09.C.d; 09.C.e; 09.C.f; 09.C.g; 09.C.h; 09.C.i; 09.C.j; 09.C.k; 09.C.l; 09.D.a; 09.D.b; 09.D.c; 09.D.d; 09.D.e; 09.D.f; 09.D.g; 09.D.h; 09.D.i; 09.D.j; 09.D.k; 09.D.l; 09.E.a; 09.E.b; 09.E.c; 09.E.d; 09.E.e; 09.E.f; 09.E.g; 09.E.h; 09.E.i; 09.E.j; 09.E.k; 09.E.l; 09.F.a; 09.F.b; 09.F.c; 09.F.d; 09.F.e; 09.F.f; 09.F.g; 09.F.h; 09.F.i; 09.F.j; 09.F.k; 09.F.l; 09.G.a; 09.G.b; 09.G.c; 09.G.d; 09.G.e; 09.G.f; 09.G.g; 09.G.h; 09.G.i; 09.G.j; 09.G.k; 09.G.l; 09.H.a; 09.H.b; 09.H.c; 09.H.d; 09.H.e; 09.H.f; 09.H.g; 09.H.h; 09.H.i; 09.H.j; 09.H.k; 09.H.l; 09.I.a; 09.I.b; 09.I.c; 09.I.d; 09.I.e; 09.I.f; 09.I.g; 09.I.h; 09.I.i; 09.I.j; 09.I.k; 09.I.l; 10.A.a; 10.A.b; 10.A.c; 10.A.d; 10.A.e; 10.A.f; 10.B.a; 10.B.b; 10.B.c; 10.B.d; 10.B.e; 10.B.f; 10.C.a; 10.C.b; 10.C.c; 10.C.d; 10.C.e; 10.C.f; 10.D.a; 10.D.b; 10.D.c; 10.D.d; 10.D.e; 10.D.f; 11.A.a; 11.A.b; 11.A.c; 11.A.d; 11.A.e; 11.A.f; 11.B.a; 11.B.b; 11.B.c; 11.B.d; 11.B.e; 11.B.f; 11.C.a; 11.C.b; 11.C.c; 11.C.d; 11.C.e; 11.C.f; 11.D.a; 11.D.b; 11.D.c; 11.D.d; 11.D.e; 11.D.f; 12.A.a; 12.A.b; 12.A.c; 12.A.d; 12.A.e; 12.A.f; 12.A.g; 12.A.h; 12.A.i; 12.A.j; 12.A.k; 12.A.l; 12.B.a; 12.B.b; 12.B.c; 12.B.d; 12.B.e; 12.B.f; 12.B.g; 12.B.h; 12.B.i; 12.B.j; 12.B.k; 12.B.l; 12.C.a; 12.C.b; 12.C.c; 12.C.d; 12.C.e; 12.C.f; 12.C.g; 12.C.h; 12.C.i; 12.C.j; 12.C.k; 12.C.l; 12.D.a; 12.D.b; 12.D.c; 12.D.d; 12.D.e; 12.D.f; 12.D.g; 12.D.h; 12.D.i; 12.D.j; 12.D.k; 12.D.l; 12.E.a; 12.E.b; 12.E.c; 12.E.d; 12.E.e; 12.E.f; 12.E.g; 12.E.h; 12.E.i; 12.E.j; 12.E.k; 12.E.l; 12.F.a; 12.F.b; 12.F.c; 12.F.d; 12.F.e; 12.F.f; 12.F.g; 12.F.h; 12.F.i; 12.F.j; 12.F.k; 12.F.l; 12.G.a; 12.G.b; 12.G.c; 12.G.d; 12.G.e; 12.G.f; 12.G.g; 12.G.h; 12.G.i; 12.G.j; 12.G.k; 12.G.l; 12.H.a; 12.H.b; 12.H.c; 12.H.d; 12.H.e; 12.H.f; 12.H.g; 12.H.h; 12.H.i; 12.H.j; 12.H.k; 12.H.l; 12.I.a; 12.I.b; 12.I.c; 12.I.d; 12.I.e; 12.I.f; 12.I.g; 12.I.h; 12.I.i; 12.I.j; 12.I.k; 12.I.l; 13.A.a; 13.A.b; 13.A.c; 13.A.d; 13.A.e; 13.A.f; 13.B.a; 13.B.b; 13.B.c; 13.B.d; 13.B.e; 13.B.f; 13.C.a; 13.C.b; 13.C.c; 13.C.d; 13.C.e; 13.C.f; 13.D.a; 13.D.b; 13.D.c; 13.D.d; 13.D.e; 13.D.f; 14.A.a; 14.A.b; 14.A.c; 14.A.d; 14.A.e; 14.A.f; 14.A.g; 14.A.h; 14.A.i; 14.A.j; 14.A.k; 14.A.l; 14.B.a; 14.B.b; 14.B.c; 14.B.d; 14.B.e; 14.B.f; 14.B.g; 14.B.h; 14.B.i; 14.B.j; 14.B.k; 14.B.l; 14.C.a; 14.C.b; 14.C.c; 14.C.d; 14.C.e; 14.C.f; 14.C.g; 14.C.h; 14.C.i; 14.C.j; 14.C.k; 14.C.l; 14.D.a; 14.D.b; 14.D.c; 14.D.d; 14.D.e; 14.D.f; 14.D.g; 14.D.h; 14.D.i; 14.D.j; 14.D.k; 14.D.l; 14.E.a; 14.E.b; 14.E.c; 14.E.d; 14.E.e; 14.E.f; 14.E.g; 14.E.h; 14.E.i; 14.E.j; 14.E.k; 14.E.l; 14.F.a; 14.F.b; 14.F.c; 14.F.d; 14.F.e; 14.F.f; 14.F.g; 14.F.h; 14.F.i; 14.F.j; 14.F.k; 14.F.l; 14.G.a; 14.G.b; 14.G.c; 14.G.d; 14.G.e; 14.G.f; 14.G.g; 14.G.h; 14.G.i; 14.G.j; 14.G.k; 14.G.l; 14.H.a; 14.H.b; 14.H.c; 14.H.d; 14.H.e; 14.H.f; 14.H.g; 14.H.h; 14.H.i; 14.H.j; 14.H.k; 14.H.l; 14.I.a; 14.I.b; 14.I.c; 14.I.d; 14.I.e; 14.I.f; 14.I.g; 14.I.h; 14.I.i; 14.I.j; 14.I.k; 14.I.l; 15.A.a; 15.A.b; 15.A.c; 15.A.d; 15.A.e; 15.A.f; 15.B.a; 15.B.b; 15.B.c; 15.B.d; 15.B.e; 15.B.f; 15.C.a; 15.C.b; 15.C.c; 15.C.d; 15.C.e; 15.C.f; 15.D.a; 15.D.b; 15.D.c; 15.D.d; 15.D.e; 15.D.f; 16.A.a; 16.A.b; 16.A.c; 16.A.d; 16.A.e; 16.A.f; 16.B.a; 16.B.b; 16.B.c; 16.B.d; 16.B.e; 16.B.f; 16.C.a; 16.C.b; 16.C.c; 16.C.d; 16.C.e; 16.C.f; 16.D.a; 16.D.b; 16.D.c; 16.D.d; 16.D.e; 16.D.f; 17.A.a; 17.A.b; 17.A.c; 17.A.d; 17.A.e; 17.A.f; 17.B.a; 17.B.b; 17.B.c; 17.B.d; 17.B.e; 17.B.f; 17.C.a; 17.C.b; 17.C.c; 17.C.d; 17.C.e; 17.C.f; 17.D.a; 17.D.b; 17.D.c; 17.D.d; 17.D.e; 17.D.f.

Utilities

The compounds of this invention are useful per se or as intermediates in the preparation of polymers having a wide variety of diagnostic, therapeutic and industrial utilities.

The compounds are useful in the preparation of polyphosphonate flame retardants. The compounds of this invention that contain nonresonant sites of unsaturation, e.g., enolpyran and $R^3$ or Z groups, are incorporated into polyvinyl polymers by methods or analogous methods heretofore employed with known vinylphosphonates. The compounds of this invention that do not already contain vinyl groups or the like are useful nonetheless as intermediates preparing vinylphosphonate monomers. These monomers are copolymerized with vinyl resins by free radical catalysis methods already known per se, e.g., by use of persulfate or electron beam. Other methods of incorporation of the compounds of this invention into polymeric resins will be readily apparent to the skilled artisan, so it is not necessary to use vinyl intermediates.

The compounds of this invention are useful as intermediates in preparing labelled oligonucleotide probes or, when Y is an oligonucleotide, are directly useful in assays for target nucleic acid sequences. Typically, the phosphonate group of the compounds of this invention is covalently bonded to the terminus of an oligonucleotide having a predetermined sequence, although any hydroxyl group is useful for this purpose. The structure or sequence of the oligonucleotide is not important except insofar as it is binding-competent for its complementary sequence. Many oligonucleotides having this property are well known, e.g. conventional phosphodiester or phosphorothioate oligonucleotides.

The compounds of this invention generally will be terminally incorporated into the oligonucleotide. If they contain a free hydroxyl group (ordinarily one or both of the $R^1$ groups or Z) linked to the pyran or (preferably) the furan ring, they optionally are incorporated internally into the sequence of the oligonucleotide. Terminally incorporated diphosphoryl compounds of this invention which contain no free hydroxyl capable of participating in chain elongation also are useful in DNA sequencing in essentially the same manner as deoxyNTPs have been used in the past (see example 8 of U.S. Pat. No. 5,276,143). The nucleotide analogues of the invention (when diphosphorylated) are useful as chain terminators for dideoxynucleotide-type DNA sequencing protocols, provided that the nucleotide analogue lacks a free hydroxyl group suitable for polymerase mediated chain elongation. These compounds will not have a free hydroxyl group at $R^{1a}$, $R^{1b}$ or Z and do not possess a cyclic structure incorporating the phosphorus atom (although such excluded structures can be intermediates). The nucleotide analogue is included in a kit with other reagents (such as klenow polymerase or T4 polymerase, dNTPs, etc) needed for DNA sequencing (Otvos, et al, "Nucl. Acids Res." 15:1763–1777 (1987).

If the oligonucleotide-incorporated compound of this invention is binding-competent for its complementary sequence, i.e., if it is capable of base-pairing, then this nucleotide monomer will participate in hybridization. It is not necessary, however, that the incorporated nucleotide analogue of this invention base pair or otherwise participate in hybridization. If it is located at the terminus of the oligonucleotide it will be useful as an immunological recognition site to detect the presence of the oligonucleotide when used as a probe or as a linker for a detectable group.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups in the compounds of this invention are suitable for use in cross-linking. For example, the phosphonic acid is used to form esters with alcohols or amides with amines. The Z, $R^{1a}$ or $R^{1b}$ groups substituted with OH, azido (which is reduced to amino if desired before cross-linking), CN or halo are suitable sites. Similarly, the amino, halo, acyl and other reactive sites (e.g., the 8-purine position) found on group B are suitable. Suitable protection of reactive groups will be used where necessary while assembling the cross-linked reagent. In general, the compounds here are used by linking them through phosphonic acid to the hydroxyl or amino groups of the linking partner in the same fashion as shown herein and covalently bonded to the other binding partner through a Z, B, $R^{1a}$ or $R^{1b}$ group. For example a first binding partner such as a steroid hormone is esterified to the phosphortic acid of this invention and then this conjugate is cross-linked to cyanogen bromide activated Sepaharose, whereby immobilized steroid is obtained. Other chemistries for conjugation are well known. See for example Maggio, "Enzyme-Immunoassay" (CRC, 1988, pp 71–135) and references cited therein.

The oligonucleotides of this invention are labelled with any conventional detectable label, e.g. a fluorescent moiety such as fluorescein, radioisotopes such as $C_{14}$ or $H_3$, stable free radicals, avidin, biotin and the like all of which previously have been used as labels for immunoassays or diagnostic probes. The label will be present on the oligonucleotide or on the residue of the nucleotide analogue of this invention. Suitable labelling methods are well known and are readily used with reactive groups such as hydroxyl, allyl and the like. A simple method is to label the compound of this invention with $H_3$ by proton exchange. The compounds also are biotinylated using conventional methods. See for instance U.S. Pat. No. 5,276,143 for analogous structures. However, the oligonucleotides of this invention also are useful directly in diagnostic probe assays without an exogenous detectable label. In one embodiment of this alternative, antibodies are raised against the nucleotide analogues of this invention. Such antibodies (which in turn are labelled or used in a double antibody configuration) bind to the analogue of this invention and thereby are useful in detecting the presence of the bound probe that incorporates the nucleotide analogue of this invention.

The compounds of the invention, particularly those in which the phosphonate and base have the same absolute stereochemistry, are useful for treatment of microbial infections, for treatment of tumors or for other indications described below. Microbial infections treatable by the compounds of this invention include viruses, parasites, yeasts and fungi, but it is believed that the compounds are most effective against viruses, which constitutes the preferred utility. Exemplary viral infections include infections caused by DNA or RNA viruses including herpesviruses (CMV, HSV 1, HSV 2, EBV, varicella zoster virus, bovid herpesvirus type 1, equid herpesvirus type 1), papillomaviruses (HPV types 1–55; carcinogenic HPV), flaviviruses (including African swine fever virus and Japanese encephalitis virus), togaviruses (including Venezuelan equine encephalomyelitis virus), influenza viruses (types A–C), retroviruses (HIV 1, HIV 2, HTLV I, HTLV II, SIV, HBV, FeLV, FIV, MoMSV), adenoviruses (types 1–8), poxviruses (vaccinia virus), enteroviruses (polio virus type 1–3, hepatitis A virus), gastroenteritis viruses (Norwalk viruses, rotaviruses), hantaviruses (Hantaan virus), papovaviruses, rhinoviruses, parainfluinza virus types 1–4, rabies virus, RSV, hepatitis viruses A, B, C and E, and the like. The structure (1) compounds in which Z is $CH_2OR^2$ are believed to be most effective against DNA viruses, while those in which Z is $CH_3$, $CH=CH_2$, $CH_2N_3$, $C\equiv CH$, or haloalkyl are believed to be most effective against RNA and retroviruses. Compounds in which Z is H are believed to be effective to at least some degree against DNA, RNA and retroviruses. Hepatitis B viruses and HIV are believed to be most effectively treated by the β-L compounds of this invention.

The antiviral activity of individual nucleotide analogues is determined by routine assay of antiviral (or other antimicrobial) activity using enzyme inhibition assays, tissue culture assays, animal model assays and the like as will be understood by those skilled in the art.

Protozoan parasite infections are treated using the compounds of the invention. The term protozoa includes those members of the subphyla Sarcomastigophora and Sporozoa of the phylum Protozoa. More particularly, the term protozoa as used herein includes genera of parasitic protozoa which are important to man because they either cause disease in man or in his domestic animals. These genera for the most part are classified in the superclass Mastighphora of the subphylum Sarcomastigophora and the class Telosporea of the subphylum Sporozoa in the classification according to Baker (1969). Illustrative genera of these parasitic protozoa include Histomonas, Pneumocystis, Trypanosoma, Giardia, Trichomonas, Eimeria, Isopora, Leishmania, Entamoeba, Toxoplasma and Plasmodium. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E., et al, "Mol. Biochem. Parasitol" 47:43–50 (1991)). The compounds in which Z is $CH_2OR^2$ and B is 3-deazaadenine are particularly interesting for malarial parasites.

Nucleoside analogues of the invention are used to treat yeast or fungal infections caused by *Candida glabrata, Candida tropicalis, Candida albicans*, and other Candida species Cryptococcus species including *Cryptococcus neoformans*, Blastomyces species including *Blastomyces dermatidis*, Torulopsis species including *Torulopsis glabrata*, Coccidioides species including *Coccidioides immitis*, Aspergillus species and the like.

The therapeutically useful compounds of this invention in which hydroxyl or amino groups are protected are useful as oral or sustained release forms. In these uses the protecting group is removed in vivo, e.g., hydrolyzed or oxidized, so as to yield the free amino or hydroxyl. This is necessary in the case of the phosphonate hydroxyl groups. Suitable esters or amidates for this utility are selected based on the substrate specificity of esterases and/or carboxypeptidases expected to be found within cells where precursor hydrolysis is desired. To the extent that the specificity of these enzymes is unknown, one will screen a plurality of nucleotide analogues of this invention until the desired substrate specificity is found. This will be apparent from the appearance of free phosphonate or of antimicrobial activity. One generally selects compounds that are (i) not hydrolyzed or hydrolyzed comparatively slowly in the upper gut, (ii) gut and cell permeable and (iii) hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, optionally are treated with a precursor that is hydrolyzed at substantially the same rate and to substantially the same degree in all tissues. Assays known in the art are suitable for these purposes, including intestinal lumen stability, cell permeation, liver homogenate stability and plasma stability assays. These assays are used to determine the bioavailability characteristics of the precursors. However, even if the derivatives are not converted in vivo they remain useful as chemical intermediates.

The nucleotide analogues of the invention also can be (1) applied to tissue culture systems to eliminate or reduce viral spread or growth during the production of biopharmaceuticals or other products (such as proteins or vaccines), (2) used to eliminate or reduce viral spread or growth in clinical samples (such as blood), and (3) used to stop growth of tissue culture or bacterial cells (using toxic amounts of compound) while leaving the cells to carry on with protein production.

Pharmaceutical formulations. Compounds of the invention and their physiologically acceptable salts (hereafter collectively referred to as the active ingredients) are formulated for administration by any route appropriate to the condition to be treated. The compounds and formulations preferably will be sterile.

The active ingredients are placed into pharmaceutical formulations. The formulations, both for veterinary and for human use, comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient.

The formulations conveniently are presented in unit dosage form and may be prepared by any of the methods well known in the art of pharmacy. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

For external infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), typically 0.2 to 15% w/w and most typically 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The oily phase of the emulsions of this invention may be constituted from known ingredients in a known manner. This phase may comprise an emulsifier alone, or a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate. Suitable oils or fats include straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate or 2-ethylhexyl palmitate. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is typically is present in such formulations in a concentration of 0.01 to 20% by weight.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by rapid inhalation through the nasal passage from a container of the powder. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

The present invention further provides veterinary compositions comprising at least one active ingredient as above defined together with a veterinary carrier therefor. Veterinary carriers are materials for administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention in which the release of the active ingredient is controlled and regulated to allow less frequent dosing or to improve the pharmacokinetic or toxicity profile of a given compound. In general, the compounds are administered from controlled release systems such as the intravitreal implant of WO 92/14450 or U.S. Pat. No. 5,098,443, or the matrices of U.S. Pat. No. 4,740,365 or U.S. Pat. No. 5,141,752, although many others are known and are suitable for use herein.

Therapeutic Administration. Suitable routes for administration include oral, rectal, nasal, topical (including ocular, buccal and sublingual), vaginal and parenteral (including subcutaneous, intramuscular, intravitreal, intravenous, intradermal, intrathecal and epidural). The preferred route of administration will depend upon the condition of the patient, the toxicity of the compound and the site of infection, among other considerations known to the clinician.

For each of the above-indicated theapeutic indications the amount required of an active ingredient (as above defined) will depend upon a number of factors including the severity of the condition to be treated, the infectious agent, whether the use is prophylactic or to treat an acute infection, the site of infection or pathology (e.g. CMV retinitis is treated systemically or by intravitreal injection) and other factors ultimately at the discretion of the attending physician or veterinarian. In general, however, a suitable dose for consideration by the clinician will be in the range of analogous methoxyphosphonates (see supra), taking into account differences in potency, generally 0.1 to 250 mg per kilogram bodyweight of recipient per dose (including active ingredient(s) in a range between 0.1 mg and 250 mg/Kg/dose in increments of 0.5 mg/Kg/dose such as 2.5 mg/Kg/dose, 3.0 mg/Kg/dose, 3.5 mg/Kg/dose, etc), typically in the range 0.5 to 50 mg per kilogram body weight per dose and most usually in the range 1 to 15 mg per kilogram body weight per dose. Unless otherwise indicated all weights of active ingredient are calculated as a compound of structure (1) wherein Y is not a polymer.

The desired dose is administered at appropriate intervals in unit dosage forms, usually with a relatively higher induction dose and lower, less frequent maintenance doses. The compounds also are used prophylactically, for example, by administration on about from 1 to 7 days before viral infection. HPV tumors or growths and herpes lesions often are treated topically, either by local injection or by topical gels, ointments or the like.

Compounds such as those of structures (2), (3), and (4) generally are expected to have a higher oral bioavailabitity than the corresponding uncyclized nucleotide analogue and/or exhibit reduced toxicity when compared with the same dose of the corresponding uncyclized nucleotide analogue. Doses will be adjusted accordingly.

The compounds of the invention optionally are employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions. These include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5, 1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA and HPMPDAP, (2R,5R)-9-[tetrahydro-5-(phosphonomethoxy)-2-furanyl]adenine, (2R,5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like), β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy)pentane), 9-deazainosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzylthioinosine, immunomodulators such as FK506, cyclosporin A, thymosin α-1, cytokines including TNF and TGF-β, interferons including IFN-α, IFN-β and IFN-γ, interleukins including interleukin 1, 2, 3, 4, 5, 6, 7, 8, 10, 12, 13, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and, particularly in treatment of HIV, cotherapy with IFN-α, IL-2 or IL-12.

Immunogens and Antibodies. The compounds of this invention are used as immunogens to prepare antibodies capable of binding specifically to the compounds or their metabolic products. The immunogenic compositions are useful as intermediates in the preparation of antibodies for use in diagnostic or quality control assays for the compounds or their metabolic products. The antibodies are useful for measuring the presence, absence or amounts of the compounds by any convenient homogenous or heterogenous procedure such as fluorescence polarization immunoassay, fluorescence immunoassay (using fluorescent labels such as fluorescein and the like), radioimmunoassay, enzyme immunoassay (using enzyme indicators such as alkaline phosphatase, horseradish peroxidase, glucose oxidase, urease and the like) and nephelometric inhibition assay by described methods (WO 92/22639). Competitive-type assays usually require the antibody, and a tracer (such as a fluorescent or radio label) conjugated to the compound to be assayed. The antibodies directed against the compounds of this invention desirably will not cross-react with naturally-occurring nucleotides or nucleosides.

The immunogens of this invention contain the precursor or hydrolytic products in association with an immunogenic substance such as a protein or peptide. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides.

Methods for the manufacture hapten immunogens are conventional per se, and are useful here, taking into account the functional groups that are available for cross-linking. The polypeptide immunogen (or a polypeptide that is desired to be made immunogenic by cross-linking to a compound of this invention) may be conjugated to a site on the heterocyclic base rather than to the phosphonate moiety. In general, the site will be an amino group located on the purine or pyrimidine moiety of the nucleotide phosphonate, at the 5 position of pyrimidines (such as cytosine or uracil), at the 1 position of purines (such as adenosine or guanine) or through a furan or pyran ring hydroxyl group (usually at the $R^{1a}$, $R^{1b}$ or Z positions). Alternatively, the precursor compound is cross-linked through the phosphonate, typically by amidation or esterification of the phosphonate by the polypeptide itself or by a cross-linking functionality covalently bonded to the polypeptide, whereby Y is an immunogenic protein having more than 50 amino acid residues, usually less than 1000. The conjugates are prepared in conventional fashion. For example, N-hydroxysuccinimide, succinic anhydride or alkN=C=Nalk are useful in preparing the conjugates of this invention. Animals typically are immunized against the immunogenic conjugates and monoclonal antibodies prepared in conventional fashion.

Synthetic Methods

The Table 1 saturated compounds are made by the following scheme 1. Table 1 unsaturated compounds are made by scheme 2 or straight-forward variations thereof. Scheme 2 also is readily adapted to make saturated Table 1 compounds by adding the $R^1$ groups across the double bond, for example, via expoxidation, hydroxylation, reduction or halogenation. Table 1 compounds having $R^{1a}$ and $R^{1b}$ joined with the heterocyclic ring to form cyclopropyl are produced by carbene addition across the double bond of the corresponding unsaturated ring. Table 1 compound 14 is made by the method of scheme 3a. Compounds of this invention in which Y is $CH_3$, H, $CH=CH_2$, alkylhalo, $CH_2N_3$ or C≡CH are made by the procedures of scheme 3 or variations thereof that will be apparent to the ordinary artisan in this field. These schemes are used with any base B, provided that the base is suitably protected during synthesis. Other compounds of this invention are made by variations of these schemes that will be readily apparent to those skilled in the art.

These schemes employ conventional abbreviations for known reagents.

Scheme 1

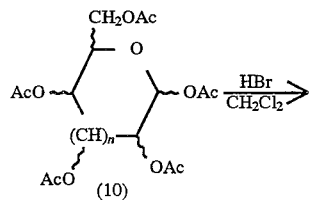

n = 1 or 0;
alternatively, H replaces acetate at the 2-, 3-
and/or 6-positions (and/or 5-acetate if n = 0)

-continued
Scheme 1
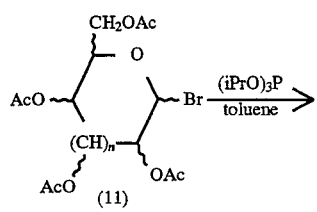
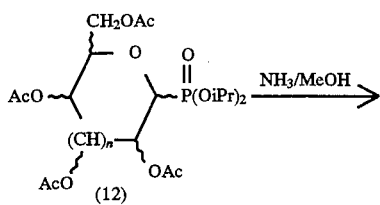
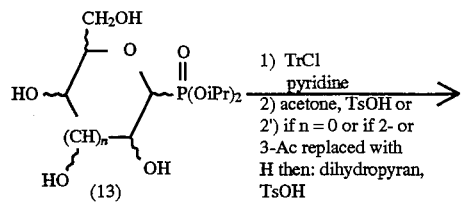
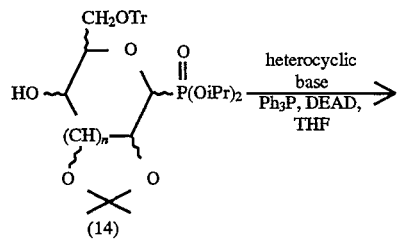
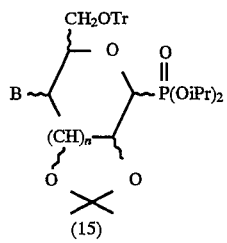
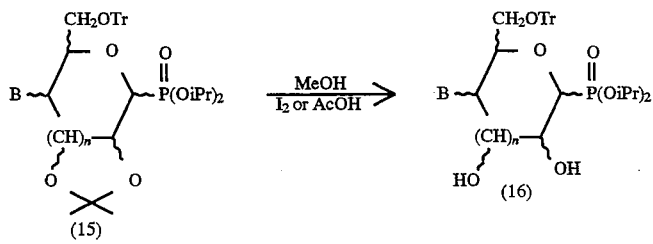
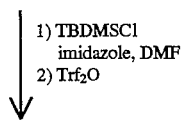

-continued
Scheme 1
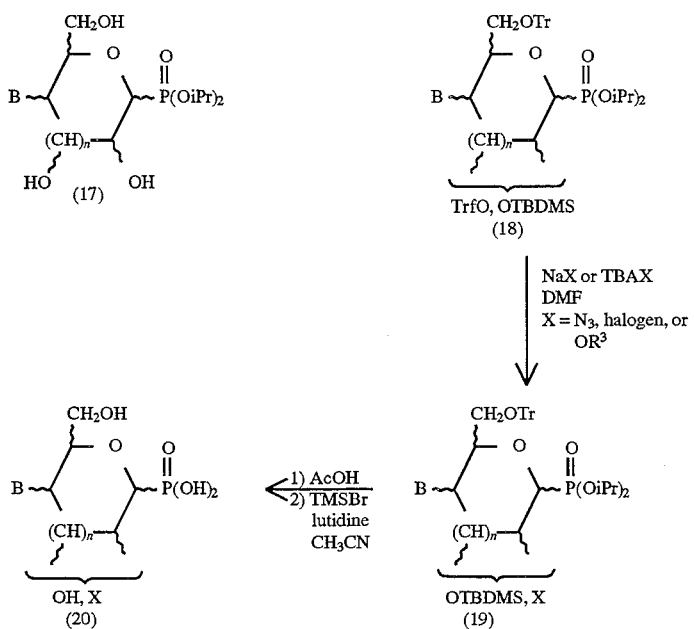
Scheme 2
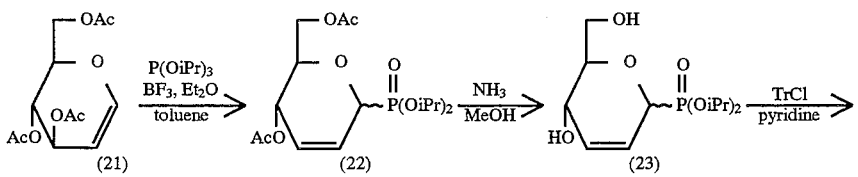
commercially available
tri-O-acetyl-D-glucal -continued
Scheme 2
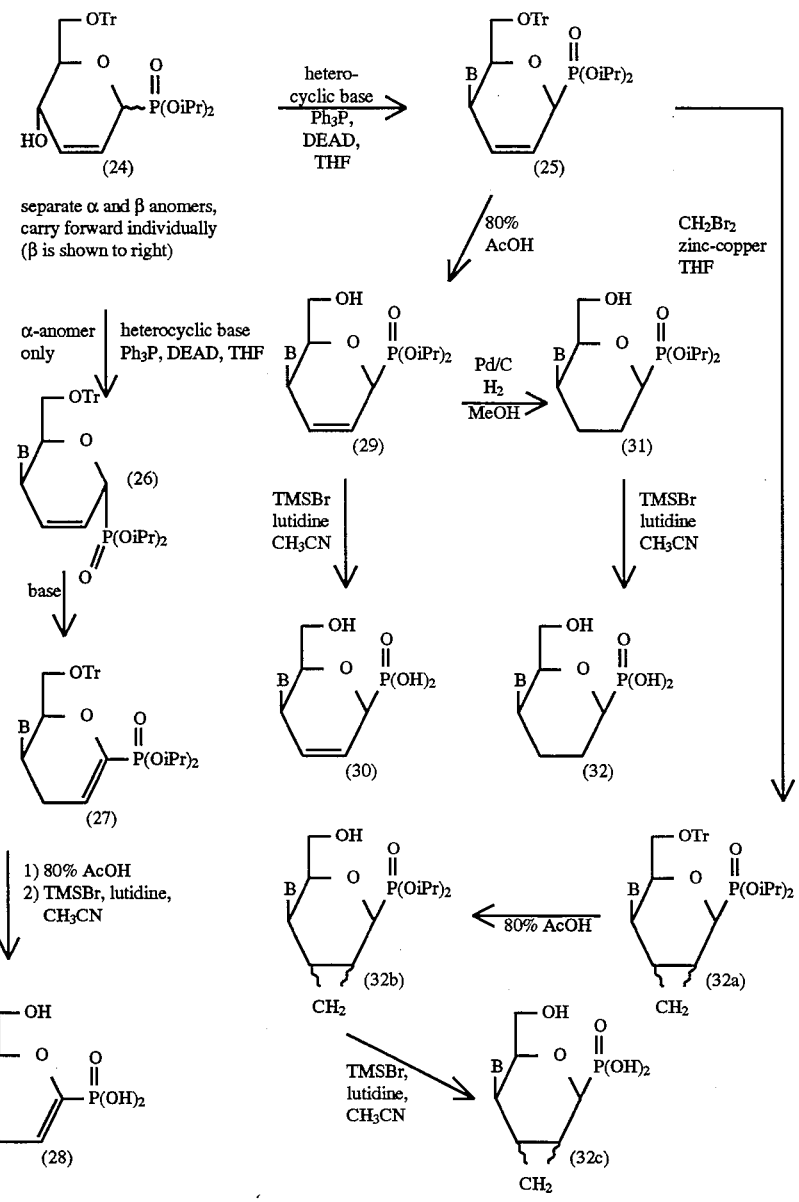
Scheme 3
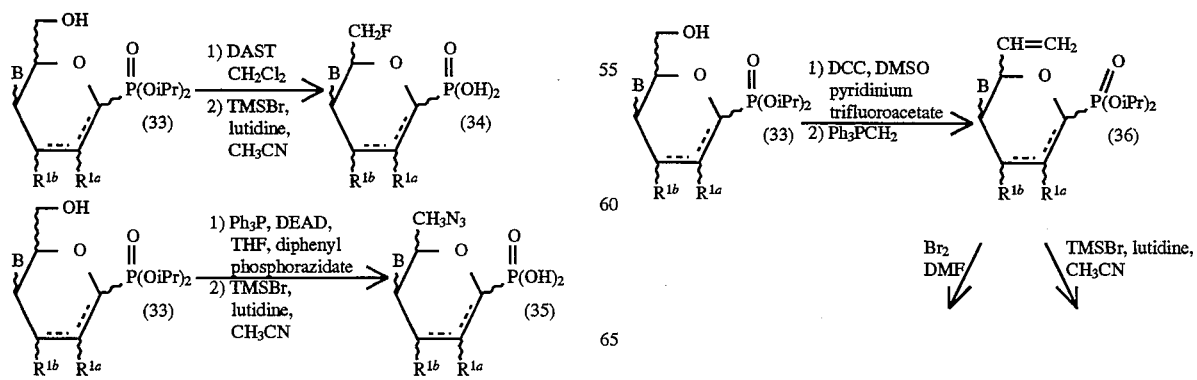
-continued
Scheme 3

Scheme 3
-continued

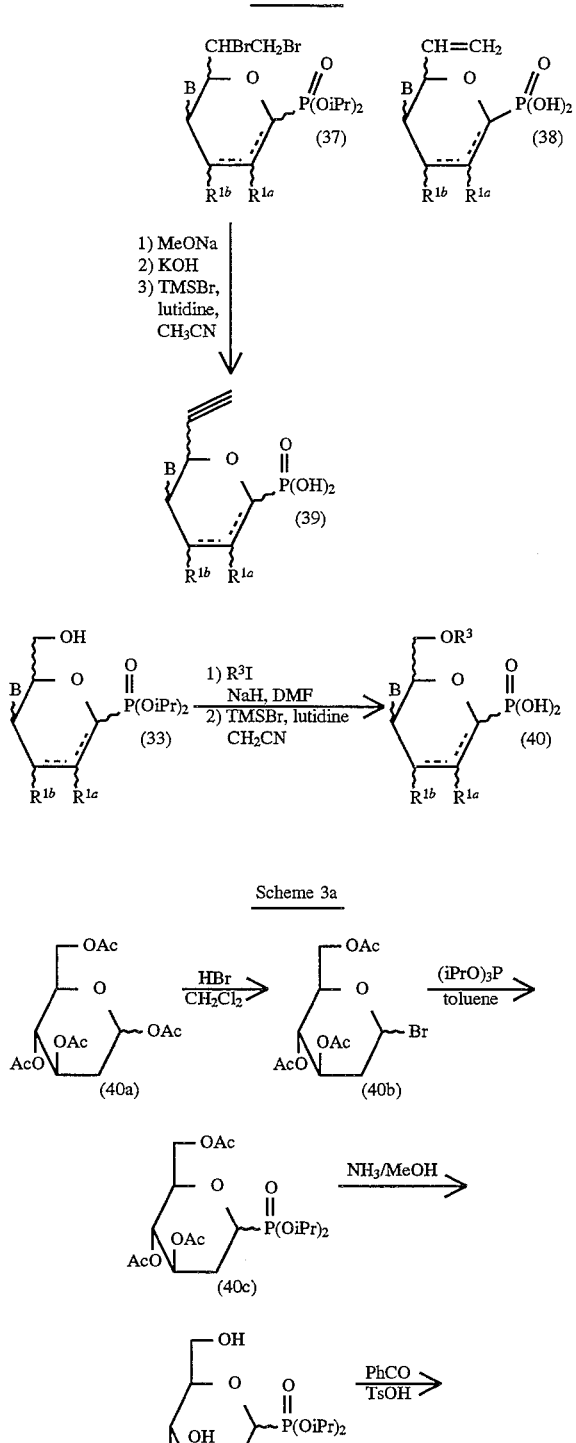

Scheme 3a

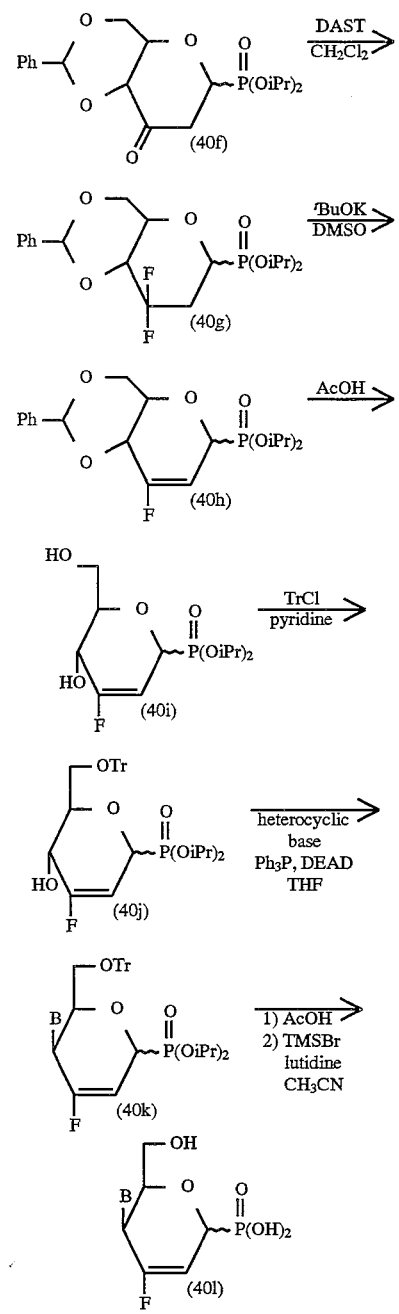

The step in scheme 2 where (21) is converted to (22) by double bond migration is inventive. A protected, Z-substituted pyran (I) is treated in accord with this step, and any Lewis Acid (e.g. HCl, $ZnCl_2$, $BF_3 \cdot OEt_2$, $SnCl_3$, and the like) is suitable. The reaction solvent is not critical; any high boiling (>100° C.) organic solvent is satisfactory. The phosphite PRT group is not critical and usually falls within $R^3$, typically lower alkyl ($C_1$–$C_6$) and preferably iPr or ethyl.

Also inventive is the step in scheme 2 where the double bond in (26) migrates to the 1–2 position as shown for compound (27). A protected, Z-substituted pyran (III) is treated with any base, whether organic or inorganic, whereupon the double bond spontaneously migrates to a position α to the phosphate atom. The β anomers require a stronger base than do the α anomers. This method has the additional advantage of removing benzyl protecting groups from any exocyclic amino groups of B. PRT in this method generally is selected from $R^3$ as noted in the previous paragraph.

The various diastereomers falling within the scope of this invention are readily produced from the corresponding sugars using the foregoing schemes. For example,

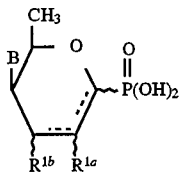 (41)

is produced from D-rhamnal,

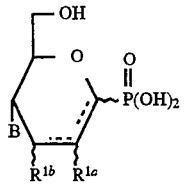 (42)

is produced from D-glactal,

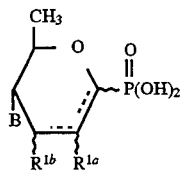 (43)

is produced by 6-deoxy-D-glactal; and

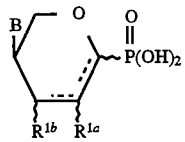 (43a)

is produced from D-xylal.

In general, other suitable sugars or unsaturated analogues thereof will be readily apparent starting materials. L-isomers of the claimed compounds are derived from the corresponding L-sugars or analogues thereof, taking into account the stereochemical shift upon substitution by heterocylic base (see scheme 2). Aside from the foregoing, the following Table 6 lists each of the sugars from which the Table 1 structures are derived.

TABLE 6

| | |
|---|---|
| 1. | D-allose |
| 2. | D-glucose |
| 3. | D-altrose |
| 4. | D-mannose |
| 5. | D-glucal |
| 6. | L-galactal |
| 7. | D-glucal |
| 8. | L-galactal |
| 9. | D-glucal |
| 10. | D-galactal |
| 11. | L-glucal |
| 12. | L-galactal |
| 13. | D-glucal |
| 14. | 2-deoxy-D-glucose |
| 15. | D-galactal |

TABLE 6-continued

| | |
|---|---|
| 16. | L-galactal |
| 17. | L-glucal |
| 18. | D-gulose |
| 19. | L-galactose |
| 20. | D-allose |
| 21. | D-galactose |
| 22. | L-glucose |
| 23. | L-allose |
| 24. | L-gulose |
| 25. | D-glucose |
| 26. | L-mannose |
| 27. | L-gulose |
| 28. | D-allose |
| 29. | D-glucose |
| 30. | D-altrose |
| 31. | L-idose |
| 32. | L-gulose |
| 33. | L-talose |
| 34. | L-galactose |
| 35. | D-ribose |
| 36. | L-lyxose |
| 37. | D-xylose |
| 38. | L-xylose |
| 39. | D-lyxose |
| 40. | D-arabinose |
| 41. | D-xylose |
| 42. | D-lyxose |
| 43. | D-arabinose |
| 44. | D-ribose |
| 45. | L-arabinose |
| 46. | L-ribose |
| 47. | L-xylose |
| 48. | L-arabinose |
| 49. | L-ribose |
| 50. | L-xylose |

If racemization occurs during any step in the synthesis the various diastereomers at chiral atoms 1–6 are separated using standard methods such as HPLC, RPLC or crystallization.

It is also within the scope of this invention to use compounds falling within the claims as intermediates for other claimed compounds, for example as shown in scheme 3a or as will be readily apparent to those skilled in the art, e.g. interconversion of heterocyclic bases.

Bis amidate synthesis. Synthesis of bis-phosphoroamidate nucleotide analogues of structure (1) where Y groups are the same and are an amino acid, dipeptide, tripepride or polypeptide is accomplished by conversion of the phosphonic acid nucleotide analogue to the corresponding bis-phosphoroamidate compound. The diacid is suspended in approximately 2 equivalents of the Y reactant in a solvent such as dry pyridine or DMF (dimethylformamide) optionally containing a non-nucleophilic organic base such as triethylamine (about 3 to 10 equivalents). The dehydration step is accomplished by modification of a described reaction (Mukaiyama, T. et al, "J. Am. Chem. Soc." 94:8528–8532 (1972)) by adding a 1:1 mixture of triphenylphosphine (reg. no. 603-35-0; Aldrich) and 2,2'-dipyridyl disulfide (2 to 4 equivalents; reg. no. 2127-03-9; Aldrich) in pyridine to the nucleotide analogue/amino acid mixture and (a) stirring at room temperature for about 4 to 16 hours or (b) heating to 60° C. to 100° C. (including any temperature in one degree C. increments between 60° and 100° C. such as 70°, 80° or 90° C.) for about 4 to 16 hours. The resulting reaction mixture is then concentrated and the final bis-amidate product is recovered and purified by conventional methods.

An alternative reaction suitable for synthesizing most amidate compounds is to convert the phosphonate to the corresponding chloridate by reaction with thionyl chloride in solvent (DMF) as described in EP 481 214. An amino acid, dipeptide or other molecule bearing a free amine is then reacted with the chloridate to yield the corresponding mono-amidate (where the phosphonate is cyclized) or bis-amidate.

Synthesis of compounds of structure (1) having amino acids that contain amino, guanidino or carboxyl groups (such as lys, arg, his, asn, gln, lys-lys, arg-arg, lys-arg and the like) is accomplished by the same method, but using protected amine or carboxyl groups. After synthesis of the protected amidate compound, the protecting groups are removed by conventional methods. Suitable protecting groups are well known (see supra) and include acid labile groups such as p-tosyl, BOC (t-butoxycarbonyl) and FMOC (fluorene methoxycarbonyl) for protecting amine groups. Groups such as t-butyl, methyl, ethyl, benzyl and the like can be used to protect carboxyl groups. These groups are removed under acid, base or hydrogenolysis conditions or are removed with an esterase according to conventional methods.

Synthesis of compounds of structure (1) having amino acids such as tyr, cys, ser and thr is accomplished by optionally protecting hydroxyl or thiol groups using protecting groups know in the art. For example, the hydroxyl group of ser, thr or tyr can be protected using benzyl, ethyl and the like and the thiol group of cys can be protected using trityl, p-methylbenzyl and the like. The choice of a protecting group will depend on the stability of the bis-amidate toward conditions used to remove a particular protecting group. Appropriate protecting groups can be selected or determined by the skilled artisan using routine methods.

Synthesis of compounds in which Y is N-alkylamine is accomplished essentially as described by Saito, "Chem. Pharm. Bull." 39:3207 (1991).

Amidate-ester synthesis. Synthesis of mixed amidate-ester nucleotide analogues where one Y is an amino acid ester and the other is a group of the formula $OR^3$ is accomplished by conversion of the nucleotide analogue di- or bis-ester to the corresponding mono ester by treatment with a base such as ammonia to remove one ester group. The resulting mono ester is then converted to a mixed amidate-ester as described for synthesis of bis amidate compounds.

Oligonucleotides. Compounds of this invention where Y is an oligonucleotide are prepared from parental monomers in which Y is OH. The monomers are converted to the reactive intermediate using conventional chemistry, for example the method of Uhlmann et al., "Chemical Reviews" 90(4):543 at 553, part c and FIG. 23 (1990) or Mazur et al., "Tet. Let." 40(20):3949 at scheme (1) and page 3955 (1984). For example, an oligonucleotide chain is synthesized on a matrix such as controlled pore glass in the 3'-5' or 5' to 3' direction, whereby the 3' or 5' ends, respectively, of the oligonucleotide are bonded to the matrix and the oligonucleotide is protected except for the terminal 5' or 3' hydroxyl, respectively, of the last nucleotide. The protected o-chlorophenyl derivative of the structure 1 compound is prepared, analogous to the starting material shown in FIG. 23 of Uhlmann et al. This is covalently bonded to a terminal OH of the oligonucleotide using the Uhlmann et al. method.

Alternatively, the compound of this invention is converted to the intermediate that is analogous to compound 12 of Mazur et al. This analogue is added to the oligonucleotide using essentially the dinucleotide preparative chemistry shown on page 3955 of Mazur et al. The pyridinium salt of the compound of this invention (without free hydroxyl groups) is condensed with the free 5' or 3' end of the otherwise protected oligonucleotide in the same way Mazur et al. condense phosphonate 12 with a second nucleoside unit using DCC in dry pyridine in the presence of Dowex 50.

After reaction by either method, the oligonucleotide is separated from the matrix (if present during the addition of the compound of this invention) and deprotected.

Alternatively, the compounds of this invention are chemically converted to nucleotide triphosphate analogues. This is accomplished using known reactions, for example reaction of the phosphonate with tris(tri-n-butylammonium) pyrophosphate in DMF. The resulting deoxyNTP or NTP analogue (where $R^{1a}$ or $R^{1b}$ are unprotected hydroxy) is incorporated enzymatically into the oligonucleotide using ligase or polymerase.

Esters. Hydroxy esters, especially at the phosphonate, are generally synthesized as known in the art or as shown below. For instance, see the methods described in EP 481 214 or Mukaiyama, T. et al, "J. Am. Chem. Soc." 94:8528–8532 (1972). Dialkyl phosphonate esters are synthesized via conversion of a dichlorophosphonate chloridate (Quast, H. et al, "Synthesis" 7:489–490 (1974); Quast, H. et al, "Synthesis" 7:490 (1974); Moedritzer, K. et al, "Synth. Reac. Inorg. Met.-Org. Chem." 5:417–27 (1974); Stowell, M. H. B., et al, "Tet. Lett." 31:3261–3262 (1990)) to a corresponding dialkylester (or dialkylamide) by reaction with alcohols (or amines). Monoalkylesters (or mono alkylamides) are obtained by hydrolysis of the disubstituted phosphonate in base (NaOH, KOH and the like). Disubstituted diacyloxyalkyl phosphonates are obtained by reaction of the unsubstituted phosphonate with a substituted chloromethyl ester ($R^3C(O)OCH(R^3)Cl$). A corresponding monosubstituted acyloxyalkyl phosphonate is obtained by hydrolysis in acid or base.

Bis esters having $R^3$ groups such as aryl, substituted aryl, alkaryl or substituted alkaryl (such as phenyl, alkoxyphenyl, benzyl, alkoxybenzyl) are also synthesized by reaction of the phosphonic acid with thionyl chloride and a catalytic amount of DMF in a solvent such as acetonitrile. The resulting dichloridate is then reacted with about 4, 5 or 6 equivalents of the sodium or potassium alkoxide or a sodium or potassium aryloxide obtained from reaction with sodium hydride or potassium hydride and the alcohol (such as phenol, benzyl alcohol and the like) in a solvent such as THF or acetonitrile at a reduced temperature (below about –70° C., preferably about –76° C. to –78° C.).

The internally cyclized analogues having structures (2), (3) and (4) are prepared by a number of suitable methods from the free hydroxy phosphonic acid. These methods include treatment with DCC in DMF, reaction with Vilsmeier's reagent ($ClCH=N(CH_3)_2Cl$), or methods of phosphate activation known per se. In one embodiment of this invention for the preparation of the corresponding cyclized compound from the parental phosphonate nucleotide, the phosphonate is (a) treated with $ClCH=N(CH_3)_2Cl$ to yield the phosphonylchloridate and (b) optionally the phosphonylchoridate is reacted with a nucleophile (preferably at low temperature, e.g. lower than about –20° C.) such as an alcohol or amine to produce one of the intermediates described above. In a further step the product of steps (a) or (b) is subject to hydrolysis or protonolysis (typically acid protonolysis) respectively to yield the cyclic compound. Vilsmeier's reagent is advantageously produced in situ by combining $SOCl_2$, $PCl_5$, $POCl_3$, $COCl_2$ or the like with DMF. Advantageously, the product of step (a) is not purified or separated from the reaction mixture before being reacted with the nucleophile, a distinct economic advantage for this synthetic route.

Internally cyclized dihydroxy compounds of this invention where the remaining Y group is an ester or amide typically are made by reacting the appropriate cyclic compound with SOCl$_2$/DMF to yield the activated phosphonyl-chloride (see scheme 4), followed by treatment with the corresponding nucleophile (e.g. alkoxide, phenolate, amine, etc.) to yield the protected intermediate formamidine which is subsequently hydrolyzed to the target compound (48). Alternatively, esters can also be prepared as depicted in scheme 5. The N-,O- protected intermediate phosphonate diester is obtained. The N- and O- protecting groups are subsequently removed followed by treatment of the phosphonate diester with NaH leading to cyclization yielding target compound. A third method for the synthesis of esters of the cyclic compounds entails alkylation of the cyclic compounds using common alkylating agents R$^3$Lv (where Lv is a leaving group) such as alkyl halides, tosylates, diazoalkanes and the like (see scheme 6). This method is particularly useful for preparing acyloxyalkyl esters by treatment of the cyclic compound with the corresponding acyloxyalkylhalide. In an exemplary method for the preparation of acyloxyalkyl esters of the cyclic compounds, triethylamine and R$^3$C(O)OCH$_2$Cl are reacted with the cyclic compound. The stoichiometric proportion of triethylamine: R$^3$C(O)OCH$_2$Cl: cyclic compound may be selected to be 1–2:1–2:1. Use of such low proportions of reactants may lessen side reactions with any exocyclic amino group of B and thereby greatly improve yields.

Each of the following schemes exemplify compound (30) as the nucleotide analogue. However, any B is employed in place of cytosine, provided that any exocyclic oxo or amino groups are protected as required. Also, step 3 of scheme 4 will be omitted when B contains no exocyclic amine.

Scheme 4

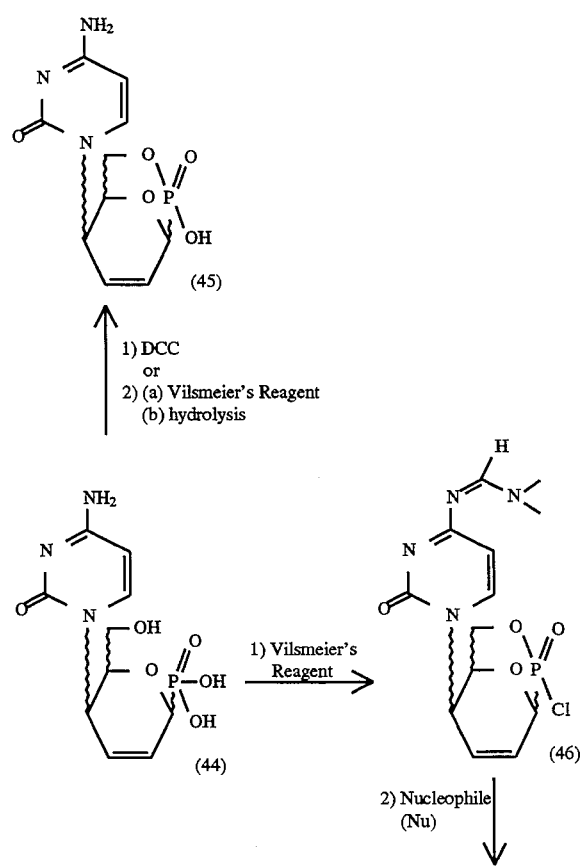

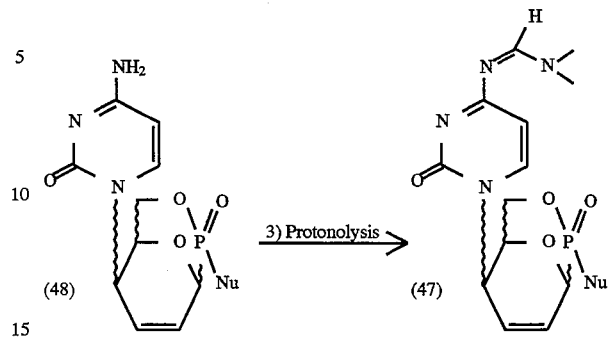

Scheme 5

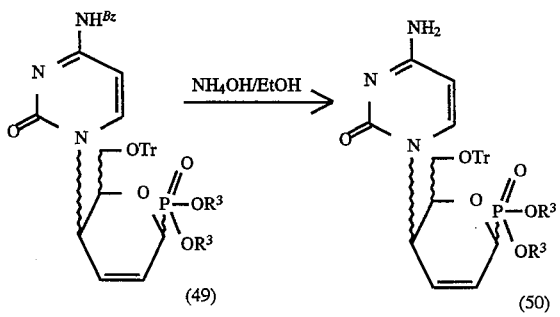

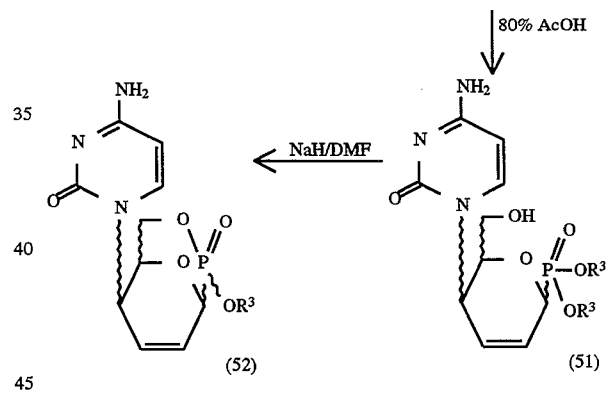

Scheme 6

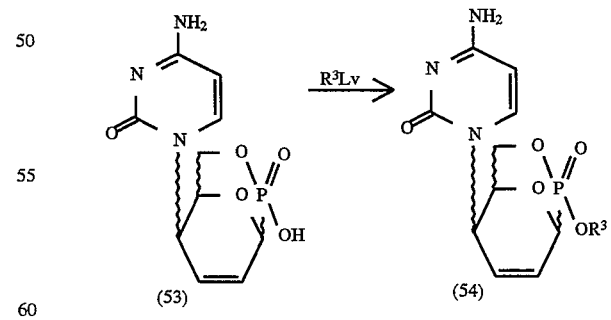

Methods for linking cholesteryl, saccharide and other moieties to reactive groups have been described (Hadfield, "Adv. Pharmacol. Chemother." 20:21 (1984); Gouyette, "Tet. Lett." 30:6019 (1989); Ksander, "J. Med. Chem." 37:1823 (1994), and are adapted here to substitute such Y moieties into the phosphonate).

Bis esters are converted to monoesters by chemical hydrolysis in base or acid according to the bis ester used. For example, treatment with NaOH (0.5 to 2N) or $NH_4OH$ in a solvent such as THF (tetrahydrofuran), dioxane or an alcohol for 1 to 24 hours at 22° to 90° is suitable for most esters. The choice of solvent will depend on the characteristics of the bis ester used. The hydrolytic stability of the phosphonate bis esters is unequal and provides a means for obtaining the monoester. Selection of hydrolysis conditions is determined by routine testing. Alkaline hydrolysis yields the phosphonate monoester and a corresponding alcohol or phenol. Other Y groups are then linked to the monoester using reagents and conditions (i.e., a 1:1 mixture of triphenylphosphine ($PPh_3$) and 2,2'-dipyridyl disulfide in a suitable solvent such as pyridine or DMF) essentially as described for synthesis of bis amidates.

Mixed bis amidate synthesis. Synthesis of compounds of structure (1) where both Y are amino acids or where one Y is an amino acid and the other is an amine ($NH_2$, $NHR^3$, $N(R^3)_2$) is accomplished by direct conversion as described above for bis amidates followed by separation of the final products. Another method to synthesize mixed bis amidates is amidation of an appropriate phosphonate monoester, followed by removal of the ester group under conditions that do not remove the first amide. Synthesis of phosphonate monoester compounds has been described (EP 481 214). Such compounds are then converted to the mixed bis amide by condensation with a second amino acid or amine as described (i.e., using a 1:1 mixture of triphenylphosphine and 2,2'-dipyridyl disulfide) to yield the final product.

Mono amidate synthesis. Synthesis of compounds of structure (1) where one Y is an amino acid and the other is OH is accomplished essentially as described for bis amidate synthesis. Cyclic phosphonates are prepared by direct dehydration of the corresponding dihydroxy nucleotide analogue using DCC (dicyclohexylcarbo-diimide) or 4-morpholino-N,N'-dicyclohexylcarboxamide as described (Ho et al. "Mol. Pharmacol." 41:197–202 (1992)). The cyclic phosphonate is condensed with an amino acid ester in the presence of a 1:1 mixture of triphenylphosphine and 2,2'-dipyridyl disulfide in a suitable solvent such as pyridine or DMF.

Protected heterocyclic base compounds. The present invention includes nucleotide analogues that comprise a protected heterocyclic base. These compounds are useful as synthetic intermediates and/or, as antiinfective or antiviral agents per se.

Exocyclic amines of the compounds of this invention are protected by reacting the nucleotide analogue with $R^3C(O)Cl$ or $(CH_3O)_2CHR^3$. The exocyclic amine groups such as the $N^4$-amine of cytosine, the $N^6$-amine of adenine and the $N^2$-amine of guanine are protected. Suitable methods are essentially as described (Gilliam, "Anal. Biochem." 157:199 (1986); Gallo-Rodriguez, "J. Med. Chem." 37:636 (1994); Maillard, "J. Pharm. Sci." 83:46 (1994)).

The exemplary reaction schemes used to synthesize protected and cyclized heterocyclic base compounds shown below utilize compound (30) where B=cytosine.

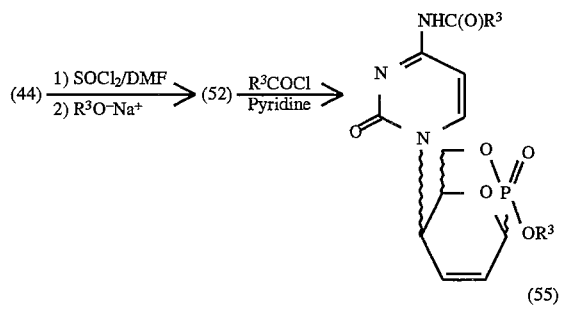

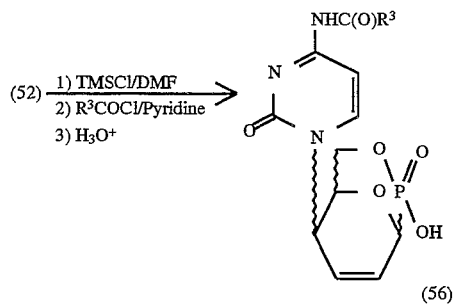

wherein $R^3$ is as defined above. Either procedure is readily adapted to compounds in which the heterocyclic base is, for instance, adenine, guanine, 2,6-diaminopurine or 2-aminopurine where an exocyclic amine is linked to the base. The cyclic esters may comprise a single isomer or a scalemic mixture at the phosphorus atom. Low temperature reaction conditions (lower than about –20°, e.g., about –20° to about –40° C. or about –40° to about –80° C.) may tend to favor single isomer products, while reaction at higher temperatures (above about –20°, e.g. –20° to 40° C.) may result in a scalemic mix. The pivaloyloxymethyl ester synthesis may yield a scalemic mixture at the phosphorus atom. When and if a scalemic mixture is obtained, the isomers are conveniently separated by HPLC, although the mixture can be used, for example, as a synthetic intermediate or as an active antimicrobial agent, without resolution at the #6 site.

A method to obtain heterocyclic bases comprising the $C(O)R^3$ protecting group is accomplished as follows using the acyl chloride ($R^3C(O)Cl$) using compound (30) as an example

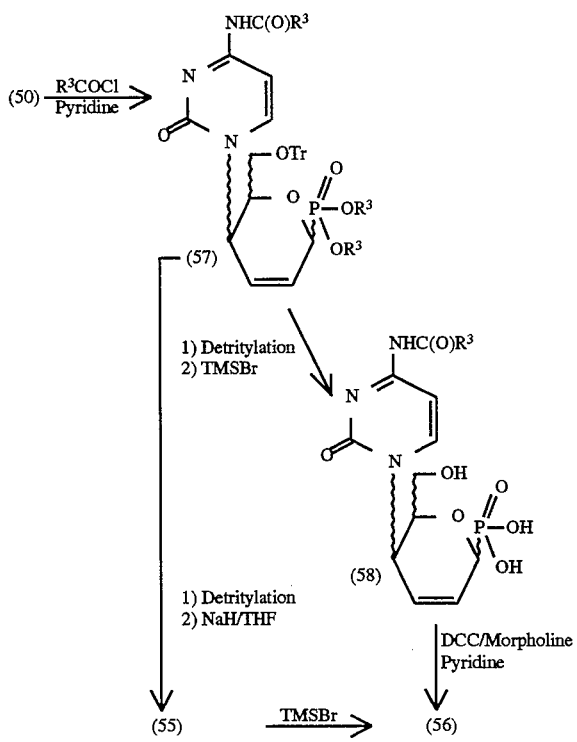

wherein Tr is the hydroxyl protecting group trityl. The detritylation step is accomplished by acid treatment, such as 80% acetic acid at about 20° to 80° C. for 4–24 hours. The $R^3$ moiety is removed using a Lewis acid such as TMSBr to yield the free phosphonate.

Phosphonate compounds comprising a $C_2$-$C_{20}$ 1-acyloxy-1-alkyl or a $C_4$-$C_{20}$ 1-acyloxy-1-alkyl-1-aryl ester group are prepared as follows

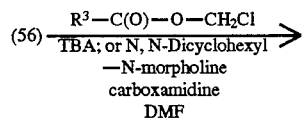

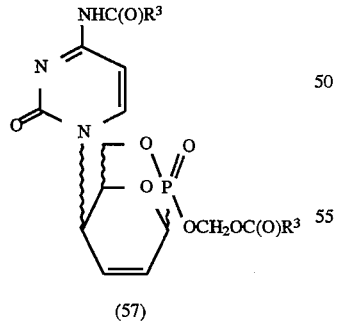

wherein $R^3$ is defined above.

The amine protecting group $=CRN(R)_2$ is incorporated into an exocyclic amine to yield protected heterocyclic base compounds as follows

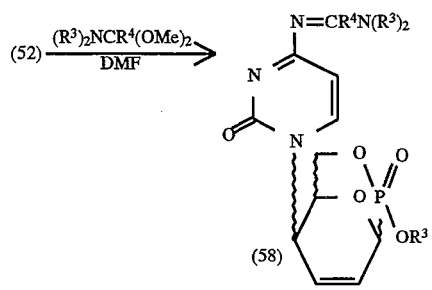

Exemplary $R^3$ alkyl groups include methyl, ethyl, propyl, isopropyl, cyclopropyl, butyl, isobutyl and cyclobutyl. In general, both $R^3$ alkyl groups will be the same. The reaction can be carried out in dry DMF at room temperature (about 20°–30° C.) as previously described (Kerr et al. "J. Pharm. Sci." 83:582 (1994); Kerr et al. "J. Med. Chem." 35:1996 (1992)), or DMF can be substituted with $CH_3CN$ and 4 Å molecular sieves. Exemplary compounds include species where R is hydrogen, alkyl (including ethyl, propyl, isopropyl), aryl (including phenyl) or acyloxymethyl. Protected heterocyclic bases where $R^4$ is hydrogen are stable under neutral anhydrous conditions and are generally labile under acidic aqueous conditions. When $R^4$ is methyl, the protecting group is more stable to aqueous acidic or basic conditions.

Compounds containing a protected heterocyclic base and 1 or 2 amino acids, dipeptides or oligopeptides attached to the phosphorus atom via an amidate linkage are obtained as described for synthesis of bis-amidate or amidate-ester compounds.

Table 7 lists $R^3$ ester and Y amidate moieties that can be bonded via oxygen or directly, respectively, to the phosphorus atom. Esters of structures 1–5, 8–10 and 16, 17, 19–22 are synthesized by reacting a nucleotide analogue having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). Esters of structures 5–7, 11, 12, 21, and 23–26 are synthesized by reaction of the alcohol or alkoxide salt (or the corresponding amines in the case of compounds such as 13, 14 and 15) with the monochlorophosphonate or dichlorophosphonate or another activated phosphonate.

TABLE 7

1. $-CH_2-C(O)-N(R^{15})_2$*
2. $-CH_2-S(O)(R^{15})$
3. $-CH_2-S(O)_2(R^{15})$
4. $-CH_2-O-C(O)-CH_2-C_6H_5$
5. 3-cholesteryl
6. 3-pyridyl
7. N-ethylmorpholino
8. $-CH_2-O-C(O)-C_6H_5$
9. $-CH_2-O-C(O)-CH_2CH_3$
10. $-CH_2-O-C(O)-C(CH_3)_3$
11. $-CH_2-CCl_3$
12. $-C_6H_5$
13. $-NH-CH_2-C(O)O-CH_2CH_3$
14. $-N(CH_3)-CH_2-C(O)O-CH_2CH_3$
15. $-NHR^3$
16. $-CH_2-O-C(O)-C_{10}H_{15}$
17. $-CH_2-O-C(O)-CH(CH_3)_2$
18. $-CH_2-C\#H(OC(O)CH_2R^{15})-CH_2-(OC(O)CH_2R^{15})$*

TABLE 7-continued

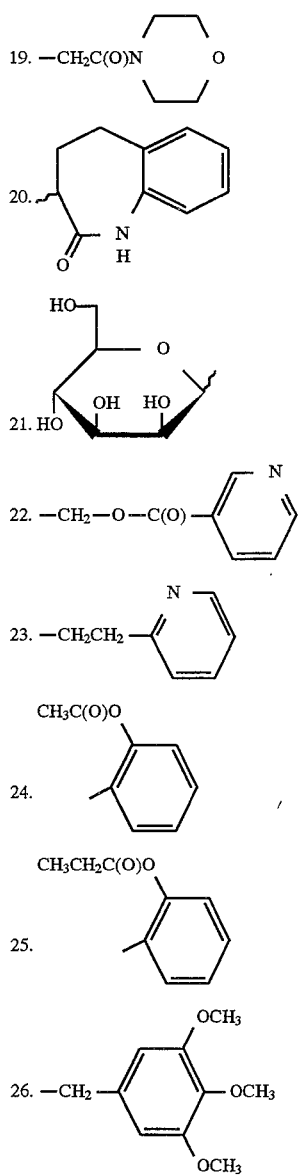

*Each $R^{15}$ is the same or different (includes methyl, ethyl, propyl, isopropyl and t-butyl).
chiral center is (R), (S) or racemate.

Other esters that are suitable for use herein are described in EP 632,048.

To the extent any compound of this invention cannot be produced by one of the foregoing schemes other methods will be apparent to the artisan referring to conventional methods (see for instance Liotta et al. "Compendium of Organic Synthesis Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; March, J., "Advanced Organic Chemistry, Third Edition", (John Wiley & Sons, New York, 1985); as well as "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

All citations are hereby expressly incorporated by reference. The following examples are illustrative and do not limit the scope of this invention.

EXAMPLE 1

Synthesis of Diisopropyl(4,6-di-O-acetyl-2,3-dideoxy-α-and -β-D-erythro-hex-2-enopyranosyl) phosphonate (22)

(21)→(22)

To solution of (2.72 g,10 mmol) of 3,4,6-tri-O-acetyl1,2-dideoxy-D-arabino-hex-1-enopyranose (3,4,6-tri-O-acetyl-D-glucal) and (3.12 g, 15 mmol) of triisopropylphosphite in dry toluene (20 ml) was added boron trifluoride etherate (0.18 ml, 1.5 mmol). The mixture was heated to 100° C. for 4 h. The solvent was removed, residue was codistilled three times with toluene (50 ml), and purified by column chromatography on silica gel, eluting with hexane-ethyl acetate 4:1 to afford (22) as a colorless oil (3.145 g, 83%). (Modified procedure from H. Paulsen, "J. Thiem: Chem. Ber." 106:3850–3876 (1973).)

EXAMPLE 2

Synthesis of Diisopropyl(2,3-dideoxy-α-and -β-D-erythro-hex-2-enopyranonate (23)

(22)→(23)

Compound (23), (3.79 g, 10 mmol) was dissolved in saturated solution of $NH_3$ in MeOH and stirred at ambient temperature for 6 h. The solvent was removed and the residue codistilled with toluene. Drying afforded (23), 2.94 g as a mixture of α and β anomers 1:1 (100%).

EXAMPLE 3

Synthesis of Diisopropyl-(2,3-dideoxy-6-triphenylmethyl-α-D-erythro-hex-2-enopyranosyl) phosphonate (24a) and Diisopropyl(2,3-dideoxy-6-O-triphenylmethyl-β-D-erythro-hex-2-enopyranosyl) phosphonate (24b)

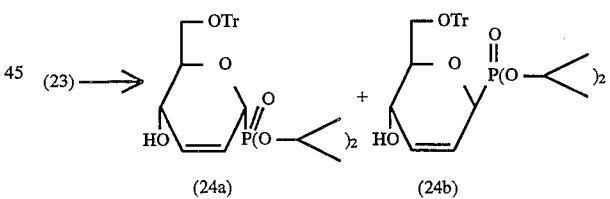

To a solution of compound (23), (2.94 g, 10 mmol) in toluene (50 ml) was added triphenylmethylchloride (2.79 g, 10 mmol) and pyridine (3 ml). Mixture was stirred at ambient temperature for 24 h. Toluene was added (150 ml) and the mixture was extracted with 1M hydrochloric acid, a saturated solution of $NaHCO_3$ and water. The organic phase was dried ($MgSO_4$), filtered, and evaporated to leave an oil which was purified by column chromatography on silica gel, eluting with hexane-ethyl acetate (5:1, 3:1) to give pale yellow oils of (24a) (α anomer, 2.09 g, 39%) and (24b) (β anomer, 2.46 g, 46%): (24a): $^1$H NMR ($CDCl_3$) δ 1.28 (m, 12H), 3.40 (m,2H), 3.53 (m,1H), 4.22 (m,1H), 4.53 (d, J=17.5 Hz, 1H), 4.76 (m, 1H), 5.94 (, 2H), 7.28 (m, 15H). (24b): $^1$H NMR ($CDCl_3$) δ 1.32 (m, 12H), 3.27 (m, 1H), 3.35 (m, 1H), 4.07 (brs, 1H), 4.21 (m, 1H), 4.42 (m, 1H), 4.77 (m, 1H), 5.88 (m, 1H), 6.02 (m, 1H), 7.28 (m, 15H).

EXAMPLE 4

Synthesis of Diisopropyl[4-($N^4$-benzoylcytosin-1-yl)-2,3-dideoxy-6-O-triphenylmethyl-β-D-threo-hex-2-enopyranosyl]phosphonate (25')

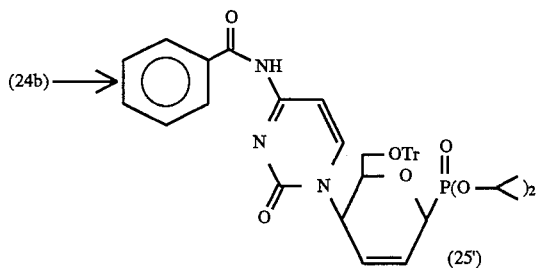

To a 0° C. stirred solution of triphenylphosphine (0.786 g, 3 mmol) in anhydrous THF (20 ml) under dry nitrogen atmosphere, was added diethyl azodicarboxylate (0.522 g, 3 mmol). After the mixture was stirred for 30 min, compound (24b) was added followed by $N^4$-benzoylcytosine. After the mixture was stirred at 0° C. for 24 h, the solvent was removed and the residue was purified by column chromatography on silica gel (CH$_2$Cl$_2$—MeOH) m give (25') (0.557 g, 38%): $^1$H NMR (CDCl$_3$) δ 1.39 (m,12H), 3.14 (m, 2H), 3.92 (m, 1H), 4.62 (m, 1H), 4.85 (m,2H), 5.53 (m, 1H), 6.05 (m, 1H), 6.42 (d, J=7.2 1H), 7.10–7.60 (m, 20H), 7.92 (d, J=7.2 1H).

EXAMPLE 5

Synthesis of Diisopropyl[4-(cytosin-1-yl)-2,3-dideoxy-6-O-triphenylmethyl-β-D-threo-hex-2-enopyranosyl]phosphonate (25")

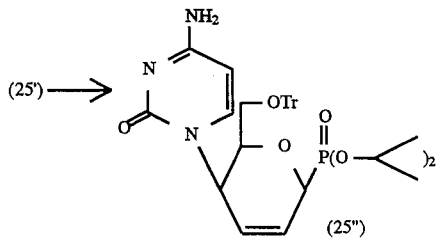

Compound (25') (0.557 g, 0.76 mmol) was treated with saturated solution of NH$_3$ in MeOH (20 ml) for 16 h at ambient temperature. The solvent was removed and product was purified by silica gel chromatography to give (25") (0.38 g, 80%): $^1$H NMR (CDCl$_3$) δ 1.40 (m, 12H), 3.32 (m, 1H), 3.48 (m, 1H), 4.04 (m, 1H), 4.72 (d, J=17.5 Hz1H), 5.12 (m, 2H), 5.65 (m, 1H), 5.82 (d, J=7.1 1H), 6.20 (m, 1H), 6.30 (m, 1H), 7.1–7.6 (m, 15H), 7.83 (d, J=7.1 1H).

EXAMPLE 6

Synthesis of Diisopropyl[4-(cytosin-1-yl)-2,3-dideoxy-β-D-threo-hex-2-enopyranosyl]phosphonate (29')

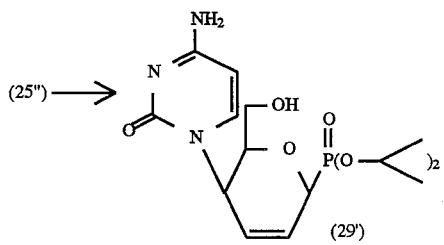

Compound (25") (0.38 g, 0.6 mmol) was dissolved in 80% acetic acid and stirred at ambient temperature for 16 h. The solvent was removed and product isolated by silica gel chromatography to give (29') (0.195 g, 83%): $^1$H NMR (CDCl$_3$) δ 1.35(m, 12 H), 3.28 (m, 1H), 3.56 (m, 1H), 3.88 (m, 1H), 4.58 (d, J=18 Hz, 1H), 4.77 (m, 2H), 5.40 (m, 1H), 5.79 (d, J=7.2 Hz, 1H), 6.04 (m, 1H), 6.34 (m, 1H), 7.98 (d, J=7.2 Hz, 1H).

EXAMPLE 7

Synthesis of 4-(cytosin-1-yl)-2,3-dideoxy-β-D-threo-hex-2-enopyranosylphosphonic acid (30')

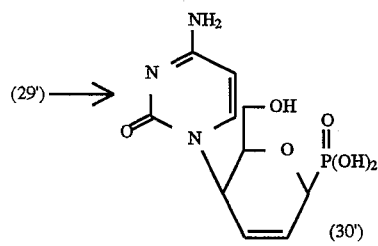

To a solution of (29') (0.195 g, 0.5 mmol) in acetonitrile (5 ml) was added 2,4-lutidine (0.6 ml, 5 mmol) and trimethylbromosilane (0.66 ml, 5 mmol) and the mixture was stirred for 24 h. Solvent was evaporated and the dry residue was coevaporated with methanol, (10 ml). The residue was dissolved in water (5 ml) and applied on Dowex 1 [AcO$^-$ form] (20 ml), eluting with water (300 ml) and 0.1M acetic acid. Product-containing fractions were collected, evaporated and the residue was precipitated from H$_2$O-acetonitrile to give white precipitate of (30') (0.136 g, 90%): mp 250°–300° C. decomp.; $^1$H NMR (CDCl$_3$) δ 3.50–3.74 (m, 2H), 4.01 (m, 1H), 4.58 (dd J=18.0, 1.83 Hz, 1H), 5.29 (m, 1H), 5.96 (m, 1H), 6.18 (d, J=7.9 Hz, 1H), 6.53 (m, 1H), 8.26 (d, J=7.9 Hz, 1H); HRMS, 304.0692 (M+H-glycerol), calcd for C$_{10}$H$_{15}$N$_3$O$_6$P 304.0698.

EXAMPLE 8

Synthesis of Diisopropyl[4-(cytosin-1-yl)-2,3-dideoxy-β-D-threo-hexopyranosyl]phosphonate (31')

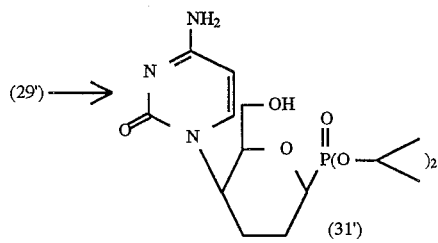

Compound (29') (0.198 g, 0.5 mmol) was dissolved in methanol (10 ml), catalytic amount of 10% Pd/C was added and mixture was hydrogenated by $H_2$ under 200 Psi for 4 hours. Then mixture was filtered through celite and evaporation afforded 0.195 g of (31') as a white solid: $^1$H NMR (CDCl$_3$) δ 1.27 (m, 12H), 1.75 (m, 2H), 2.00 (m, 2H), 3.49 (m, 1H), 3.67 (m,1H), 3.88 (m, 2H), 4.76 (m, 2H), 4.97 (m, 1H), 5.71 (m, 1H), 8.14 (m, 1H).

EXAMPLE 9

Synthesis of 4-(cytosin-1-yl)-β-D-threo-hexopyranosylphosphonic acid (32')

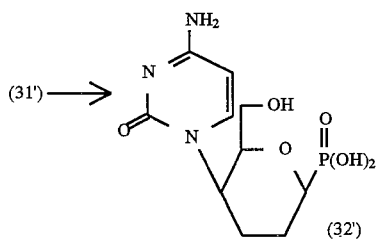

To a solution of (32') (0.195 g, 0.49 mmol) in acetonitrile (5 ml) was added 2,4-lutidine (0.6 ml, 5 mmol) and trimethylbromosilane (0.66 ml, 5 mmol) and the mixture was stirred for 24 h. Solvent was evaporated and dry residue was coevaporated with methanol (10 ml). The residue was dissolved in water (5 ml) and applied on Dowex 1 [AcO-form] (20 ml), eluting with water (300 ml) and 0.1M acetic acid. Product containing fractions were collected, evaporated and residue was precipitated from $H_2O$-acetonitrile to give a white precipitate of (32') (0.136 g, 90%): mp 217° C.; $^1$H NMR (CDCl$_3$) δ 1.71 (m, 2H), 2.00 (m, 2H), 3.49 (m, 2H), 3.73 (m, 1H), 3.91 (m, 1H), 4.59 (m, 1H), 6.05 (d, J=8.0 Hz, 1H), 8.51 (d, J=8.0 Hz, 1H). HRMS, 306.0859 (M+H-glycerol), calcd for $C_{10}H_{17}N_3O_6P$ 306.0855.

EXAMPLE 10

Synthesis of Diisopropyl[4-($N^4$-benzoylcytosin-1-yl)-2,3-dideoxy-6-O-triphenylmethyl-α-D-threo-hex-2-enopyranosyl]phosphonate (26')

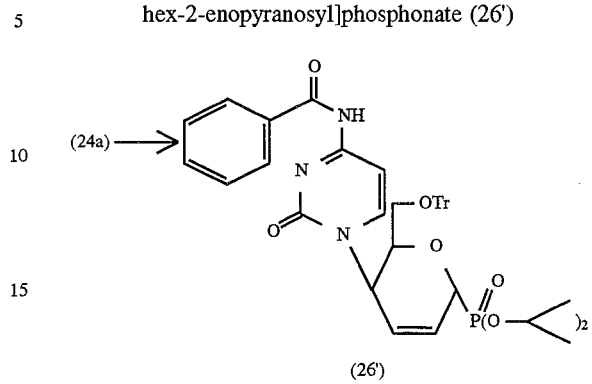

Starting from compound (24a) and repeating the process of example 4, compound (26') was prepared: $^1$H NMR (CDCl$_3$) δ 1.38 (m, 12H), 3.15 (m, 2H), 3.95 ((m, 1H), 4.62 (m, 1H), 4.85 (m, 2H), 5.52 (m, 1H), 6.08 (m,2H), 6.40 (d, J=7.8 Hz 1H), 7.1–7.4 (m, 20H), 7.92 (d, J=7.8 1H).

EXAMPLE 11

Synthesis of Diisopropyl[4-(cytosin-1-yl)-2,3-dideoxy-6-O-triphenylmethyl-D-threo-hex-1-enopyranosyl]phosphonate (27')

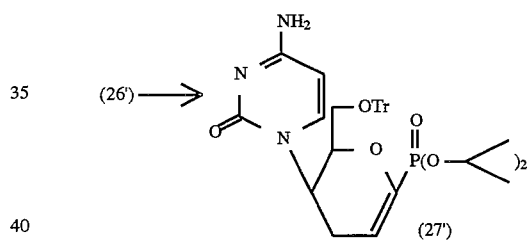

Starting from compound (26') and repeating the procedure from example 5, compound (27') was prepared: $^1$H NMR (CDCl$_3$) δ 1.32 (m,12H), 2.17 (m, 1H), 2.77 (m,1H), 3.29 (m, 2H), 4.21 (m, 1H), 4.74 (m, 2H), 5.31 (d, J=7.2 Hz 1H), 5.44 (d, J=7.3 Hz 1 Hz), 5.99 (m, 1H), 7.25 (m, 15H), 7.82 (d, J=7.3 1H).

EXAMPLE 12

Synthesis of Diisopropyl[4-(cytosin-1-yl)-2,3-dideoxy-D-threo-hex-1-enopyranosyl]phosphonate (27")

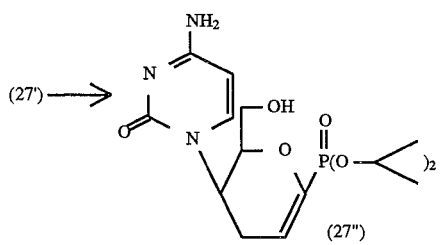

Starting from compound (27') and repeating the procedure from example 6, compound (27") was prepared: $^1$H NMR (CDCl$_3$) δ 1.31 (m, 12H), 2.23 (m, 1H), 2.93 (m, 1H), 3.33 (m, 1H), 3.73 (m, 1H), 4.04 (m 1H), 4.67 (m, 2H), 5.36 (m, 1H), 5.74 (d, J=7.5 Hz 1H), 6.12 (m, 1H), 7.31 (d, J=7.5 Hz, 1H).

EXAMPLE 13

Synthesis of 4-(cytosin-1-yl)-2,3-dideoxy-D-threo-hex-1-enopyranosyl phosphonic acid (28')

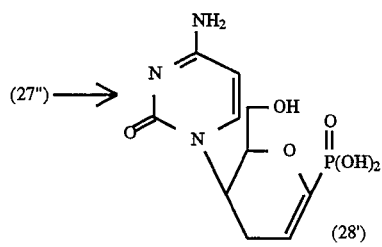

Starting from compound (27") and repeating the procedure from example 7, compound (28') was prepared: mp 290° C.: $^1$H NMR (CDCl$_3$) δ 2.12 (m, 1H), 2.84 (m, 1H), 3.51 (m, 1H), 3.68 (m, 1H), 4.02 (s, 1H), 5.07 (d, J=7.3 Hz 1H), 5.69 (d, J=9.52 Hz 1H), 6.06 (d, J=8.05 Hz 1H), 7.56 (d, J=8.05 Hz 1H). HRMS, 304.0697 (M+H-glycerol), calcd for C$_{10}$H$_{10}$N$_3$O$_6$P 306.0698.

EXAMPLE 14

Synthesis of 4-(cytosin-1-yl)-2,3-dideoxy-β-L-threo-hex-2-enopyranosyl phosphonate (60)

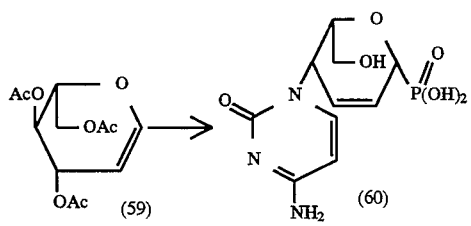

Starting from (59) 3,4,6-tri-O-acetyl-1,2-dideoxy-L-arabino-hex-1-enopyranose (3,4,6-tri-O-acetyl-L-glucal), and repeating the procedures from examples 1 to 7, compound (60) was prepared: mp 250°–300° C. decomp; $^1$H NMR (CDCl$_3$) δ 3.40–3.64 (m, 2H), 3.93 (m, 1H), 4.50 (d J=18.1 Hz 1H), 5.22 (m, 1H), 5.88 (m, 1H), 6.06 (d, J=7.5 Hz 1H), 6.45 (m, 1H), 8.12 (d, J=7.5 Hz, 1H).

EXAMPLE 15

Synthesis of 4-(cytosin-1-yl)-2,3-dideoxy-L-threo-hex-1-enopyranosylphosphonic acid (61)

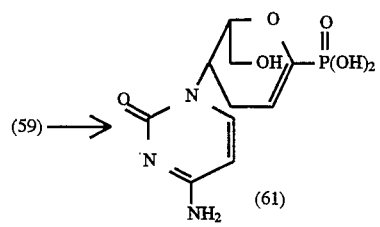

Starting from compound (59) and repeating the procedures from examples 1 to 3, and from 10 to 13, compound (61) was prepared: mp 290° C.; $^1$H NMR (CDCl$_3$) δ 2.14 (m, 1H), 2.91 (m, 1H), 3.53 (m, 1H), 3.72 (m, 1H), 4.08 (m, 1H), 5.12 (d, J=8.1 Hz 1H), 5.76 (m, 1H), 6.05 (d, J=7.5 Hz 1H), 7.56 (d, J=7.5 Hz 1H).

EXAMPLE 16

Synthesis of Diisopropyl 2,3,6-trideoxy-α- and -β-L-erythro-hex-2-enopyranosylphosphonate (63)

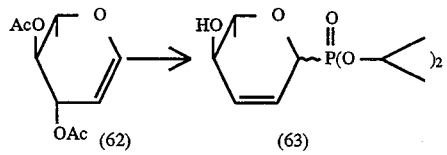

Starting from 3,4-di-O-acetyl-1,2,6-trideoxy-L-arabino-hex-1-enopyranose (3,4-di-O-acetyl-6-deoxy-L-glucal) (62) and repeating the procedures from examples 1 and 2 compound (63) was made as a mixture of α and β anomers: $^1$H NMR (CDCl$_3$) δ 1.25 (m,15H), 3.32 (m, 1H), 3.82 (m, 1H), 4.38 (m, 1H), 4.72 (m, 2H), 5,98 (m, 2H).

EXAMPLE 17

Synthesis of 4-(cytosin-1-yl)-2,3,6-trideoxy-β-L-threo-hex-2-enopyranosylphosphonic acid (64) and 4-(cytosin-1-yl)-2,3,6-trideoxy-L-threo-hex-1-enopyranosylphosphonic acid (65)

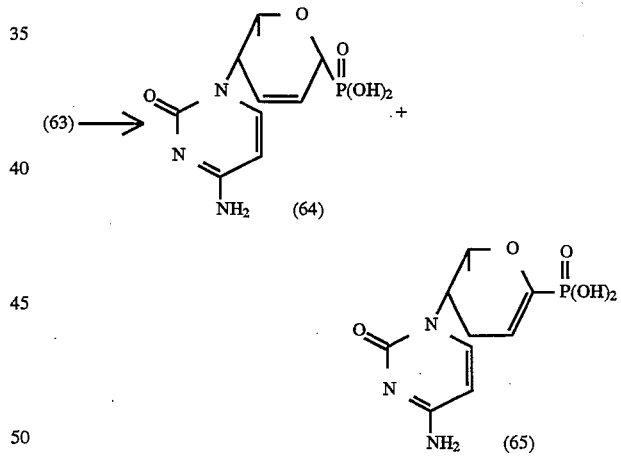

Starting from mixture of anomers of compound (63) and repeating procedures from examples 4, 5, and 7, compounds (64) and (65) were prepared. The α and β anomers were separated after deprotection step (example 5) by silica gel chromatography: (64): mp 288° C.; $^1$H NMR (CDCl$_3$) δ 1.03 (d, J=6.54 Hz, 3H), 4.03 (m, 1H), 4.50 (d, J=17.58 Hz 1H), 5.12 (m, 1H), 5.94 (m, 1H), 6.04 (d, J=7.3 Hz 1H), 6.43 (m, 1H), 8.05 (d, J=7.3). HRMS, 288.0756 (M+H-glycerol), calcd for C$_{10}$H$_{15}$N$_3$O$_5$P 288.0749. (65): mp 285° C.; $^1$H NMR (CDCl$_3$) δ 1.16 (d, J=6.3 Hz 3H), 2.20 (m, 1H), 2.88 (m, 1H), 4.21 (m, 1H), 5.04 (d, J=7.8 Hz 1H), 5.76 (m, 1H), 6.06 (d, J=7.8 Hz 1H), 7.54 (d, J=7.8 Hz 1H); HRMS, 288.0754 (M+H-glycerol), calcd for C$_{10}$H$_{15}$N$_3$O$_5$P 288.0749.

EXAMPLE 18

Synthesis of 4-(adenine-9-yl)-2,3-dideoxy-D-threo-hex-1-enopyranosyl phosphonic acid (28")

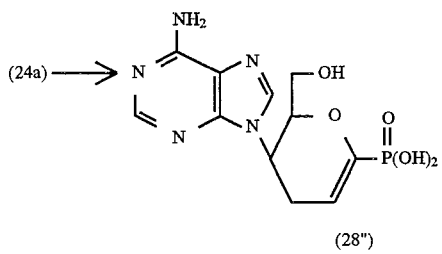

Starting from compound (24a) and using the procedures from examples 4, 5, 6 and 7 (except instead of N$^4$-benzoylcytosine, N$_6$-benzoyladenine was used) compound (28") was prepared: $^1$H NMR (CDCl$_3$) δ 2.43 (m, 1H), 3.08 (m, 1H), 3.33 (m, 1H), 3.61 (m, 1H), 4.34 (m, 1H), 5.34 (m, 1H), 5.35 (d, J=6.84 Hz, 1H), 5.87 (m, 1H), 8.27 (s, 1H), 8.45 (s, 1H).

EXAMPLE 19

Synthesis of 4-(adenine-9-yl)-2,3,6-trideoxy-L-threo-hex-1-enopyranosylphosphonic acid (65')

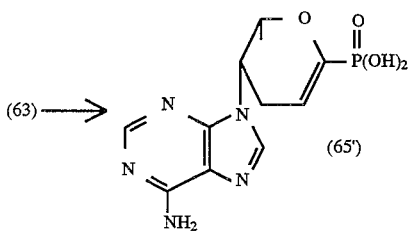

Starting from compound (63) and using the procedures from examples 4, 5, and 7 (except instead of N$^4$-benzoylcytosine, N$^6$-benzoyladenine was used) compound (65') was prepared: mp 151° C.: $^1$H NMR (CDCl$_3$) δ 1.00 (d, J=6.35 Hz 3H), 2.37 (m, 1H), 2.99 (m, 1H), 4.37 (m, 1H), 4.99 (d, J=6.84 Hz 1H), 5.78 (m, 1H), 8.10 (s, 1H), 8.24 (s, 1H) HRMS, 312.0862 (M+H-glycerol), calcd for C$_{11}$H$_{15}$N$_5$O$_4$P 312.0861.

EXAMPLE 20

Synthesis of 4-(thymin-1-yl)-2,3,6-trideoxy-α-L-threo-hex-2-enopyranosyl phosphonic acid (66) 4-(thymin-1-yl)-2,3,6-trideoxy-β-L-threo-hex-2-enopyranosylphosphonic acid (64') and 4-(thymin-1-yl)-2,3,6-trideoxy-L-threo-hex-1-enopyranosylphosphonic acid (65")

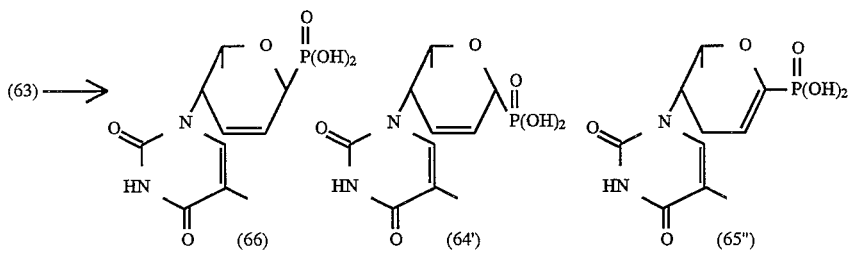

Starting from compound (63) and using procedures from examples 4, 5, and 7 (except instead of N$^4$-benzoylcytosine, N$^3$-benzoylthymine was used). The mixture was separated after deprotection of base (example 5) and each isolated compound was deprotected by trimethylbromosilane (example 7): (66): $^1$H NMR (CDCl$_3$) δ 1.00 (d, J=6.59 Hz 3H), 1.86 (s, 3H), 3.92 (m, 1H), 4.44 (m, 1H), 4.97 (m, 1H), 5.82 (m, 1H), 6.53 (mm, 1H), 7.41 (s, 1H). (64'): $^1$H NMR (CDCl$_3$) δ 1.06 (d, J=5.86 Hz 3H), 1.87 s, 3H), 3.99 (m, 1H), 4.41 (m, 1H), 4.99 (m, 1H), 5.86 (m, 1H), 6.48 (m, 1H), 7.38 (s, 1H); HRMS 325.0578 (M+H-glycerol), calcd for C$_{11}$H$_{15}$N$_2$O$_6$NaP 325.0565. (65"): $^1$H NMR (CDCl$_3$) δ 1.17 (d, J=1.17 Hz 3H), 1.88 (d, J=0.99 Hz 3H), 2.16 (m, 1H), 2.83 (m, 1H), 4.16 (m, 1H), 4.91 (m 1H), 5.61 (m, 1H), 7.42 (d, J=0.98 Hz 1H); HRMS 325.0573 (M+H-glycerol), calcd for C$_{11}$H$_{15}$N$_2$O$_6$NaP 325.0578.

EXAMPLE 21

Compounds made in the foregoing examples were assayed for inhibitory effect against human CMV using the standard plaque inhibition assay (Lurain, "J. Vir." 66:7146–7152 (1992)). The cells used for the toxicity assay were normal human dermal fibroblasts. The results are shown in Table 8 below.

TABLE 8

| Compound Tested | IC$_{50}$ (μM) | CC$_{50}$ (μM) |
|---|---|---|
| (30) | 10 | >1000 |
| (28') | 40 | >1000 |
| (32') | 80 | >1000 |
| (64) | 200 | >1000 |
| (65) | 300 | >1000 |

A related known compound, HPMPC, was more potent but also more toxic than the best compound of the invention tested here, exhibiting an IC$_{50}$ of 0.5 micromolar and a CC$_{50}$ of 200 micromolar.

The claims shall be construed to exclude any subject matter that, at the date of the invention, would not have been patentable under applicable statutory and judicial authority.

We claim:

1. A compound having the structure (1)

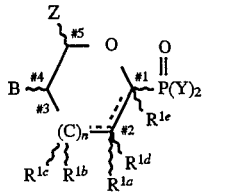

wherein the dashes indicate the positions of optional double bonds;
designates chiral centers, which are numbered;
n is 0 or 1;
Y is OH;
Z is $CH_2OR^2$, halo substituted $C_1$–$C_2$ alkyl, $CH=CH_2$, $C\equiv CH$, —$CH_2N_3$, $CH_3$, or H;
B is a heterocyclic base selected from the group consisting of a 9-purinyl base, the 3-aza, 8-aza or 7-deaza analogue of a 9-purinyl base, and a 1-pyrimidinyl base;
$R^{1a}$ and $R^{1b}$ independently are H, CN, $N_3$, halo, or $OR^2$, or $R^{1a}$ and $R^{1b}$ may be joined together to form a bond or —$CH_2$—;
$R^{1c}$ is H or, when $R^{1a}$ and $R^{1b}$ are joined together to form a bond, $R^{1c}$ is H or F;
$R^{1d}$ and $R^{1e}$ are H or may be joined together to form a bond;
$R^2$ is H;
when n=1 the pyran ring is saturated or is unsaturated at the 1–2 or 2–3 positions;
when n=0, $R^{1d}$ and $R^{1e}$ are H; and
the salts thereof.

2. The compound of claim 1 wherein n is 1, Y is OH, B is a 9-purine or 1-pyrimidine base or the monoaza/monodeaza analogue thereof, the pyran ring is unsaturated, and $R^{1a}$ and $R^{1b}$ are H.

3. The compound of claim 2 wherein B is adenine, guanine, cytosine, uridine or thymidine.

4. The compound of claim 2 wherein Z is $CH_2OH$, $CH_3$ or H.

5. The compound of claim 2 wherein B is the 3-aza, 8-aza, or 7-deaza analogue of a purine base.

6. The compound of claim 1 wherein n is 1, Y is OH, B is a 9-purine or 1-pyrimidine base or the monoaza/monodeaza analogue thereof, the pyran ring is saturated and $R^{1a}$ and $R^{1b}$ independently are OH, or halo.

7. The compound of claim 1 wherein n is 1 and one of $R^{1a}$ or $R^{1b}$ is H.

8. The compound of claim 7 wherein $R^{1a}$ is H.

9. The compound of claim 7 wherein $R^{1b}$ is H.

10. The compound of claim 1 wherein n is 1 and both $R^{1a}$ and $R^{1b}$ are H.

11. The compound of claim 1 which has the (R) or (S) configuration at the #1 site.

12. The compound of claim 1 which has the (R) or (S) configuration at the #4 site.

13. The compound of claim 1 having the same relative stereochemistry at sites 1–5.

14. The compound of claim 1 having (R), (R); (R), (S); (S), (R); or (S), (S) stereochemistry, respectively, at the #1 and #5 sites.

15. The compound of claim 14 which has the (R) configuration at the #4 site.

16. The compound of claim 14 which has the (S) configuration at the #4 site.

17. The compound of claim 15 which has the (R) or (S) configuration at the #2 site.

18. The compound of claim 16 which has the (R) or (S) configuration at the #3 site.

19. The compound of claim 1 having the same relative stereochemistry at sites #2 and #3.

20. The compound of claim 1 having the same relative stereochemistry at sites #1 and #4.

21. The compound of claim 20 having the same relative stereochemistry at site #4 as at sites #1 and #5.

22. The compound of claim 1 wherein n is 1, both $R^{1a}$ and $R^{1b}$ are $OR^2$, and both of these $R^2$ are joined to complete a ring.

23. The compound of claim 1 wherein $R^{1a}$ and $R^{1b}$ are joined to form —$CH_2$—.

24. The compound of claim 1 wherein B is cytosine.

* * * * *